US010994090B2

(12) United States Patent
Patel

(10) Patent No.: US 10,994,090 B2
(45) Date of Patent: May 4, 2021

(54) PATIENT INTERFACES

(71) Applicant: Fisher & Paykel Healthcare Limited, Auckland (NZ)

(72) Inventor: Roheet Patel, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 285 days.

(21) Appl. No.: 15/757,112

(22) PCT Filed: Sep. 1, 2016

(86) PCT No.: PCT/IB2016/055212
§ 371 (c)(1),
(2) Date: Mar. 2, 2018

(87) PCT Pub. No.: WO2017/037638
PCT Pub. Date: Mar. 9, 2017

(65) Prior Publication Data
US 2018/0177965 A1 Jun. 28, 2018

Related U.S. Application Data

(60) Provisional application No. 62/214,463, filed on Sep. 4, 2015.

(51) Int. Cl.
*A61M 16/06* (2006.01)
(52) U.S. Cl.
CPC .... *A61M 16/0622* (2014.02); *A61M 16/0616* (2014.02); *A61M 16/0683* (2013.01); *A61M 2210/0618* (2013.01)
(58) Field of Classification Search
CPC .............. A61M 16/0057; A61M 16/06; A61M 16/0605; A61M 16/0611; A61M 16/0616;
(Continued)

(56) References Cited

U.S. PATENT DOCUMENTS 443,191 A 12/1890 Illing
804,272 A 11/1905 Schwarz
(Continued)

FOREIGN PATENT DOCUMENTS

AU 2004201337 A1 10/2005
CN 102698349 10/2012
(Continued)

OTHER PUBLICATIONS

Hsiao, H., Anthropometric Procedures for Protective Equipment Sizing and Design, Human Factors: The Journal of the Human Factors and Ergonomics Society, 55(1):6-35, Feb. 2013.
(Continued)

*Primary Examiner* — Annette Dixon
(74) *Attorney, Agent, or Firm* — Knobbe, Martens, Olson & Bear, LLP

(57) ABSTRACT

An interface for positive pressure respiratory therapy includes a mask assembly having a mask seal and a mask shell. The mask assembly is positioned lower than and exposes a bridge of the user's nose. The mask seal includes portions that contact opposing sides of the user's nose. Each portion of the mask seal includes supports that help maintain the mask seal's shape. Two covers can be supported relative to the mask assembly and adjacent a respective portion of the mask seal. The covers limit expansion of the portions of the mask seal in response to pressurized air within the mask seal. The supports can transfer load from the mask seal to the covers. An interface system can include multiple size mask seals, which can be designed with consideration of ethnic variations in nose size and/or shape.

19 Claims, 42 Drawing Sheets

(58) Field of Classification Search
CPC .......... A61M 16/0622; A61M 16/0666; A61M
16/0683; A61M 16/0816; A61M 16/0825;
A61M 16/0875; A61M 16/20; A61M
16/208; A61M 2016/0661; A61M
2202/0085; A61M 2202/0225; A61M
2205/0216; A61M 2205/42; A61M
2205/581; A61M 2210/0606; A61M
2210/0618; A61M 2210/0625
See application file for complete search history.

(56) References Cited

U.S. PATENT DOCUMENTS

| | | | |
|---|---|---|---|
| 1,229,050 A | 6/1917 | Robert | |
| 1,445,010 A | 2/1923 | Feinberg | |
| 2,228,218 A | 1/1941 | Schwartz | |
| 2,353,643 A | 7/1944 | Bulbulian | |
| 2,403,046 A | 7/1946 | Bulbulian | |
| 2,415,846 A | 2/1947 | Eugene | |
| 2,706,983 A | 4/1955 | Matheson et al. | |
| 2,931,356 A | 4/1960 | Hermann | |
| 2,939,458 A | 6/1960 | Lundquist | |
| 3,680,555 A | 8/1972 | Warncke | |
| 4,263,908 A | 4/1981 | Mizerak | |
| 4,384,577 A | 5/1983 | Huber et al. | |
| 4,470,413 A | 9/1984 | Warncke | |
| 4,907,584 A | 3/1990 | McGinnis | |
| 5,005,571 A | 4/1991 | Dietz | |
| 5,243,971 A | 9/1993 | Sullivan et al. | |
| 5,513,634 A | 5/1996 | Jackson | |
| 5,540,223 A | 7/1996 | Starr et al. | |
| 5,560,354 A | 10/1996 | Berthon-Jones et al. | |
| 5,570,689 A | 11/1996 | Starr et al. | |
| 5,896,857 A | 4/1999 | Hely et al. | |
| 6,016,804 A | 1/2000 | Gleason et al. | |
| 6,119,694 A | 9/2000 | Correa et al. | |
| 6,123,071 A | 9/2000 | Berthon-Jones et al. | |
| 6,467,483 B1 | 10/2002 | Kopacko et al. | |
| 6,470,886 B1 | 10/2002 | Jestrabek-Hart | |
| 6,491,034 B1 | 12/2002 | Gunaratnam et al. | |
| 6,584,975 B1 | 7/2003 | Taylor | |
| 6,584,977 B1 | 7/2003 | Serowski | |
| 6,644,316 B2 | 11/2003 | Bowman et al. | |
| 6,651,663 B2 | 11/2003 | Barnett et al. | |
| 6,729,333 B2 | 5/2004 | Barnett et al. | |
| 6,823,865 B2 | 11/2004 | Drew et al. | |
| 6,851,428 B2 | 2/2005 | Dennis | |
| 7,152,602 B2 | 12/2006 | Bateman et al. | |
| 7,260,440 B2 | 8/2007 | Selim et al. | |
| 7,353,826 B2 | 4/2008 | Sleeper et al. | |
| 7,448,386 B2 | 11/2008 | Ho et al. | |
| 7,523,754 B2 | 4/2009 | Lithgow et al. | |
| 7,556,043 B2 | 7/2009 | Ho et al. | |
| 7,658,189 B2 | 2/2010 | Davidson et al. | |
| 7,708,017 B2 | 5/2010 | Davidson et al. | |
| 7,721,737 B2 | 5/2010 | Radney | |
| 7,810,497 B2 | 10/2010 | Pittman et al. | |
| 7,827,990 B1 | 11/2010 | Melidis et al. | |
| 7,942,148 B2 | 5/2011 | Davidson et al. | |
| 7,942,150 B2 | 5/2011 | Guney et al. | |
| 7,958,893 B2 | 6/2011 | Lithgow et al. | |
| 7,971,590 B2 | 7/2011 | Frater et al. | |
| 7,975,694 B2 | 7/2011 | Ho | |
| 8,042,539 B2 | 10/2011 | Chandran et al. | |
| 8,122,886 B2 | 2/2012 | Kwok et al. | |
| 8,127,764 B2 | 3/2012 | Ho et al. | |
| 8,136,524 B2 | 3/2012 | Ging et al. | |
| 8,136,525 B2 | 3/2012 | Lubke et al. | |
| 8,146,596 B2 | 4/2012 | Smith et al. | |
| 8,146,597 B2 | 4/2012 | Kwok et al. | |
| 8,251,066 B1 | 8/2012 | Ho | |
| 8,254,637 B2 | 8/2012 | Abourizk et al. | |
| 8,261,745 B2 | 9/2012 | Chandran et al. | |
| 8,267,089 B2 | 9/2012 | Ho et al. | |
| 8,291,906 B2 | 10/2012 | Kooij et al. | |
| 8,342,181 B2 | 1/2013 | Selvarajan et al. | |
| 8,353,294 B2 | 1/2013 | Frater et al. | |
| 8,397,728 B2 | 3/2013 | D'Souza et al. | |
| 8,439,035 B2 | 5/2013 | Dantanarayana et al. | |
| 8,573,212 B2 | 11/2013 | Lynch et al. | |
| 8,616,211 B2 | 12/2013 | Davidson et al. | |
| 8,622,057 B2 | 1/2014 | Ujhazy et al. | |
| 8,646,449 B2 | 2/2014 | Browsher | |
| 8,684,004 B2 | 4/2014 | Eifler | |
| 8,701,667 B1 | 4/2014 | Ho et al. | |
| 8,807,134 B2 | 8/2014 | Ho et al. | |
| 8,857,435 B2 | 10/2014 | Matula et al. | |
| 8,869,797 B2 | 10/2014 | Davidson et al. | |
| 8,910,626 B2 | 12/2014 | Matula et al. | |
| 8,931,484 B2 | 1/2015 | Melidis et al. | |
| 8,967,146 B2 | 3/2015 | Veliss et al. | |
| 8,978,653 B2 | 3/2015 | Frater et al. | |
| 8,997,742 B2 | 4/2015 | Moore et al. | |
| 9,010,330 B2* | 4/2015 | Barlow .............. | A61M 16/0816 128/205.25 |
| 9,010,331 B2 | 4/2015 | Lang et al. | |
| 9,044,564 B2 | 6/2015 | Dravitzki et al. | |
| 9,056,177 B2 | 6/2015 | Ho | |
| 9,067,033 B2 | 6/2015 | Davidson et al. | |
| 9,095,673 B2 | 8/2015 | Barlow et al. | |
| 9,149,594 B2 | 10/2015 | Kooij et al. | |
| 9,155,857 B2 | 10/2015 | Lalonde | |
| 9,174,018 B2 | 11/2015 | Ho et al. | |
| 9,220,860 B2 | 12/2015 | Davidson et al. | |
| 9,381,316 B2 | 7/2016 | Ng et al. | |
| 9,427,544 B2 | 8/2016 | Frater et al. | |
| 9,717,870 B2 | 8/2017 | Kwok et al. | |
| 9,737,678 B2 | 8/2017 | Formica et al. | |
| 9,757,534 B2 | 9/2017 | Lang et al. | |
| 9,764,107 B2 | 9/2017 | Grashow et al. | |
| 9,962,511 B2 | 5/2018 | Ng et al. | |
| 9,981,102 B2 | 5/2018 | Veliss et al. | |
| 9,993,606 B2 | 6/2018 | Gibson et al. | |
| 10,004,867 B2 | 6/2018 | Henry et al. | |
| 10,265,490 B2 | 4/2019 | Barlow et al. | |
| 10,265,492 B2 | 4/2019 | Amarasinghe et al. | |
| 10,369,318 B2 | 8/2019 | Barlow et al. | |
| 10,589,046 B2* | 3/2020 | Bearne .............. | A61M 16/0616 |
| 10,603,456 B2* | 3/2020 | Bearne .............. | A61M 16/0683 |
| 2002/0096178 A1 | 7/2002 | Ziaee | |
| 2003/0127101 A1 | 7/2003 | Dennis | |
| 2003/0196655 A1 | 10/2003 | Ging et al. | |
| 2005/0098183 A1 | 5/2005 | Nash et al. | |
| 2005/0199239 A1 | 9/2005 | Lang et al. | |
| 2006/0124131 A1 | 6/2006 | Chandran et al. | |
| 2006/0174887 A1 | 8/2006 | Chandran et al. | |
| 2006/0283461 A1 | 12/2006 | Lubke et al. | |
| 2007/0006879 A1 | 1/2007 | Thornton | |
| 2007/0125385 A1* | 6/2007 | Ho .................... | A61M 16/0605 128/206.26 |
| 2007/0144525 A1 | 6/2007 | Davidson et al. | |
| 2008/0041373 A1 | 2/2008 | Doshi et al. | |
| 2009/0038619 A1 | 2/2009 | Ho et al. | |
| 2009/0114229 A1 | 5/2009 | Frater et al. | |
| 2009/0277452 A1 | 11/2009 | Lubke et al. | |
| 2010/0132717 A1 | 6/2010 | Davidson et al. | |
| 2010/0192955 A1 | 8/2010 | Biener et al. | |
| 2010/0218768 A1 | 9/2010 | Radney | |
| 2010/0229872 A1 | 9/2010 | Ho | |
| 2010/0313891 A1 | 12/2010 | Veliss et al. | |
| 2011/0000492 A1 | 1/2011 | Veliss et al. | |
| 2011/0146685 A1 | 6/2011 | Allan et al. | |
| 2011/0162654 A1 | 7/2011 | Carroll et al. | |
| 2011/0253143 A1 | 10/2011 | Ho et al. | |
| 2011/0308526 A1 | 12/2011 | Ho et al. | |
| 2012/0067349 A1 | 3/2012 | Barlow et al. | |
| 2012/0080035 A1 | 4/2012 | Guney et al. | |
| 2012/0138063 A1 | 6/2012 | Eves et al. | |
| 2012/0234326 A1 | 9/2012 | Mazzone et al. | |
| 2013/0037033 A1 | 2/2013 | Hitchcock et al. | |
| 2013/0068230 A1 | 3/2013 | Jablonski | |
| 2013/0199537 A1* | 8/2013 | Formica ............ | A61M 16/0622 128/205.25 |
| 2013/0213400 A1 | 8/2013 | Barlow et al. | |

(56) References Cited

U.S. PATENT DOCUMENTS

| | | | |
|---|---|---|---|
| 2013/0220327 A1 | 8/2013 | Barlow et al. | |
| 2013/0319422 A1 | 12/2013 | Ho et al. | |
| 2013/0327336 A1 | 12/2013 | Burnham et al. | |
| 2014/0158136 A1 | 6/2014 | Romagnoli et al. | |
| 2014/0174444 A1 | 6/2014 | Darkin et al. | |
| 2014/0202464 A1 | 7/2014 | Lithgow et al. | |
| 2014/0216462 A1 | 8/2014 | Law et al. | |
| 2014/0224253 A1 | 8/2014 | Law et al. | |
| 2014/0261432 A1 | 9/2014 | Eves et al. | |
| 2014/0261435 A1 | 9/2014 | Rothermel | |
| 2014/0283822 A1 | 9/2014 | Price et al. | |
| 2014/0283831 A1 | 9/2014 | Foote et al. | |
| 2014/0283842 A1* | 9/2014 | Bearne | A61M 16/208 128/206.24 |
| 2014/0283843 A1 | 9/2014 | Eves et al. | |
| 2014/0326243 A1 | 11/2014 | Znamenskiy et al. | |
| 2014/0326246 A1 | 11/2014 | Chodkowski et al. | |
| 2014/0352134 A1 | 12/2014 | Ho | |
| 2015/0040911 A1 | 2/2015 | Davidson et al. | |
| 2015/0047640 A1 | 2/2015 | McCaslin | |
| 2015/0059759 A1 | 3/2015 | Frater et al. | |
| 2015/0105590 A1 | 4/2015 | Xiao | |
| 2015/0182719 A1 | 7/2015 | Grashow et al. | |
| 2015/0193650 A1 | 7/2015 | Ho et al. | |
| 2015/0246199 A1 | 9/2015 | Matula et al. | |
| 2016/0001029 A1 | 1/2016 | Bayer et al. | |
| 2016/0022944 A1 | 1/2016 | Chodkowski et al. | |
| 2016/0082214 A1* | 3/2016 | Barlow | A61M 16/06 128/206.24 |
| 2016/0184544 A1* | 6/2016 | Patel | A61M 16/0611 128/206.24 |
| 2016/0296720 A1 | 10/2016 | Henry et al. | |
| 2017/0000964 A1 | 1/2017 | Shafer | |
| 2017/0028153 A1 | 2/2017 | Judson et al. | |
| 2017/0080174 A1 | 3/2017 | Eves et al. | |
| 2017/0136200 A1 | 5/2017 | Matula | |
| 2017/0165444 A1 | 6/2017 | Rummery et al. | |
| 2017/0182273 A1 | 6/2017 | Ho | |
| 2017/0246411 A1 | 8/2017 | Mashal et al. | |
| 2017/0361048 A1 | 12/2017 | Moiler et al. | |
| 2017/0368286 A1 | 12/2017 | Grashow et al. | |
| 2018/0001044 A1 | 1/2018 | Stephens et al. | |
| 2018/0071475 A1 | 3/2018 | Howard et al. | |
| 2018/0099113 A1 | 4/2018 | Bell et al. | |
| 2018/0104430 A1 | 4/2018 | Ng et al. | |
| 2018/0140791 A1 | 5/2018 | Jones et al. | |
| 2018/0169367 A1 | 6/2018 | Chodkowski et al. | |

FOREIGN PATENT DOCUMENTS

| | | |
|---|---|---|
| DE | 3719009 | 12/1988 |
| DE | 4004157 | 4/1991 |
| DE | 4307754 | 4/1994 |
| EP | 1099452 | 5/2001 |
| EP | 1152787 A1 | 11/2001 |
| EP | 1258266 A1 | 11/2002 |
| EP | 1912693 | 4/2008 |
| EP | 2054114 | 5/2009 |
| EP | 2303379 | 4/2011 |
| EP | 2437837 | 4/2012 |
| EP | 2474335 A1 | 7/2012 |
| EP | 2501425 | 9/2012 |
| EP | 2624902 | 8/2013 |
| EP | 2708258 | 3/2014 |
| EP | 3164185 | 5/2017 |
| EP | 3254721 | 12/2017 |
| GB | 2385533 | 8/2003 |
| JP | 2011-512967 | 4/2011 |
| NZ | 536545 | 12/2006 |
| NZ | 547748 | 7/2010 |
| WO | WO 1998/034665 | 8/1998 |
| WO | WO 00/38772 | 7/2000 |
| WO | WO 2000/074758 | 12/2000 |
| WO | WO 2001/062326 | 8/2001 |
| WO | WO 2003/076020 | 9/2003 |
| WO | WO 2003/090827 | 11/2003 |
| WO | WO 2004/071565 | 8/2004 |
| WO | WO 2004/073778 | 9/2004 |
| WO | WO 2005/076874 | 8/2005 |
| WO | WO 2005/086943 | 9/2005 |
| WO | WO 2005/118040 | 12/2005 |
| WO | WO 2008/023028 | 2/2008 |
| WO | WO 2009/065368 | 5/2009 |
| WO | WO 2010/073138 | 7/2010 |
| WO | WO 2012/025843 | 3/2012 |
| WO | WO 2012/055886 | 5/2012 |
| WO | WO 2013/056389 | 4/2013 |
| WO | WO 2013/066195 | 5/2013 |
| WO | WO 2013/186654 | 12/2013 |
| WO | WO 2014/020468 | 2/2014 |
| WO | WO 2014/062070 | 4/2014 |
| WO | WO 2014/077708 | 5/2014 |
| WO | WO 2014/141029 | 9/2014 |
| WO | WO 2014/177972 | 11/2014 |
| WO | WO 2014/181214 | 11/2014 |
| WO | WO 2014/183167 | 11/2014 |
| WO | WO 2015/020535 | 2/2015 |
| WO | WO 2015/070289 | 5/2015 |
| WO | WO 2015/092621 | 6/2015 |
| WO | WO 2015/161345 | 10/2015 |
| WO | WO 2015/193821 | 12/2015 |
| WO | WO 2016/041008 | 3/2016 |
| WO | WO 2016/041019 | 3/2016 |
| WO | WO 2017/049361 | 3/2017 |
| WO | WO 2017/103724 | 6/2017 |
| WO | WO 2017/120643 | 7/2017 |
| WO | WO 2017/124152 | 7/2017 |
| WO | WO 2018/177794 | 10/2018 |

OTHER PUBLICATIONS

Lee, W. et al., Analysis of the Facial Measurements of Korean Air Force pilots for Oxygen Mask Design, Ergonomics, 56(9): 1451-64, 2013.

Zhuang, Z. et al., Facial Anthropometric Differences among Gender, Ethnicity and Age Groups, The Annals of Occupational Hygiene, 54(4):391-402, Jun. 2010.

Brad T Miller, B. et al., A Head-And-Face Anthropometric Survey of U.S. Respirator Users, Final Report by Anthrotech, May 28, 2004 [retrieved from internet on Oct. 28, 2016].

Los Alamos Scientific Laboratory Respirator and Research and Development Section, Selection of Respirator Test Panels Representative of U.S. Adult Facial Sizes, Dec. 1973 [retrieved from internet on Oct. 28, 2016].

International Search Report, PCT/IB2016/055212, dated Oct. 31, 2016, 5 pages.

Extended European Search Report for EP Appl. No. 16840943.1 dated Mar. 26, 2019 in 8 pages.

Amara View brochure, Respironics, 2015; product believed to have been available prior to Sep. 2015.

Australian Government IP Australia Examination Report No. 1 for Standard Patent Application No. 2016314605 dated May 1, 2020 in 4 pgs.

European Patent Office Examination Report, Application No. 16840943. 1-1122 dated Jun. 18, 2020 in 6 pgs.

* cited by examiner

| 1 | 2 | 3 | 4 | 5 | 6 | 7 | 8 |
|---|---|---|---|---|---|---|---|
| Scan | Nose Breadth | Nose Length | Pythag Length | Nasal Perimeter Creo | Nasal Perimeter Ratio | Calculated Size | Calculated Size Accuracy (%) |
| 112 | 49.5 | 26 | 35.89655276 | 88.1 | 2.454274665 | 93.00345067 | 94.72766802 |
| 77 | 37.3 | 26.9 | 32.73274355 | 78 | 2.382934993 | 84.80641915 | 91.97416985 |
| 25 | 28.7 | 19.7 | 24.37237165 | 64.1 | 2.630027185 | 63.14574773 | 101.5111901 |
| 130 | 38.2 | 17.7 | 26.0403533 | 70.6 | 2.711176734 | 67.46727825 | 104.6433202 |
| 68 | 45.5 | 26.4 | 34.85 | 95.3 | 2.734576758 | 90.29196418 | 105.5464912 |
| 1 | 44 | 24 | 32.55764119 | 85.7 | 2.632254576 | 84.352751 | 101.5971607 |
| | | | Average Ratio | | 2.590874151 | | |

PATIENT INTERFACES

INCORPORATION BY REFERENCE TO ANY PRIORITY APPLICATIONS

Any and all applications for which a foreign or domestic priority claim is identified in connection with the present application are hereby incorporated by reference herein and made a part of the present disclosure.

BACKGROUND

Field

The present disclosure relates to interface assemblies for respiratory therapy. In particular, the present disclosure relates to under-nose interface assemblies that do not cover the bridge of the user's nose.

Description of Related Art

In patients suffering from obstructive sleep apnea (OSA), muscles that normally keep the upper airway open relax during slumber to the extent that the airway is constrained or completely closed off, a phenomenon often manifesting itself in the form of snoring. When this occurs for a period of time, the patient's brain typically recognizes the threat of hypoxia and partially wakes the patient in order to open the airway so that normal breathing may resume. The patient may be unaware of these waking episodes, which may occur as many as several hundred times per session of sleep. This partial awakening may significantly reduce the quality of the patient's sleep, over time potentially leading to a variety of symptoms, including excessive daytime sleepiness, chronic fatigue, elevated heart rate, elevated blood pressure, weight gain, headaches, irritability, depression and anxiety.

Obstructive sleep apnea is commonly treated with the application of positive airway pressure (PAP) therapy. PAP therapy involves delivering a flow of gas to a patient at a therapeutic pressure above atmospheric pressure that will reduce the frequency and/or duration of apneas, hypopneas, and/or flow limitations. The therapy is often implemented by using a positive airway pressure device to deliver a pressurized stream of air through a conduit to a patient through a patient interface or mask positioned on the face of the patient.

One common type of patient interface assembly used with PAP therapy or other respiratory therapies involving the administration of gas includes a seal that contacts the bridge of the nose of a user of the interface assembly. The bride of the nose is sensitive to pressure applied by the seal of the interface assembly. More recently, interface assemblies have become available that do not contact the bridge of the nose. Such interface assemblies can be referred to as "under-nose" interface assemblies. A need exists to provide improved under-nose interface assemblies with improved comfort and/or sealing performance, or to provide the public with a useful choice.

SUMMARY

The disclosed under-nose masks are full face masks that seal below and around the nares of the user as opposed to full face masks that go over the nose bridge. Typically, over-the-nose full face masks sizing is determined by the length of the users face from the Nasion to the Menton/Sublabial. An aspect of the present disclosure involves the realization by the present inventors that under-nose full face mask sizing is significantly different than over-the-nose full face masks at least because the under-nose full face masks seal around the underside and nares of a user's nose. There is a large variation between nose shapes and sizes as well as variations in ethnicities ranging from short, long, wide, narrow, upward and downward facing as well as variations in nostril shapes/sizes. The combinations of all these variations make for a difficult task with regards to sizing. In addition to the variations described above, there are also many other facial dimensions to consider, such as face length, mouth width, head shape, among others.

The systems, methods and devices described herein have innovative aspects, no single one of which is indispensable or solely responsible for their desirable attributes. Without limiting the scope of the claims, some of the advantageous features will now be summarized.

In some configurations, a seal for an interface for use in providing positive pressure respiratory therapy includes a seal body configured to be fully positioned lower than a bridge of a nose of a face of a user and to provide an exposed bridge of the nose of the user. The mask seal includes a nasal region comprising a nasal opening. The mask seal includes a first paddle on a first side of the nasal region and a second paddle on a second side of the nasal region. The first paddle is configured to contact one side of the nose of the user and the second paddle is configured to contact the other side of the nose of the user. The nasal opening has one or more of the following: a nasal opening maximum linear distance between 5-10 mm, 6-8 mm or about 7.36 mm; a nasal opening-oral opening spacing linear distance between 10-15 mm, 11-13 mm or about 12.7 mm; a nasal opening length between 5-10 mm, 6-9 mm or about 7.2 mm; and a nasal opening width between 15-25 mm, 18-22 mm or about 19.7 mm.

In some configurations, a seal for an interface for use in providing positive pressure respiratory therapy includes a seal body configured to be fully positioned lower than a bridge of a nose of a face of a user and to provide an exposed bridge of the nose of the user. The mask seal includes a nasal region comprising a nasal opening. The mask seal includes a first paddle on a first side of the nasal region and a second paddle on a second side of the nasal region. The first paddle is configured to contact one side of the nose of the user and the second paddle is configured to contact the other side of the nose of the user. The nasal opening has one or more of the following: a nasal opening maximum linear distance between 5-10 mm, 6-8 mm or about 7.85 mm; a nasal opening-oral opening spacing linear distance between 10-15 mm, 11-13 mm or about 12.2 mm; a nasal opening length between 5-10 mm, 6-9 mm or about 7.1 mm; and a nasal opening width between 18-28 mm, 20-26 mm or about 23.75 mm.

In some configurations, a seal for an interface for use in providing positive pressure respiratory therapy includes a seal body configured to be fully positioned lower than a bridge of a nose of a face of a user and to provide an exposed bridge of the nose of the user. The mask seal includes a nasal region comprising a nasal opening. The mask seal includes a first paddle on a first side of the nasal region and a second paddle on a second side of the nasal region. The first paddle is configured to contact one side of the nose of the user and the second paddle is configured to contact the other side of the nose of the user. The nasal opening has one or more of the following: a nasal opening maximum linear distance between 3-7 mm, 4-6 mm or about 4.77 mm; a nasal opening-oral opening spacing linear distance between 9-14 mm, 10-13 mm or about 11.5 mm; a nasal opening length between 2-7 mm, 3-6 mm or about 3.85 mm; and a nasal opening width between 18-28 mm, 20-25 mm or about 22.3 mm.

In some configurations, a seal for an interface for use in providing positive pressure respiratory therapy includes a seal body configured to be fully positioned lower than a bridge of a nose of a face of a user and to provide an exposed bridge of the nose of the user. The mask seal includes a nasal region comprising a nasal opening. The mask seal includes a first paddle on a first side of the nasal region and a second paddle on a second side of the nasal region. The first paddle is configured to contact one side of the nose of the user and the second paddle is configured to contact the other side of the nose of the user. The nasal opening has one or more of the following: a nasal opening maximum linear distance between 2-6 mm, 3-5 mm or about 3.7 mm; a nasal opening-oral opening spacing linear distance between 7-12 mm, 8-11 mm or about 9.5 mm; a nasal opening length between 0.5-3 mm, 1-2 mm or about 1.6 mm; and a nasal opening width between 25-45 mm, 30-40 mm or about 32.9 mm.

In some configurations, the nasal opening has a height in a vertical plane when the seal is oriented vertically between 6-12 mm, 7-10 mm or about 8.63 mm.

In some configurations, the seal includes outwardly projecting portions on each side of the nasal region.

In some configurations, an interface includes a mask assembly comprising any one of the seals described above. The interface further includes a frame removably coupled to the mask assembly.

In some configurations, the interface further includes a pair of covers that are supported relative to the mask assembly such that each of the covers is positioned adjacent a portion of a respective one of the first and second paddles. The covers limit expansion of at least the portion of the first and second paddles.

In some configurations, the covers are supported by the frame. In some configurations, the covers are unitarily formed with the frame.

In some configurations, the covers are positioned adjacent only a portion of the paddles leaving a portion of the paddles exposed. In some configurations, a rearward portion of the paddles are left exposed by the covers.

In some configurations, the paddles cover a substantial entirety of a height of an adjacent portion of the paddles.

In some configurations, the paddles define a space therebetween, which exposes a portion of an upper portion of the mask seal.

In some configurations, the covers are formed as part of the mask shell and extend upward along the mask seal adjacent the paddles.

In some configurations, each of the paddles includes a support in the form of a suspension member, which assists in maintaining a desired shape of the paddles.

In some configurations, the suspension members include elongate, thickened areas of the mask seal that extend toward the frame from a patient side of the mask assembly. In some configurations, the suspension members are thicker than other portions of the mask seal in the paddles and the nasal region.

In some configurations, each of the suspension members is aligned with a respective one of the covers and is configured to transfer load from the seal to the covers via the suspension member.

In some configurations, the suspension members are connected to one another.

In some configurations, an interface system includes a frame that interchangeably supports at least two mask assemblies, each having a different one of the seals.

In some configurations, the interface system includes all four of the seals.

In some configurations, any one of the seals or interfaces includes any single one or combination of the features of described above.

In some configurations, an interface system is provided for providing positive pressure respiratory therapy to users, the system includes a mask frame; and a first seal and a second seal that are interchangeably mountable to the mask frame, the first seal having a first size and a second seal having a second size different than the first size. The first seal is configured to fit users having substantially the same nasal length and a smaller nasal width than users fitted by the second seal.

In some configurations, the interface system includes a third seal that is interchangeably mountable to the mask frame, the third seal having a third size that is different than the first and second sizes. The third seal is configured to fit users having substantially the same nasal width and a smaller nasal length than users fitted by the first seal.

In some configurations, the interface system includes a fourth seal that is interchangeably mountable to the mask frame, the fourth seal having a fourth size that is different than the first, second and third sizes. The fourth seal is configured to fit users having substantially the same nasal width and a smaller nasal length than users fitted by the second seal.

In some configurations, an interface system is provided for providing positive pressure respiratory therapy to users, the system includes a mask frame; and a first seal and a second seal that are interchangeably mountable to the mask frame, the first seal configured to fit a first range of nasal widths and a first range of nasal lengths, the second seal configured to fit a second range of nasal widths and a second range of nasal lengths.

In some configurations, the first and second ranges of nasal lengths are substantially equal.

In some configurations, the first and second ranges of nasal lengths overlap.

In some configurations, the interface system includes a third seal that is interchangeably mountable to the mask frame, the third seal configured to fit a third range of nasal widths and a third range of nasal lengths.

In some configurations, the first and third ranges of nasal widths are substantially equal.

In some configurations, the first and third ranges of nasal widths overlap.

In some configurations, the second and third ranges of nasal widths overlap.

In some configurations, the first and third ranges of nasal lengths overlap.

In some configurations, the second and third ranges of nasal lengths overlap.

In some configurations, the interface system includes a fourth seal that is interchangeably mountable to the mask frame, the fourth seal configured to fit a fourth range of nasal widths and a fourth range of nasal lengths.

In some configurations, the second and fourth ranges of nasal widths are substantially equal.

In some configurations, the second and fourth ranges of nasal widths overlap.

In some configurations, the second and fourth ranges of nasal lengths overlap.

In some configurations, the first and fourth ranges of nasal widths overlap.

In some configurations, the first and fourth ranges of nasal lengths overlap.

In some configurations, the third and fourth ranges of nasal lengths are substantially equal.

In some configurations, the third and fourth ranges of nasal widths overlap.

In some configurations, the third and third ranges of nasal lengths overlap.

In some configurations, a method for sizing seals that provide positive pressure respiratory therapy is provided. The method includes collecting data from a sample user population, the data including at least a first facial measurement and second facial measurement for each user; plotting the first and second facial measurements on a scatter plot, the scatter plot having a first axis corresponding to the first facial measurement and a second axis corresponding to the second facial measurement; and dividing the scatter plot into regions such that each region corresponds to a discrete seal size that is configured to fit users having facial measurements within a range along the first axis and a range along the second axis.

In some configurations, dividing the scatter plot into regions includes overlapping portions of two or more regions, wherein users having facial measurements within overlapping regions can be fitted to more than one seal size.

In some configurations, dividing the scatter plot into regions includes aligning at least one of edges and endpoints of two or more regions.

In some configurations, the first facial measurement includes a nasal width measurement and the second facial measurement includes a nasal breadth measurement.

In some configurations, the first facial measurement includes a nasal width measurement and the second facial measurement includes a mouth width measurement.

In some configurations, the first facial measurement includes a nasal width measurement and the second facial measurement includes a subnasal-to-sublabial length measurement.

In some configurations, a PAP kit is provided and includes an interface with a first seal having a first size and a second seal having a second size that is different than the first size. The first seal is configured to fit users within a first range of a first facial measurement and a first range of a second facial measurement, the second seal is configured to fit users within a second range of the first facial measurement and a second range of the second facial measurement.

In some configurations, a difference between average values of the first and second ranges of the first facial measurement is greater than a difference between average values of the first and second ranges of the second facial measurement.

In some configurations, a difference between average values of the first and second ranges of the first facial measurement is less than a difference between average values of the first and second ranges of the second facial measurement.

In some configurations, average values of each the first and second ranges of the first facial measurement are offset by a greater distance than average values of each the first and second ranges of the second facial measurement.

In some configurations, average values of each the first and second ranges of the first facial measurement are offset by a smaller distance than average values of each the first and second ranges of the second facial measurement.

In some configurations, the first and second ranges of the first facial measurement overlap.

In some configurations, the first and second ranges of the second facial measurement overlap.

In some configurations, the first facial measurement includes a nasal width measurement and the second facial measurement includes a nasal breadth measurement.

In some configurations, the first facial measurement includes a nasal width measurement and the second facial measurement includes a mouth width measurement.

In some configurations, the first facial measurement includes a nasal width measurement and the second facial measurement includes a subnasal-to-sublabial length measurement.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

DETAILED DESCRIPTION

Figure 1:
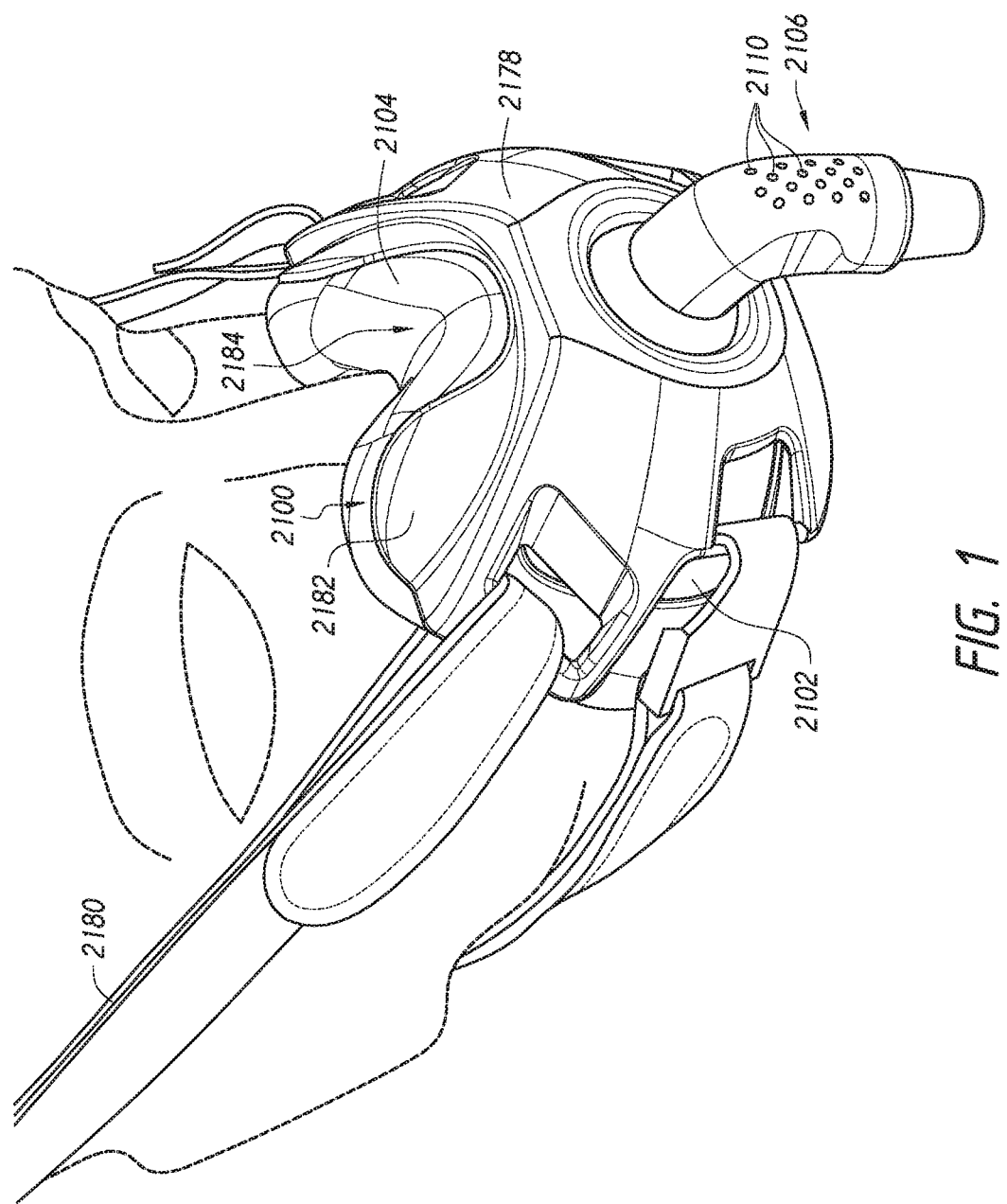
FIG. 1 is a front perspective view of an interface assembly having certain features, aspects and advantages of the present disclosure positioned on the head of a user.
Figure 2:
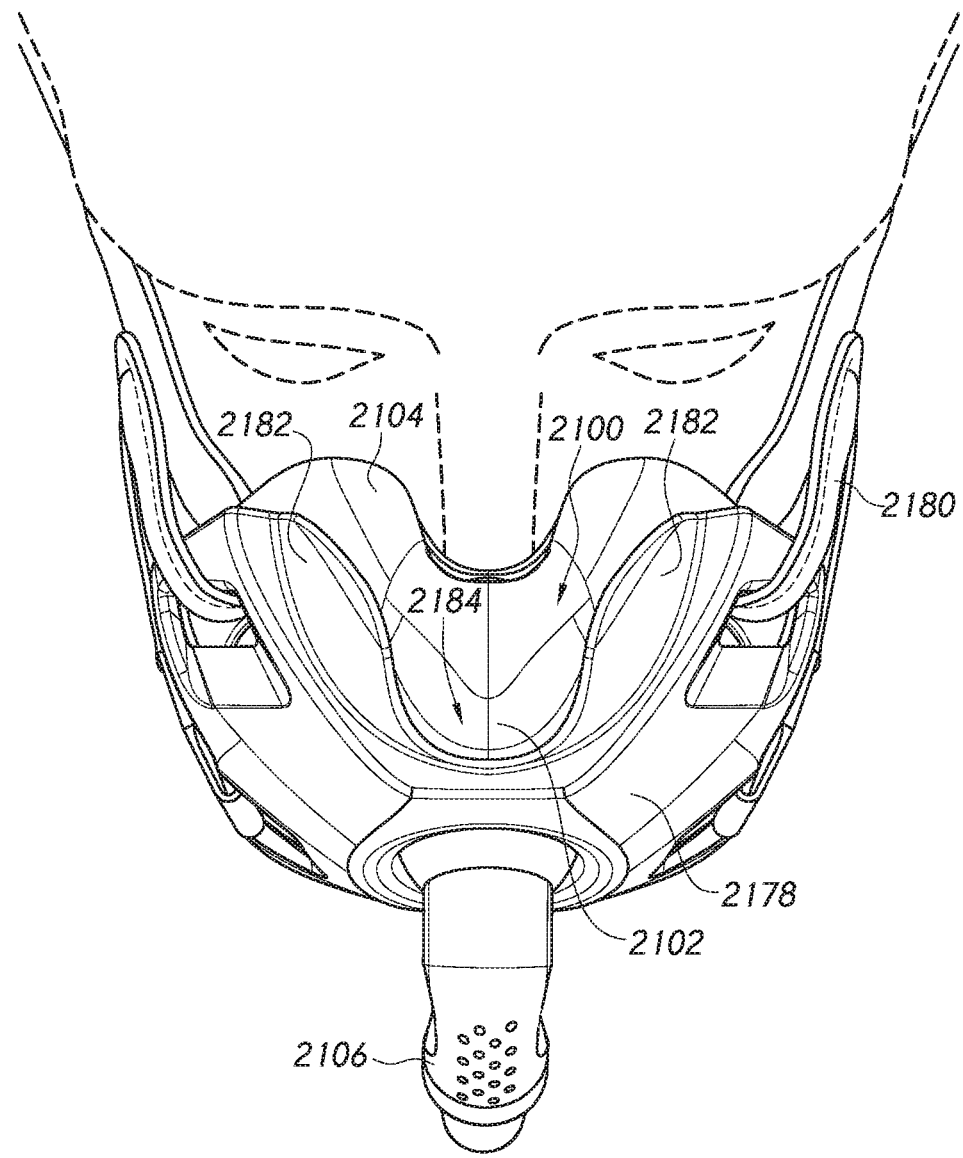
FIG. 2 is a top view of the interface assembly of FIG. 1 positioned on the head of a user.
Figure 3:
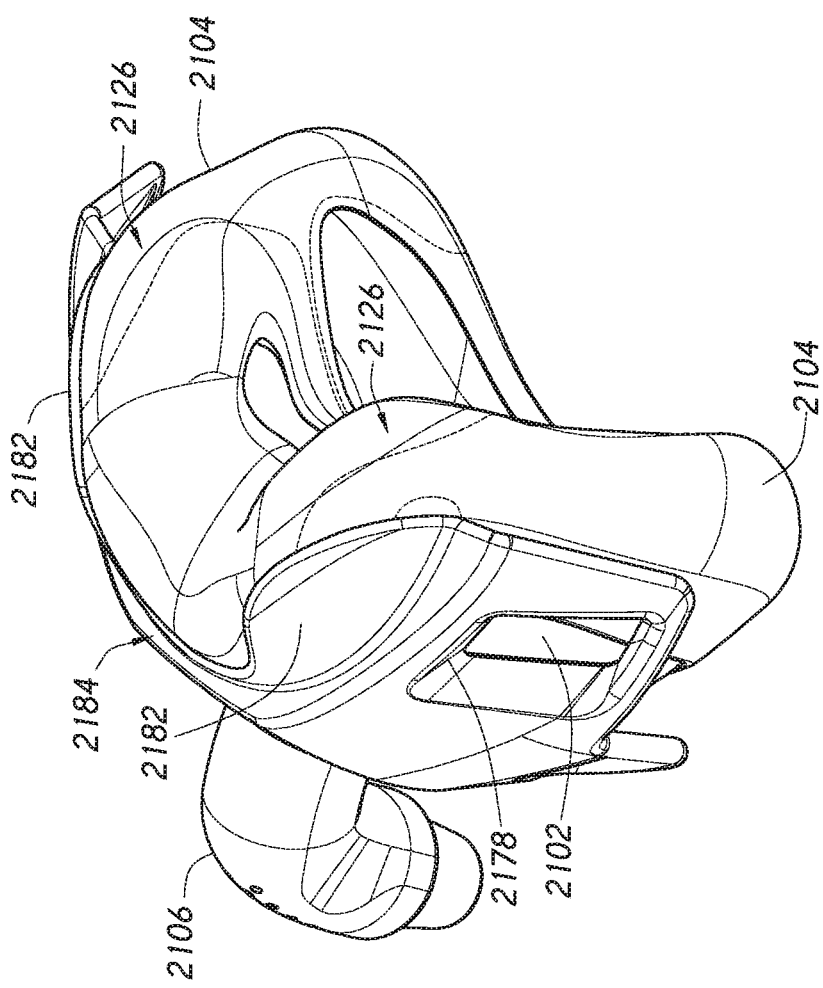
FIG. 3 is rear perspective view of an interface portion of the interface assembly of FIG. 1 separated from the user and without headgear.
Figure 4:
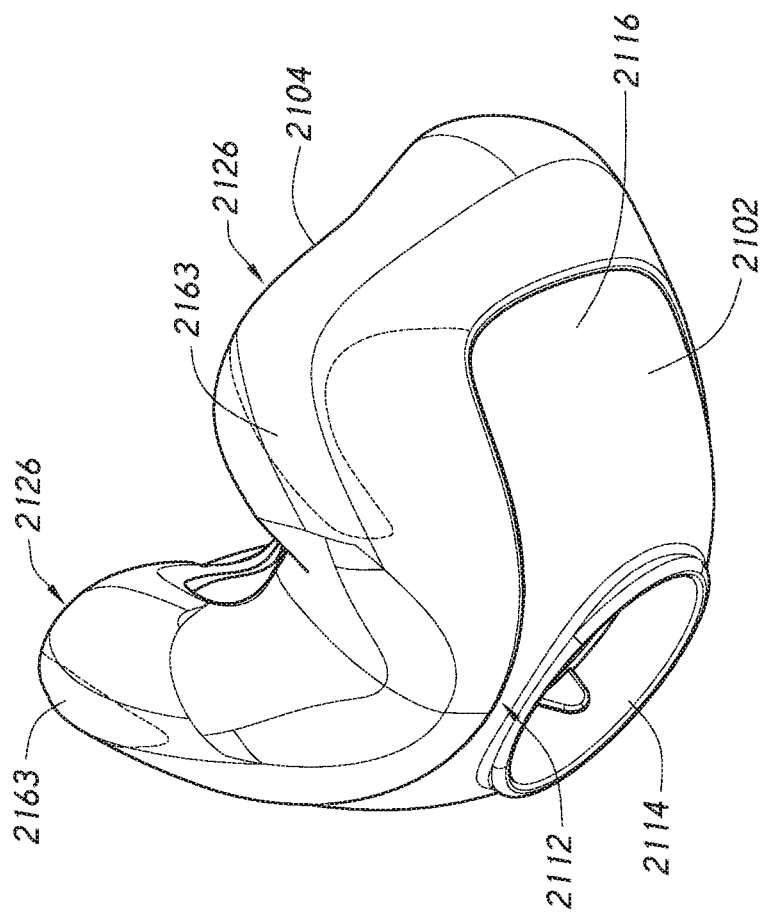
FIG. 4 is a front perspective view of a mask assembly of the interface assembly of FIG. 1.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made. Terms such as "front," "back," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

One or more of the embodiments described herein address issues with stability that can be experienced with face masks. In particular, at least some of the embodiments are directed toward patient interfaces, such as face masks, which seal below the bridge of the user's nose and around the nares. However, the embodiments disclosed herein could also be adapted to other full face masks (e.g., those that partially cover and/or seal on the bridge of the user's nose). Most full face masks have a forehead rest, headgear mount or 'T' piece which extends upwardly from the remainder of the mask and rests on the forehead and adds significant stability compared to those full face masks without 'T' pieces. Instability can cause nose tip or septum pressure and/or seal leaks due to forces applied by the breathing tube of the breathing circuit that is attached to the mask or other patient interface. This force is often referred to as "hose pull" and can originate from the breathing circuit or tube or from movement of the user.

The embodiments illustrated herein have no T piece and seal below the bridge of the nose, around the nares and under the nose. In at least some configurations, the interface or mask also seals around the user's mouth. The reduced foot print of an under-nose combined nasal and oral mask on the user's face compared to conventional full face masks that contact the nasal bridge and/or have a T piece can have an adverse effect on stability. Similarly, the reduced foot print of an under-nose nasal mask on the user's face compared to conventional nasal mask that contact the nasal bridge and/or have a T piece can also have an adverse effect on stability. Sealing around and below the nose in this manner can present challenges due to the variation seen in facial geometries from user to user. In some circumstances, even small movements of the seal can induce loss of contact of the seal with the user, which can result in leaks.

1. Mask Assembly

FIGS. 1-24 illustrate a mask assembly 2100 both in position on a face of a user and separated from the face of the user. The illustrated mask assembly 2100 is a combined nasal and oral mask, which can be referred to herein as a nasal-oral mask. The illustrated mask assembly 2100 is designed to seal under the nose of the user, along a portion of the face extending lateral to the nose, as well as around the mouth of the user. The mask assembly 2100 advantageously does not require contact with the bridge of the nose of the user. In the illustrated configuration, the mask assembly 2100 does not extend over the bridge of the nose of the user. More particularly, the illustrated mask assembly 2100 does not contact the bridge of the nose of the user. Even more particularly, the illustrated assembly 2100 does not contact a forward facing portion of the bridge of the nose of the user. In some configurations, the assembly 2100 does not contact the face in a region vertically higher than a generally horizontal plane extending along the lower edges of the eyes of the user. The mask assembly 2100 may or may not extend over the tip of the nose of the user. Thus, in some configurations, the mask assembly 2100 covers the tip of the nose. In some configurations, the seal of the mask assembly 2100 covers the tip of the nose. In some configurations, the illustrated mask assembly 2100 preferably does not enshroud the tip of the nose of the user. In some configurations or with some facial geometries, the tip of the nose of the user extends over the adjoining portion of the mask assembly 2100.

As illustrated, the mask assembly 2100 preferably is adapted to extend around and seal over the wing or alar of the nose, which flares out to form a rounded eminence around the nostril. The illustrated mask assembly 2100 is adapted to seal around the surfaces that define the opening to the nostril, which may include a portion or entirety of the fleshy external end of the nasal septum, sometimes called the columella. In some configurations, the mask assembly 2100 is adapted to extend upwardly to seal along at least a portion of the left and right dorsal side walls of the nose of the user. In some configurations, the mask assembly 2100 is adapted to extend upwardly along at least a portion of the left and right dorsal side walls without extending upwardly to the region of the bridge of the nose of the user. In some configurations, a primary sealing surface of the mask assembly 2100 contacts the underside of the nose of the user, possibly along with the upper lip and/or a transition region between the underside of the nose and the upper lip. A secondary sealing surface of the mask can contact the side surfaces of the nose of the user, possibly along with the cheeks at a location near the nose. Such primary and secondary sealing surfaces may not make contact with the face of all users; however, such an arrangement can provide a suitable seal with a relatively large range of facial geometries. The mask assembly 2100 preferably also seals around at least a portion of the user's mouth. The mask assembly 2100 may or may not be adapted to seal between the mouth and nose of the user.

As illustrated, the mask assembly 2100 comprises a mask support, such as a base, housing or shell 2102 (see, for example, FIG. 5), for example. A mask seal 2104 can be attached to the mask shell 2102 such that the mask shell 2102 provides some amount of support for the mask seal 2104. However, in other configurations, the mask seal 2104 may not include a support and may be adapted for direct assembly to another component of the associated interface assembly. In some configurations, the mask support 2102 can be substantially smaller than the illustrated shell. For example, the mask support 2102 can define an opening that allows the mask assembly 2100 to be attached to another component, such as a frame and/or conduit connector (e.g., elbow) and the mask support 2102 can be localized to the opening without providing direct support to other portions of the mask assembly 2100.

The mask assembly 2100 can be engaged with or otherwise supported by a frame 2178 that allows for connection to a head strap or headgear 2180 of any suitable arrangement. The mask assembly 2100 can be keyed to the frame 2178 to permit assembly in only the correct orientation. In some configurations, the head strap or headgear 2180 could be coupled directly to the mask assembly 2100 and the frame 2178 can be utilized for other purposes or omitted. A conduit connector 2106 can also be attached to the mask shell 2102, frame 2178 or otherwise supported relative to and adapted to communicate with an interior space of the mask assembly 2100. Together, the frame 2178 and the headgear 2180 can support the mask assembly 2100 in place on the user's face. Collectively, the mask assembly 2100, frame 2178 and headgear 2180 can be referred to as an interface assembly. The mask assembly 2100 or the mask assembly 2100 in combination with the frame 2178 can be referred to as an interface.

The illustrated conduit connector 2106 can be connected to the frame 2178 and/or shell 2102 in any suitable manner, including but not limited to any manner discussed elsewhere within this application. For example, but without limitation, the connector 2106 can be connected to the shell 2102 such that the connector 2106 can swivel, pivot or rotate relative to the shell 2102 about a single axis or about multiple axes. In some configurations, the connector 2106 can define a portion of a ball joint with the frame 2178 and/or mask shell 2102, for example but without limitation, defining the other portion. The ball joint can have any suitable configuration. The connector 2106 facilitates connection to a gases conduit, such as a supply conduit or the like for the supply of pressurized breathing gases to an interior of the mask assembly 2100. Any suitable connector 2106 can be used, which in some cases can include a swivel or rotational coupling that permits relative rotation between the connector 2106 and the gases conduit.

In the illustrated configuration, the connector 2106 comprises an elbow, such as a polycarbonate elbow for example but without limitation, that contains a vent. In the illustrated arrangement, the vent comprises bias flow holes 2110. However, the vent could comprise other geometries or arrangements, such as slots or a controlled leak between components, for example. The vent could also comprise diffuser materials to reduce noise and/or draft. The bias flow holes 2110 are a collection of orifices that are configured to exhaust air and flush CO2 to reduce the likelihood of rebreathing expired carbon dioxide by the user. While the bias flow holes 2110 are shown exclusively on the connector 2106, in some configurations, the bias flow holes 2110 can be provided on the mask shell 2102, on the mask seal 2104 or on any combination of the connector 2106, the shell 2102 and the seal 2104 or on any other component of the interface assembly or associated breathing circuit. The bias flow holes 2110 can have any suitable cross-section and can be cylindrical, hour-glass shaped, tapered in either direction, fully or partially tapered, fully or partially cylindrical, contoured to vary in cross-section or the like.

The mask shell 2102 provides a support structure of sorts for the mask assembly 2100 in general and for the mask seal 2104 more specifically. The mask shell 2102 can be formed from any suitable material. In some configurations, the mask shell 2102 is formed from a fairly rigid material. In some configurations, the mask shell 2102 is formed from a plastic material, such as a polycarbonate material. In some configurations, the mask assembly 2100 can comprises a mask seal that includes a mask seal clip that is separate from but attachable to a mask shell. In such a configuration, the mask seal clip would connect the mask seal 2104 to the mask shell 2102. In such configurations, the mask seal and mask seal clip can be formed separately and secured together or the mask seal and the mask seal clip can be integrated into a single component. In some configurations, the mask seal can be overmolded onto the mask seal clip and, in some configurations, the mask seal 2104 can be overmolded directly onto the mask shell 2102, which can comprise chemical and/or mechanical overmolding, for example.

In some configurations, the mask shell 2102 comprises a substantial portion of a forward wall of the mask assembly 2100. Such an arrangement provides an advantageous level of support to the mask seal 2104. For example, the mask shell 2102 comprises a substantial portion of an oral portion of the forward wall of the mask assembly 2100. In some configurations, the mask shell 2102 is generally limited to the oral portion of the mask assembly 2100 and does not extend into the nasal portion of the mask assembly 2100, at least to any significant extent. Such an arrangement can provide support to the mask seal 2104, while advantageously permitting movement or deformation of the nasal portion of the mask seal 2104. In the illustrated configuration, the mask shell 2102 sweeps rearward from a central portion 2112 toward opposing side portions 2116. The central portion 2112 contains an aperture 2114 for receiving the connector 2106. The mask shell 2102 can have a generally or substantially constant height throughout the central portion 2112 and opposing side portions 2116. In other arrangements, the mask shell 2102 can vary in height, such as by forming a shape that generally mimics the frontal shape of the mask seal 2104. The height of the mask shell 2102 can be substantially equal to a height of the oral portion of the mask seal 2104. A width of the mask shell 2102 can comprise a significant portion of the overall width of the oral portion of the mask assembly 2100, such as at least about three-quarters of the overall width of the oral portion of the mask assembly 2100. Such an arrangement of the mask shell 2102 can provide reinforcement to the central and lateral portions of the mask seal 2104. In some configurations, the mask shell 2102 could be minimal, such as an annular support ring or frame, for example.

The mask seal 2104 is designed to seal against the face of the user. The mask seal 2104 preferably is formed of a soft material, such as silicone, for example but without limitation. In some configurations, at least portions of the mask seal 2104 can be textured to improve comfort to the user. For example, in some configurations, at least portions of the mold used to form the illustrated mask seal 2104 can be bead blasted to provide a surface texture in at least the regions of the mask seal 2104 that will contact the skin of the user. Other techniques for texturing one or more surface of the mask seal 2104 can be used. In some configurations, it may be desirable to avoid surface texturing and provide at least the face-contacting surfaces of the mask seal 2104 with a smooth surface texture, which may increase grip of the mask seal 2104 on the user's face and improve sealing characteristics.

As described above, the illustrated mask seal 2104 comprises a nasal-oral mask seal and, therefore, comprises at least one oral opening 2122 and at least one nasal opening 2124. In some configurations, the mask seal 2104 can comprise a combined oral-nasal opening. In some configurations, the mask seal 2104 can comprise more than one nasal opening 2124. In some configurations, the mask seal 2104 can comprise nasal openings 2124 defined within superstructures, such as pillows, prongs or the like. In some configurations, the nasal opening 2124 can be defined by a nasal cushion or insert, which can be overmolded or otherwise secured to a base structure of the mask seal 2104. An example of such an arrangement is disclosed in Applicant's publication no. WO 2014/062070, the entirety of which is incorporated by reference herein.

The at least one oral opening 2122 and the at least one nasal opening 2124 preferably communicate with a single chamber 2125 that is defined within the mask assembly 2100. The chamber 2125 of the illustrated mask assembly 2100 is at least partially defined by the mask shell 2102 and the mask seal 2104. The at least one oral opening 2122 is substantially opposed to the aperture 2114 that receives or communicates with the connector 2106. The at least one nasal opening 2124 can be vertically above the at least one oral opening 2122. The at least one nasal opening 2124 can be positioned between the aperture 2114 for the connector 2106 and the at least one oral opening 2122 in a fore-aft direction of the mask assembly 2100. The at least one nasal opening can have an axis that is inclined relative to vertical and that, in some arrangements, can generally extend through the aperture 2114 for the connector 2106.

The mask seal 2104 preferably comprises a pair of paddles 2126 that extend upward above an upper surface 2130 (FIG. 8) of a central portion of the mask seal 2104. The upper surface 2130 can define a line that lies along a central surface of the nasal surface of the mask seal 2104 in a fore-aft direction. Such a line extends generally along the nasal septum in a direction away from the user's face. The paddles 2126 are configured to extend upward alongside, and in some configurations above, the nares. The paddles 2126 can contact the edges of the nares and/or sides of the nose. The paddles 2126 or portions of the mask seal 2104 between the paddles 2126 may or may not cover the tip of the user's nose. As described herein, preferably the mask seal 2104 does not contact the bridge of the user's nose.

In some configurations, the paddles 2126 each comprise an air pocket that is in direct fluid communication with the air path through the mask assembly 2100 from the connector 2106 to the at least one nasal opening 2124 and the at least one oral opening 2122. The paddles 2126 can be configured to expand in volume in response to elevated pressure within the mask seal 2104 and/or flex inwardly to accommodate various facial and nasal geometries and assist in creating a sealed contact with the user's face. Expansion of the paddles 2126 can assist in sealing against the face of the user, especially along the varying contours on and around the user's nose. Inward flexing of the paddles 2126 allows the central portion (e.g., upper surface 2130) to move downward with less restriction or less stretching of the material of the mask seal 2104 so that the mask seal 2104 can better conform to various nasal geometries.

The height of the paddles 2126 above the upper surface 2130 can be selected to provide a desired balance between stability of the mask seal 2104 on the user's face (e.g., vertical stability) and being able to accommodate a range of nasal geometries or reducing visual disruption by the paddles 2126. In general, higher paddles 2126 tend to provide additional vertical stability of the mask assembly 2100, while lower paddles 2126 tend to provide a better fit of a wider range of users and result in less visual disruption. In some configurations, the paddle height 2126 is between about 10 mm and about 30 mm or between about 15 mm and about 25 mm. In some configurations, the paddle height 2126 is between about 15 mm and about 22 mm or between about 18 mm and about 20 mm, including an value or sub-range within the above-described ranges. In some configurations, the paddle height is about 18.5 mm.

The illustrated mask seal 2104 of the mask assembly 2100 comprises a fairly complex range and configuration of thicknesses, as shown in FIGS. 7-21. The thicknesses are varied to take advantage of or provide different characteristics in different regions of the illustrated mask seal 2104. For example, the thicknesses in the various regions can be selected to address a desired characteristic for that region and/or the mask seal 2104 as a whole. Such characteristics can include, for example, allowing the mask seal 2104 to conform to the facial geometry of the user to enhance sealing properties or comfort, supporting the shape of the mask seal without significant internal gas pressure to facilitate fitment and/or in response to internal gas pressure and/or external pressure (e.g., caused by headgear forces) or providing strength or durability.

FIGS. 7-10 illustrate views of the mask seal 2104 with regions of different thickness outlined. In general, the outer surface of the mask seal 2104 defines a relatively smoothly shaped or curved surface without abrupt changes in direction. The different thicknesses are created by changes in wall thickness that are apparent on or created by changes in shape of an interior surface of the mask seal 2104, as illustrated by the sectional views of FIGS. 12-21. FIGS. 7-10 illustrate differences in thicknesses of the mask seal 2104, such as those in the above-described regions or portions. In some configurations, support structures 2163 for the paddles are thicker than a nasal region 2168 and an upper front portion 2150. In some configurations, a relatively abrupt transition in thickness occurs between the nasal region 2168 and upper front portion 2150 and the supports 2163. In contrast, transitions in thickness between outer peripheral portions 2162, the supports 2163 and an upper rear portion 2156 are more gradual. In addition, in at least some configurations, transitions in thickness between the outer peripheral portions 2162, the upper rear portion 2156 and the oral region 2166 are relatively gradual. The various portions of the mask seal 2104 are described further below.

To reduce the incidence of wrinkling of at least some of the face contacting regions of the mask seal 2104 during use, it has been found that the outer peripheral portions 2162 of the mask seal 2104, which are generally adjacent to some or all of the face contacting portions of the mask seal 2104, provide desirable performance when the outer peripheral portions 2162 are fairly rigid or relatively rigid compared to adjacent portions or other portions of the mask seal 2104. In the illustrated arrangement, the outer peripheral portions 2162 extend along the generally vertically extending portions on the rear of the mask seal 2104 and wrap slightly inward at a bottom of the rear of the mask seal 2104. In addition, the outer peripheral portions 2162 wrap from a rear facing side of the mask seal around to at least a portion of a laterally facing side of the mask seal 2104.

In the illustrated arrangement, the outer peripheral portions 2162 are located on each lateral side of the oral opening 2122. In some configurations, the outer peripheral portions 2162 extend along an entire height of the oral opening 2122. Upper ends of the outer peripheral portions 2162 can extend at least to about an upper end of the oral opening 2122. Lower ends of the outer peripheral portions 2162 can extend below a lower end of the oral opening 2122. As described above, in some configurations the outer peripheral portions 2162 wrap inwardly below the oral opening 2122 such that portions of the outer peripheral portions 2162 are positioned vertically below portions of the oral opening 2122.

The relatively increased thickness of the outer peripheral portions 2162 can assist in resisting or preventing collapse of the mask seal 2104 in the absence of significant internal gas pressure to facilitate fitment and provide feedback to the user, such as in response to applied forces (e.g., headgear forces). The outer peripheral portions 2162 can help maintain the curved shape of the lateral sides of the mask seal 2104 and/or help maintain a separation between a rear wall of the mask seal 2104 (defining a face contacting surface) and a front wall of the mask seal 2104 at least in response to forces experience during normal use. In some configurations, the thickness of a portion or an entirety of the outer peripheral portions can be between about 1.0 mm and about 2.0 mm. In the illustrated configuration, a portion or an entirety of the outer peripheral portions 2162 preferably have a thickness of about 1.5 mm. The thicknesses of the outer peripheral portions 2162 can be consistent or varied within a boundary of the outer peripheral portion 2162.

The illustrated mask seal 2104 also comprises the oral region 2166. The oral region 2166 in the illustrated mask seal 2104 extends along at least a portion of the oral opening 2122. Preferably, the oral region 2166 extends along at least a lower portion of the oral opening 2122. The oral region 2166 can extend along at least the sides and the bottom of the oral opening 2122. In the illustrated arrangement, the oral region 2166 circumscribes the oral opening 2122. The oral region 2166 can comprise a relatively thin band that surrounds some or all of the oral opening 2122, such as the sides and upper portion in the illustrated arrangement. The illustrated oral region 2166 comprises a lower thickened band portion that extends downwardly away from the oral opening 2122 and can extend toward or to a lower edge of the mask seal 2104. The lower thickened portion of the oral region 2166 can contact the area below the lower lip of the user and can allow the mask seal 2104 to accommodate a range of chin geometries. The lower thickened portion of the oral region 2166 can define a curved edge opposite the edge adjacent the oral opening 2122.

The oral region 2166 provides a softer region that contacts the face. Accordingly, the oral region 2166 can have a thinner cross-section than the outer peripheral portions 2162 and/or other regions of the mask seal 2104. In some configurations, the oral region 2166 has the smallest thickness or is among the smallest thicknesses of the mask seal 2104. For example, a portion or an entirety of the oral region 2166 can have a thickness of between about 0.2 mm and about 0.5 mm. In the illustrated configuration, the thickness of a portion or an entirety the oral region 2166 is about 0.3 mm. The thickness of the oral region 2166 can be consistent or variable within the oral region 2166.

The mask seal 2104 can also include the nasal region 2168 located near the nasal opening 2124. The nasal region 2168 can surround a portion or an entirety of the nasal opening 2124. In the illustrated arrangement, the nasal region 2168 surrounds an entirety of the nasal opening 2124 and has side portions that are located at least partially on the paddles 2126. The nasal region 2168 can wrap from the rear of the mask seal 2104 toward the front. In the illustrated arrangement, the nasal region 2168 is radially spaced from the nasal opening 2124. Given a desire to gently seal against the lower portion of the nose, the nasal region 2168 in the illustrated configuration has a fairly small thickness. In some configurations, the nasal region 2168 has the smallest thickness of the mask seal 2104 or is equal to or among the smallest thickness of the mask seal 2104. For example, a portion or an entirety the nasal region 2168 can have a thickness that is equal to or slightly larger than the thickness of the oral region 2166. In some configurations, the thickness of a portion or an entirety the nasal region 2168 is between about 0.3 mm and about 0.5 mm or 0.6 mm. In some configurations, the thickness of a portion or an entirety the nasal region 2168 is about 0.3 mm. The thickness of the nasal region 2168 can be consistent or variable within the nasal region 2168. A portion or an entirety of the nasal region 2168 could have a thickness that is less than about 0.3 mm. For example, the thickness could be as low as about 0.15 mm. However, it has been determined that lower thicknesses can result in or increase the likelihood of creasing of the nasal region 2168 for some facial geometries and/or under some operational gas pressures. Keeping the thickness above about 0.3 mm in a substantial portion or an entirety of the nasal region 2168 can reduce the incidence of creasing over a substantial range of operational pressures, which may comprise an entire range of normal operating pressures.

The mask seal 2104 can also include the upper front portion 2150 that is positioned above the mask shell 2102. In the illustrated arrangement, the upper front portion 2150 extends in a lateral direction across the front of the mask seal 2104 between the mask shell 2102 and the nasal region 2168 in a vertical direction. The upper front portion 2150 can extend any suitable distance across the mask seal 2104, such as along a substantial entirety of a width of the mask seal 2104 or the width of the mask seal 2104 at least at the location of the upper front portion 2150. An upper edge of the upper front portion 2150 can be curved and the sides of the upper front portion 2150 can have a greater height than a central portion of the upper front portion 2150 such that the central portion defines a valley of the upper front portion 2150. In some configurations, the sides of the upper front portion 2150 can extend into the portion of the mask seal 2104 defining the paddles 2126. In some configurations, a lower edge of the upper front portion 2150 can be generally linear and extend in a horizontal or lateral direction. The lower edge of the upper front portion 2150 can have generally the same shape as an upper edge of the mask shell 2102.

The upper front portion 2150 preferably has a fairly small thickness to promote flexibility of the upper front portion 2150. That is, preferably, the upper front portion 2150 is able to flex, fold or otherwise deform in response to pressure acting on other portions of the mask seal 2104, such as downward pressure on the nasal region 2168, for example. Such an arrangement can assist the mask seal 2104 in conforming to different facial geometries of possible users. In addition, such an arrangement can facilitate expansion or ballooning of the paddles 2126, at least in the absence of external restraints on such expansion. In some configurations, the upper front portion 2150 has the smallest thickness of the mask seal 2104 or is equal to or among the smallest thickness of the mask seal 2104. For example, a portion or an entirety the upper front portion 2150 can have a thickness that is equal to the thickness of one or both of the oral region 2166 and the nasal region 2168. In some configurations, the thickness of a portion or an entirety the upper front portion 2150 is between about 0.2 mm and about 0.5 mm. In some configurations, the thickness of a portion or an entirety the upper front portion 2150 is about 0.3 mm. The thickness of the upper front portion 2150 can be constant or variable within the upper front portion 2150. The thickness of the upper front portion 2150 could be smaller or larger depending on the desired properties of the mask seal 2104, such as compliance of the nasal region 2168.

The mask seal 2104 can also comprise the support structures or supports 2163 for the paddles 2126, which can be in the form of suspension members or springs that provide mechanical rigidity and structure to hold the shape of the paddles 2126 when the mask seal 2104 is worn by a user. The supports 2163 can comprise thickened regions of the seal material. The supports 2163 preferably are sized, shaped and/or otherwise configured to transfer force from a rearward or user-contacting surface of the paddles 2126 toward or to a forward surface of the paddles 2126. In some configurations, the interface can include a support portion or cover for the paddles 2126 and the supports 2163 can transfer force from the rearward surface of the paddles 2126 to the forward surface or other portion of the paddles 2126 or mask seal 2104 that contacts or faces the support portion or cover. In some configurations, the supports 2163 can transfer force from the rearward surface of the paddles 2126 toward or to another support portion of the mask seal 2104 (e.g., the mask shell 2102) or interface. The supports 2163 can resist or prevent collapse of the paddles 2126 or other related or adjacent portions of the mask seal 2104 to facilitate fitment and provide feedback to the user, such as in response to applied forces (e.g., headgear forces). In some configurations, the supports 2163 can resist or prevent collapse of the paddles 2126 or other related or adjacent portions of the mask seal 2104 in the absence of significant internal gas pressure. The supports 2163 can help maintain the shape of the paddles 2126 of the mask seal 2104 and/or help maintain a separation between a rear wall of the mask seal 2104 (defining a face contacting surface) and a front wall of the mask seal 2104 at least in response to forces experience during normal use. In addition, the supports 2163 can provide support to the nasal region or nasal seal portion 2168. In particular, the supports 2163 can provide structure to and inhibit or prevent creasing, wrinkling or collapsing of the nasal seal portion 2168 and/or the upper front portion 2150. As described above, the nasal seal portion 2168 and/or the upper front portion 2150 preferably are relatively thin to permit these portions of the mask seal 2104 to conform to the user's nose. The relatively thin nasal seal portion 2168 and/or the upper front portion 2150 can expand and seal around the user's nose. The supports 2163 provide rigid portions or elements of the seal 2104 adjacent or near the relatively thin nasal seal portion 2168 and/or the upper front portion 2150 to inhibit or prevent collapse when a user engages his or her nose into the mask assembly 2100. The upper rear portion 2156 can assist in preventing collapse of the nasal seal portion 2168 and/or the upper front portion 2150.

In some configurations, the supports 2163 help to reduce the likelihood of wrinkling or creasing of the face contacting portions of the paddles 2126 during use while allowing the laterally inner portions to be as thin as desired within practical limitations, such as those described above. The supports 2163 can assist in inhibiting or preventing collapse of the paddles 2126 or maintaining a desired shape of the paddles 2126. For example, the supports 2163 can assist in maintaining a desired fore-aft shape of the paddles 2126 and/or a lateral or side-to-side shape of the paddles 2126. The level of support provided can vary in different directions. In some configurations, the supports 2163 could be formed as separate portions or separate components from the seal material and could be the same or a different material. Such separate supports 2163 could be coupled to the paddles 2126 or other portion of the mask seal 2104 if desired. The supports 2163 disclosed herein can be particularly useful in under-nose type mask assemblies, including both nasal masks and combined nasal-oral masks. However, the supports 2163 can also be utilized in other types of mask assemblies or interfaces, including those that cover, contact or seal against the bridge of the user's nose and/or include a T piece or other type of forehead support, for example and without limitation. The supports 2163 can be utilized, or modified for use, in any locations of an interface in which support against collapsing and/or support against overexpansion may be desirable. Such locations can be at or near the portion of the seal that contacts or extends alongside the user's nose or can be at other locations.

In the illustrated arrangement, at least a portion of the supports 2163 extend generally in a fore-aft direction along the paddles 2126. In particular, the supports 2163 can extend along the upper edge of the paddles 2126 or the region or ridge that joins the laterally outer surface portion and the laterally inner surface portion along the upper edges of the paddles 2126. The supports 2163 can extend along a portion of the sides of the nasal region 2168. The supports 2163 can comprise a generally thin, elongate shape. Viewed from above, the supports 2163 can comprise a generally triangular shape with a base of the triangle positioned rearwardly of the top or point of the triangle. Other shapes are possible to achieve a desired level of support or for other design considerations, such as the desired shape(s) of adjacent or nearby structures. The supports 2163 can have additional portions to provide other levels of support or to provide support in other directions. For example, the supports 2163 could connect to one another, such as along one or both of the forward or rearward sides of the nasal opening 2124. In some configurations, the supports 2163 could extend completely through the paddles 2126, such as to the mask shell 2102, for example.

The supports 2163 can have a different thickness than other portions of the paddles 2126 and can have a greater thickness than other portions of the paddles 2126. In some configurations, the supports 2163 can have the largest thickness or among the largest thicknesses of the mask seal 2104. In some configurations, a portion or an entirety of the supports 2163 can have a thickness of between about 1.5 mm and about 3.5 mm. In the illustrated configuration, a portion or an entirety of the supports 2163 can have a thickness of about 2.5 mm. The thickness of the supports 2163 can be constant or variable.

Figure 19:
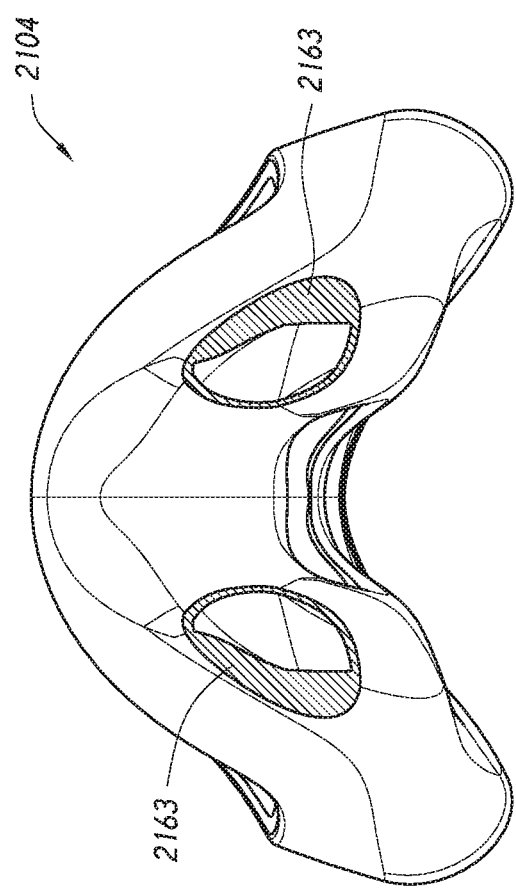
FIG. 19 is a sectional view of the mask seal taken along line 19-19 of FIG. 11.
Figure 20:
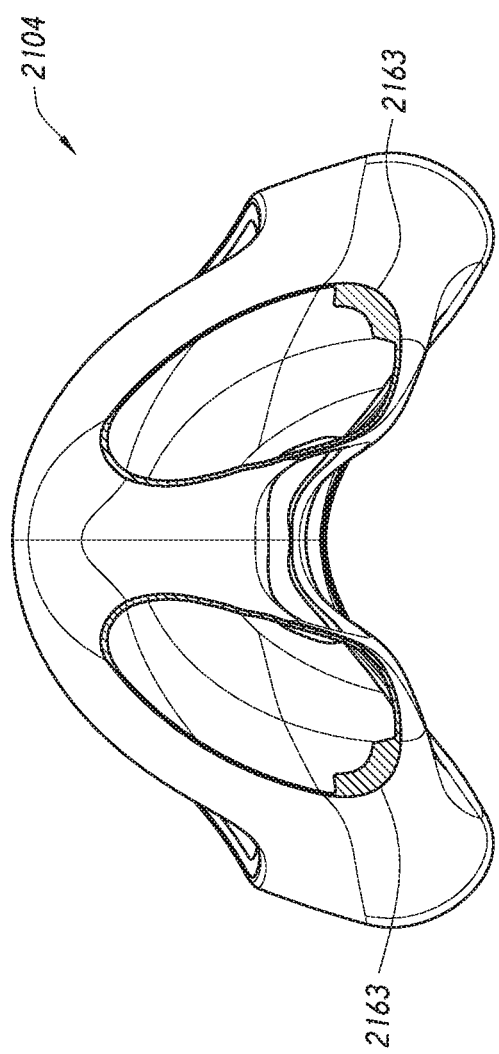
FIG. 20 is a sectional view of the mask seal taken along line 20-20 of FIG. 11.
Figure 21:
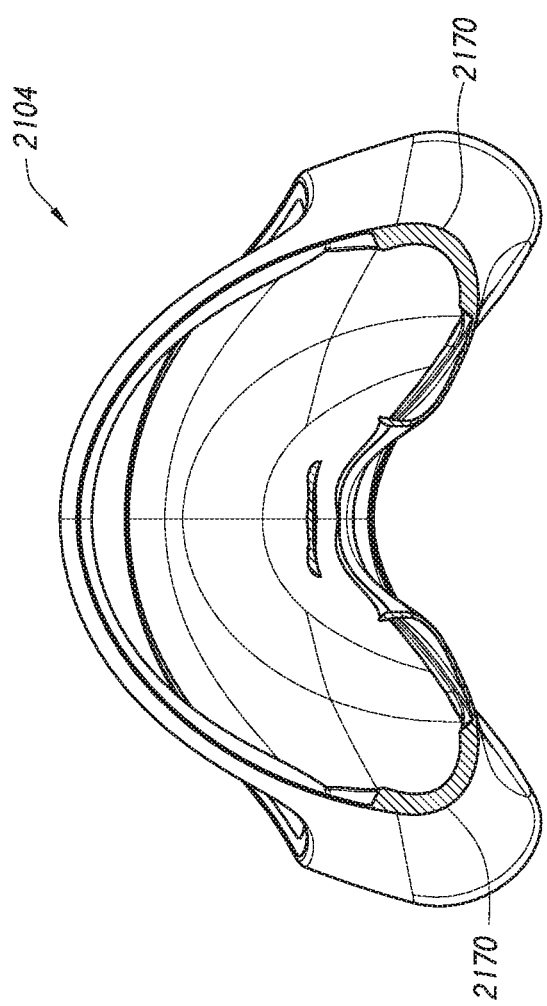
FIG. 21 is a sectional view of the mask seal taken along line 21-21 of FIG. 11.

With reference to FIGS. 19-21, portions of the mask seal 2104 incorporating the paddles 2126 are shown in cross section. As illustrated therein, and described above, the paddles 2126 can have a relatively thin cross section, at least in those sections other than the supports 2163. In some configurations, the paddles 2126 can be formed at least in part with a cross section sufficiently thin to allow controlled inflation or controlled expansion at typical treatment pressures (e.g., about 3 to about 25 cmH2O). In some configurations, such a thickness might be equal to or lower than about 0.5 or 0.6 mm, equal to or lower than 0.3 mm or equal to or lower than about 0.2 mm depending upon the particular location within the paddle 2126 and/or the material used. In some configurations, the portion of the paddles 2126 that will contact the face comprises a generally constant cross-sectional thickness. As illustrated in FIGS. 16-21, the thickened portions can continue to extend below the supports 2163 of the paddles 2126, such as into a region of the mask seal 2104 below the paddles 2126.

In some configurations, the mask seal 2104 comprises an upper rear portion 2156 that extends in a lateral direction along a rear surface of the mask seal 2104 between the nasal region 2168 and the oral region 2166. In the illustrated arrangement, the upper rear portion 2156 is an elongated strip region of the mask seal 2104 defined by an internal rib. In some configurations, the ends of the upper rear portion 2156 can have a greater height or vertical dimension than a center portion of the upper rear portion 2156. In some configurations, the upper and lower edges of the upper rear portion 2156 can generally follow the curvature or shape of the corresponding portions of the nasal region 2168 and oral region 2166, respectively. The upper rear portion 2156 can extend along a substantial width of the mask seal 2104. For example, the upper rear portion 2156 can have a length that is at least one-half of a width of the mask seal 2104 at the location of the upper rear portion 2156 and/or a length that is longer than a width of the nasal opening 2124. In some configurations, the upper rear portion 2156 can have a length that is greater than a width of the oral opening 2122. The upper rear portion 2156 can be centered in a lateral direction of the mask seal 2104. In some configurations, the upper rear portion 2156 extends into or is connected with the outer peripheral portions 2162. Such an arrangement assists in maintaining the open shape of the rear surface of the mask seal 2104 to facilitate fitment to the user's face.

The upper rear portion 2156 can provide support to the mask seal 2104 between the nasal region 2168 and the oral region 2166, such as to limit, inhibit or prevent collapse of the mask seal 2104 in a lateral direction between the outer peripheral portions 2162 and/or in a vertical direction between the nasal region 2168 and the oral region 2166 or to maintain a desired separation of those portions 2162 or regions 2168, 2166. The upper rear portion 2156 can have a thickness that is sufficient to provide such support and that can be greater than one or both of the nasal region 2168 and the oral region 2166. The upper rear portion 2156 can have a thickness that is smaller than one or both of the outer peripheral portions 2162 and the supports 2163. In some configurations, the upper rear portion 2156 has a thickness that is greater than both the nasal region 2168 and the oral region 2166 and smaller than both the outer peripheral portions 2162 and the supports 2163. In some configurations, a portion or an entirety of the upper rear portion 2156 can have a thickness that is between about 0.5 mm and about 1.5 mm. In the illustrated configuration, a portion or an entirety the upper rear portion 2156 has a thickness of about 1.0 mm. The thickness could be smaller or larger depending on the desired characteristics of the support provided by the upper rear portion 2156.

Figure 5:
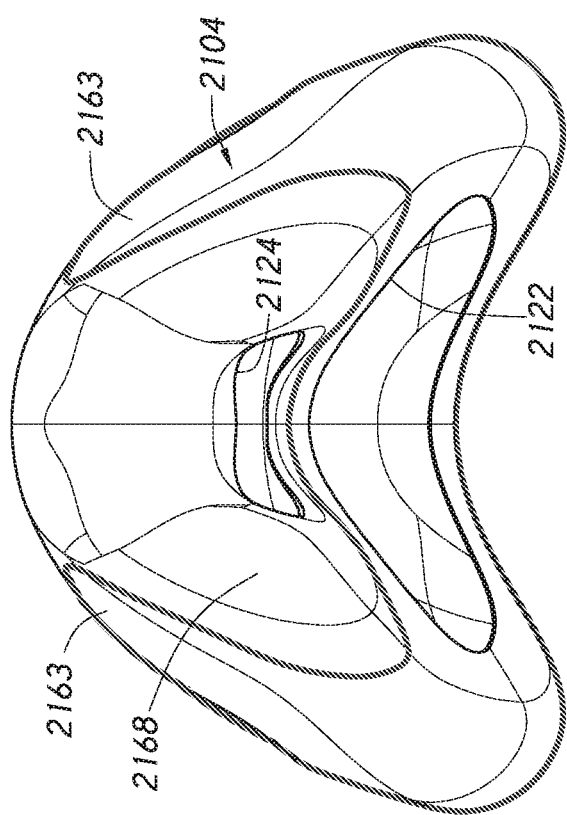
FIG. 5 is a rear view of the mask assembly of FIG. 4 illustrating a thickened region of a mask seal of the mask assembly.
Figure 6:
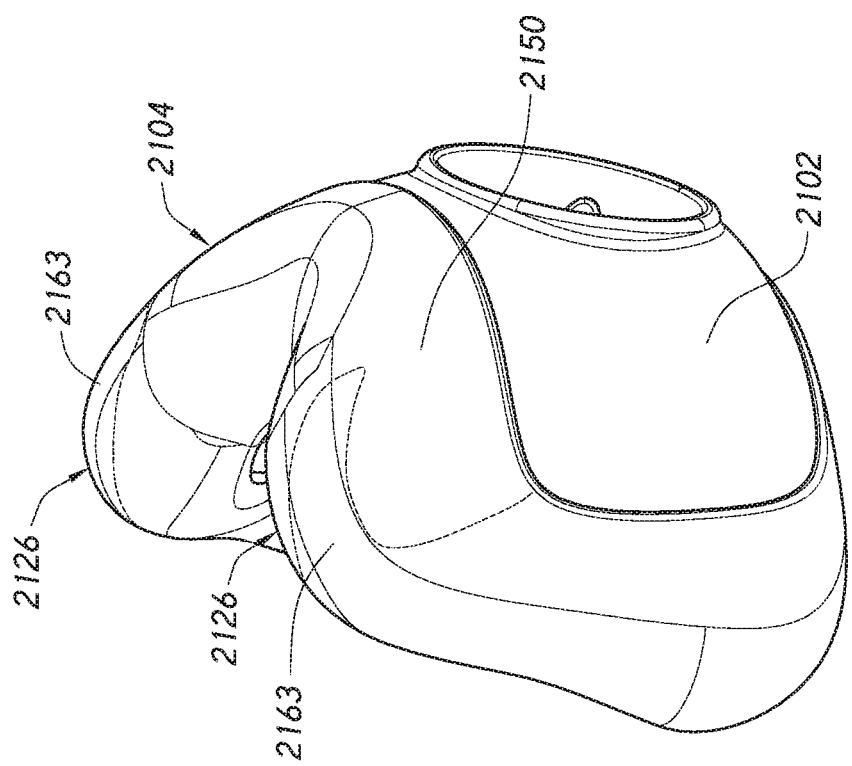
FIG. 6 is a side view of the mask assembly of FIG. 4 illustrating the thickened region of the mask seal.
Figure 7:
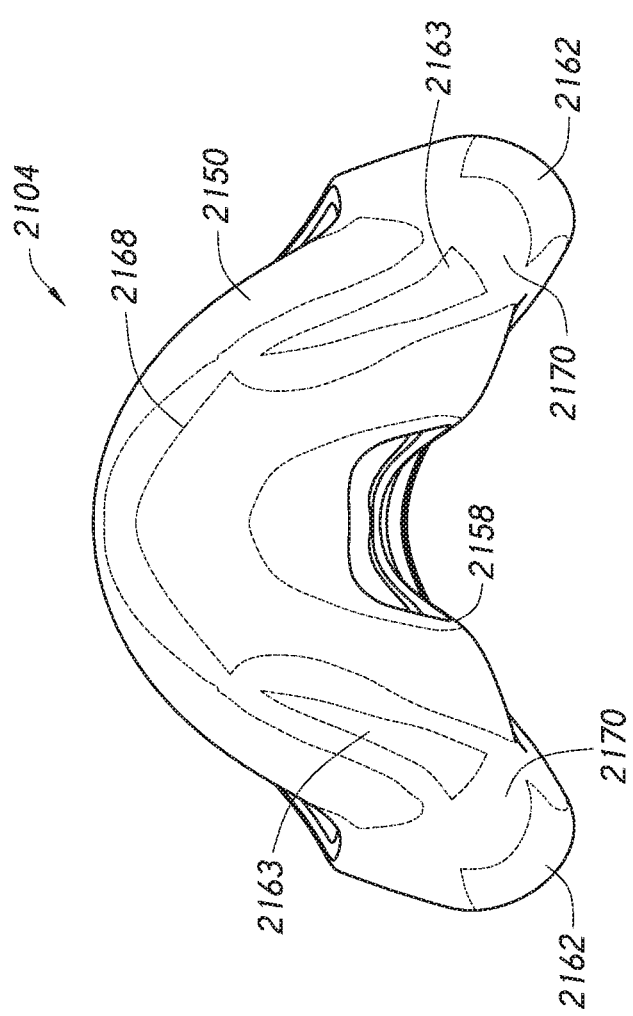
FIG. 7 is a top view of the mask seal of the mask assembly of FIG. 4 illustrating regions of different thickness of the mask seal.
Figure 8:
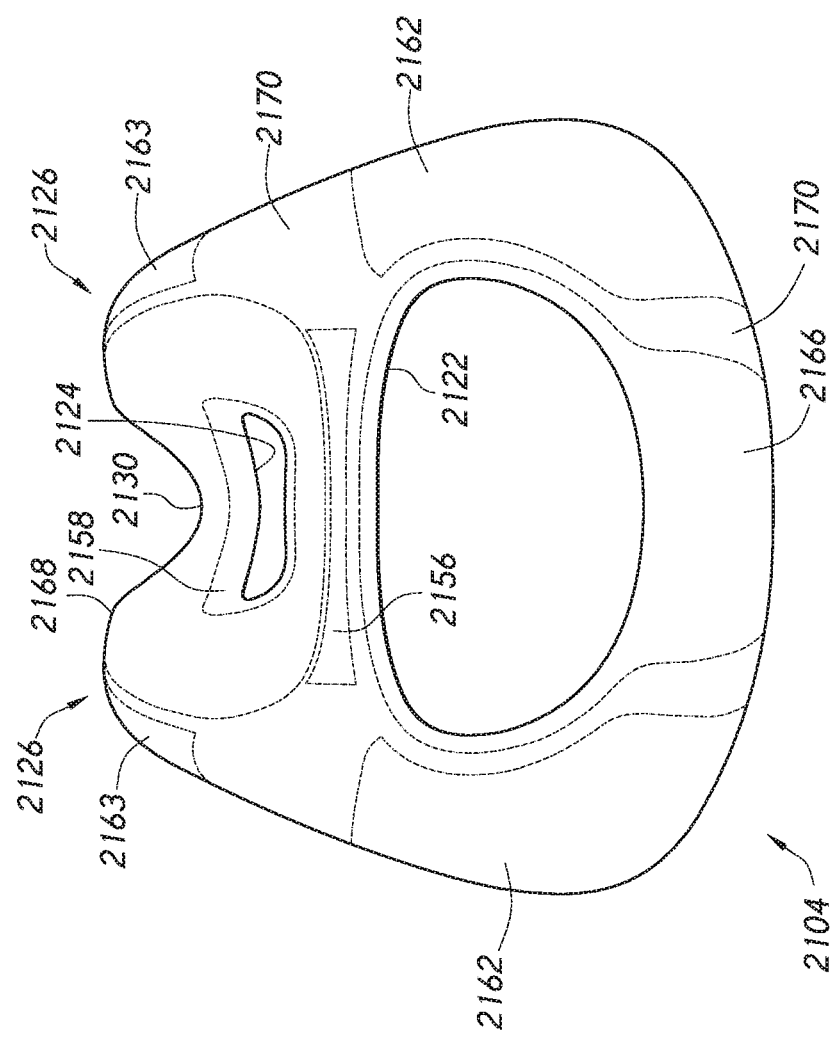
FIG. 8 is a rear view of the mask seal of FIG. 7 illustrating regions of different thickness of the mask seal.
Figure 9:
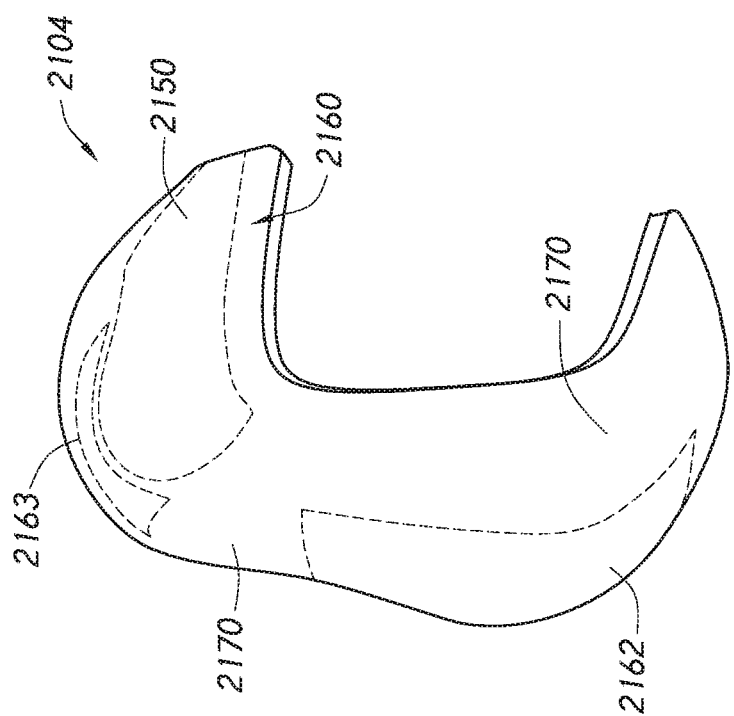
FIG. 9 is a side view of the mask seal of FIG. 7 illustrating regions of different thickness of the mask seal.
Figure 10:
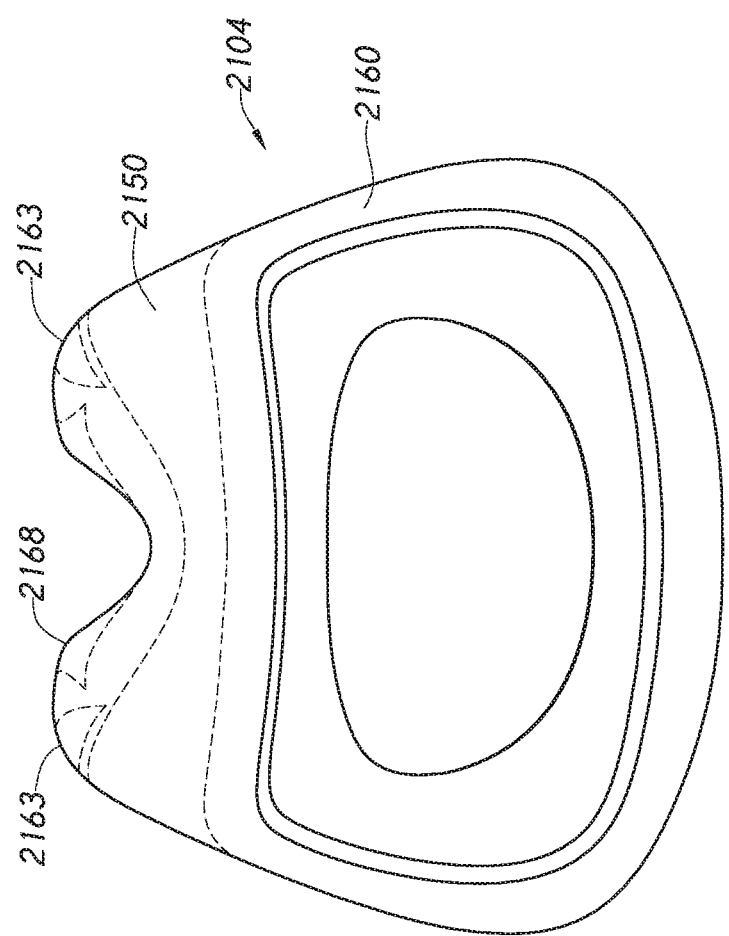
FIG. 10 is a front view of the mask seal of FIG. 7 illustrating regions of different thickness of the mask seal.
Figure 11:
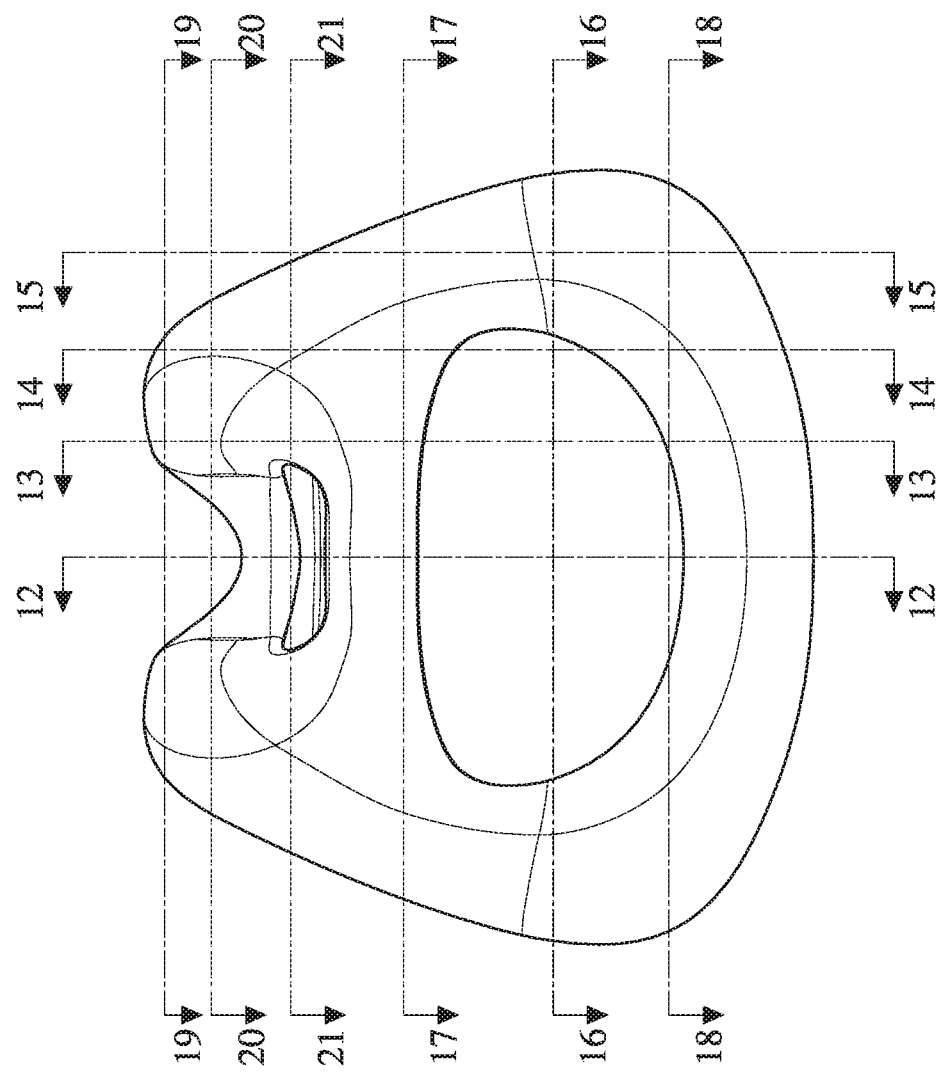
FIG. 11 is a rear view of the mask seal of FIG. 7.
Figure 12:
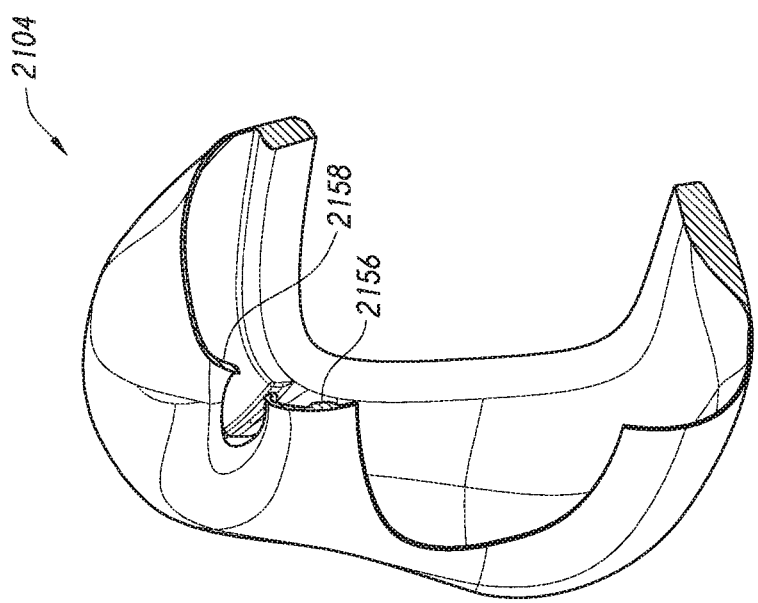
FIG. 12 is a sectional view of the mask seal taken along line 12-12 of FIG. 11.
Figure 13:
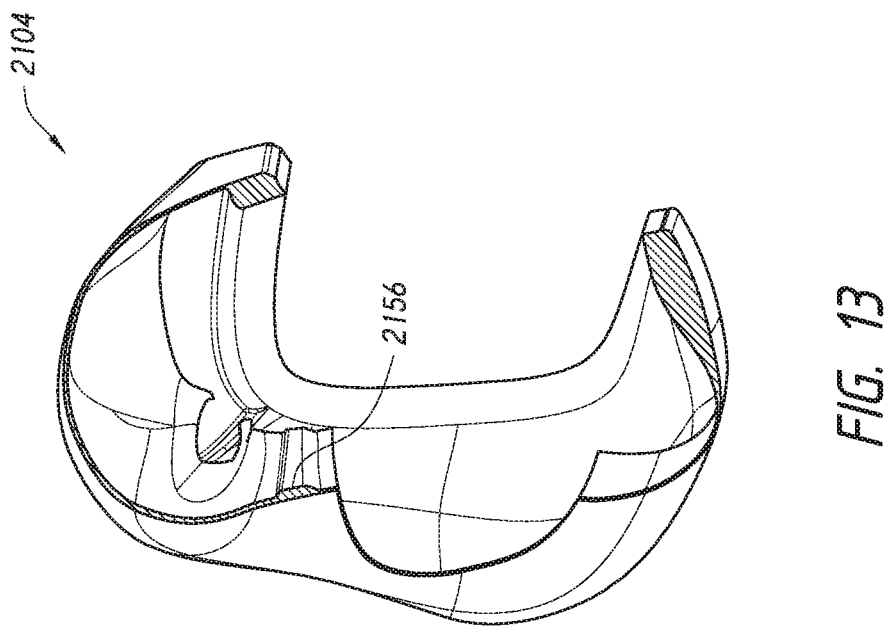
FIG. 13 is a sectional view of the mask seal taken along line 13-13 of FIG. 11.
Figure 14:
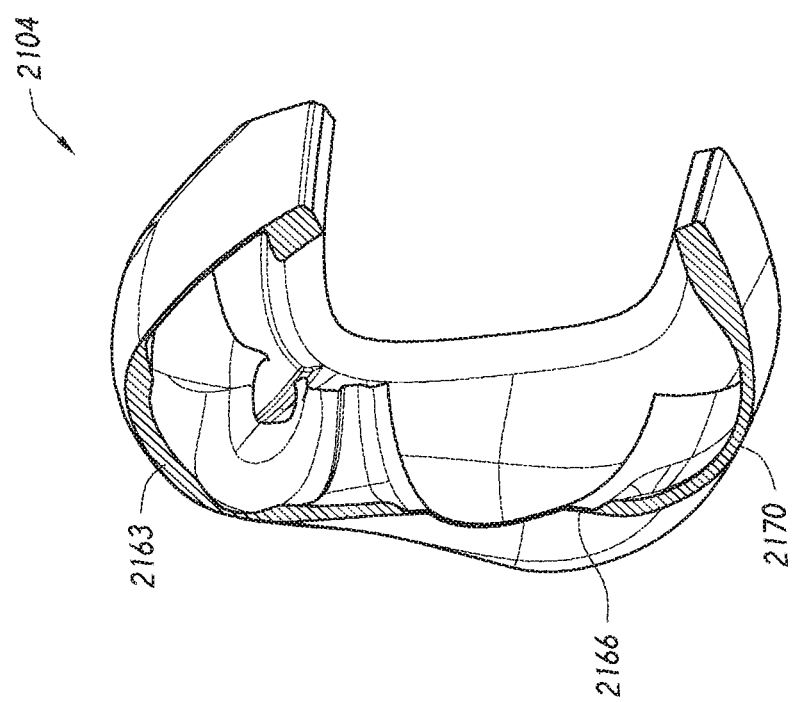
FIG. 14 is a sectional view of the mask seal taken along line 14-14 of FIG. 11.
Figure 15:
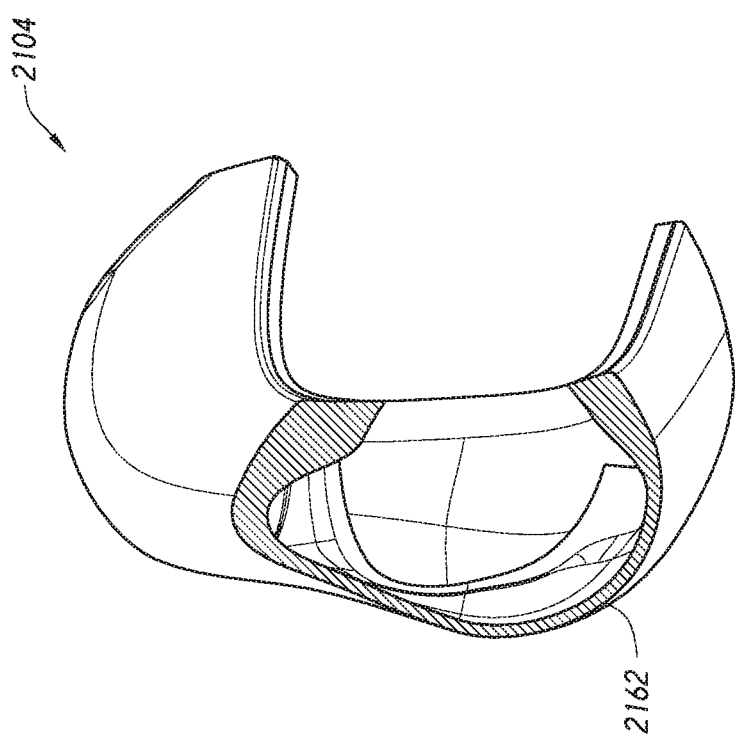
FIG. 15 is a sectional view of the mask seal taken along line 15-15 of FIG. 11.
Figure 16:
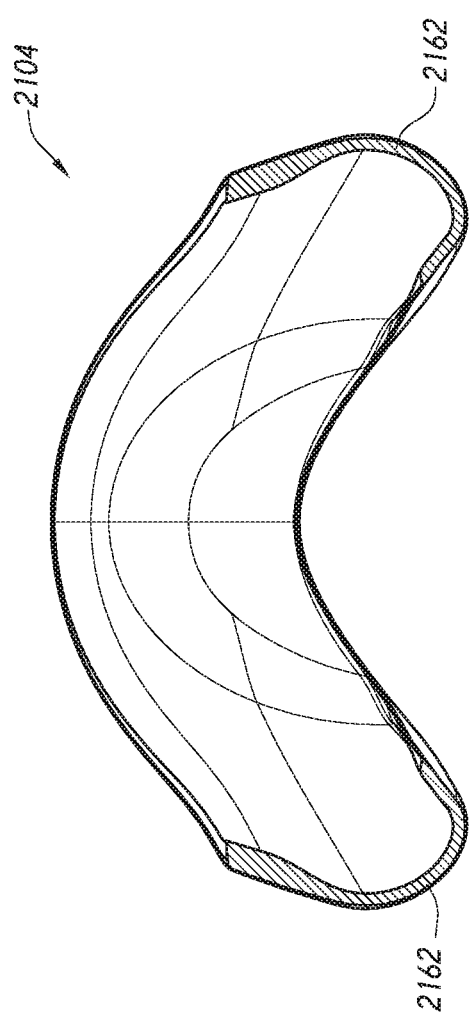
FIG. 16 is a sectional view of the mask seal taken along line 16-16 of FIG. 11.
Figure 17:
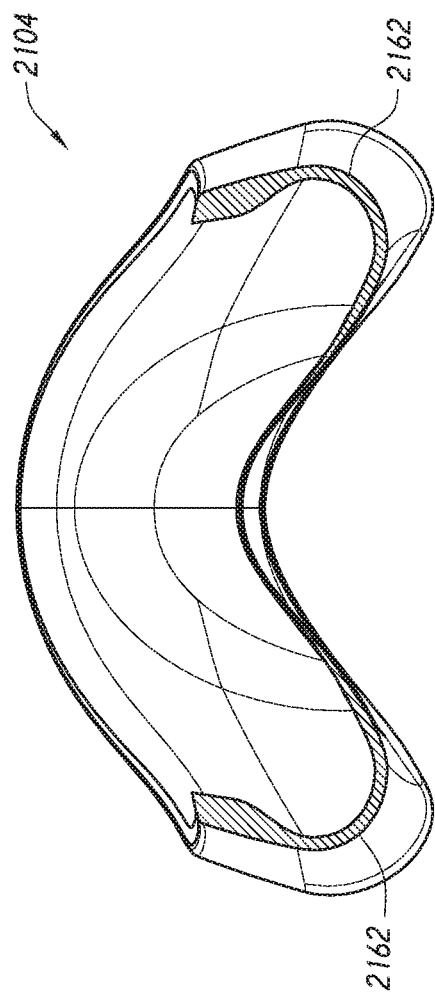
FIG. 17 is a sectional view of the mask seal taken along line 17-17 of FIG. 11.
Figure 18:
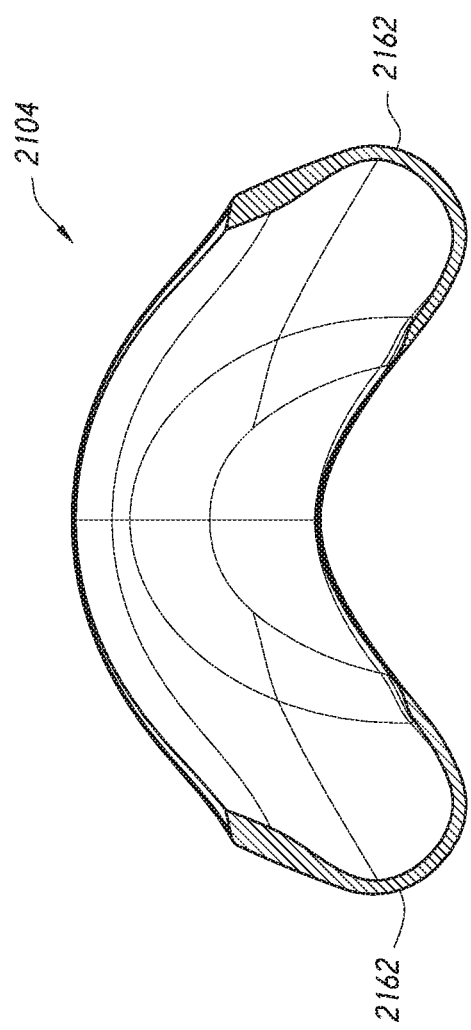
FIG. 18 is a sectional view of the mask seal taken along line 18-18 of FIG. 11.

The mask seal 2104 can have other portions outside of those described above. For example, the mask seal 2104 can have one or more transition portions 2170 in the area(s) between the above-described portions. The transition portion 2170 can be referred to in the singular herein; however, the transition portion 2170 is not necessarily a single contiguous region, but may comprise several discrete or non-contiguous regions. The transition portion 2170 can define a transitioning thickness between any one or more (including all) of the upper front portion 2150, the upper rear portion 2156, the supports 2163, the outer peripheral portions 2162, the oral region 2166 and the nasal region 2168. The transition portion 2170 can define a thickness that extends away from or is positioned or transitions between two regions in any suitable manner, such as a gradual or abrupt transition, for example. A transition in thickness can occur within the transition portion 2170 or along an edge of the transition portion 2170, for example. In the illustrated configuration, the outer peripheral portions 2162 are generally surrounded by the transitional portion 2170. The outer peripheral portions 2162 can make a relatively smooth transition into the supports 2163 such that the outer peripheral portions 2162, transition portion 2170 and supports 2163 comprise a generally continuous thickened region, as illustrated in FIG. 5. The oral region 2166 can be separated from the outer peripheral portions 2162 and/or the upper rear portion 2156 by a transition portion 2170. Other configurations also are possible.

The illustrated mask seal 2104 includes a connecting region 2160 that generally encircles an opening that receives the mask shell 2102 and can be configured to join the mask seal 2104 to the mask shell 2102. In the illustrated arrangement, the connecting region 2160 is illustrated as forming a portion of or being contained with the transition portion 2170. In some configurations, the connecting region 2160 could have a specific construction providing desirable characteristics, such as permitting connection to the mask shell 2102 and/or providing durability. In some configurations, the connecting region 2160 can be the thickest portion of the seal member 2104. In some configurations, the thickness of the connecting region can be between about 2 mm and about 5 mm or between about 3 mm and about 3.5 mm. In other configurations, the thickness could be smaller or larger depending on the desired properties, such as type of connection with the mask shell 2102 (e.g., overmolded connection). The thickness can vary within the connecting region 2160, such as in the case of the mask seal 2104 mechanically-engaging the mask shell 2102. For example, the periphery of the mask shell 2102 can include recesses or openings that are engaged or passed through by material of the mask seal 2104.

The illustrated mask seal 2104 also includes a nasal opening support 2158 that surrounds a portion or an entirety of the nasal opening 2124. The nasal opening support 2158 can assist in maintaining a desired shape of the nasal opening 2124 and/or limit, inhibit or prevent collapse of the nasal opening 2124. In the illustrated arrangement, the nasal opening support 2158 is illustrated as forming a portion of the transition portion 2170. The nasal opening support 2158 can have a variable or a relatively constant thickness. The nasal opening support 2158 can have a thickness that is larger than the thickness of the nasal region 2168. In some configurations, the nasal opening support 2158 can have a thickness of between about 1.0 mm to about 2.5 mm, for example and without limitation. As described above, the nasal opening support 2158 can be an insert or cushion that is coupled to the material of other portions of the mask seal 2104, such as a substantial entirety of the mask seal 2104.

With additional reference to FIGS. 1-3 and 22-24, as described above, the mask seal 2104 and mask shell 2102 (mask assembly 2100) can form a portion of an interface assembly, which can include the frame 2178 and the headgear 2180. The frame 2178 can be removably connected to the mask assembly 2100 by any suitable arrangement. For example, the frame 2178 can be coupled at or around the aperture 2114 of the mask shell 2102, such as by a snap fit, friction fit or clip connection, among other possibilities. The mask assembly 2100 can be keyed to the frame 2178 to permit assembly in only the correct orientation. The conduit connector 2106 can also be attached to the mask shell 2102, frame 2178 or otherwise supported relative to and adapted to communicate with an interior space of the mask assembly 2100.

In the illustrated arrangement, the frame 2178 comprises one or more portions that are positioned adjacent or contact a portion of the paddles 2126. In some configurations, the frame 2178 comprises a pair of support portions or covers 2182, each of which is associated with one of the paddles 2126 of the mask seal 2104. References to covers 2182 herein can refer to other suitable support structures for the paddles 2126 unless indicated otherwise. The covers 2182 can provide a desirable level of support to the paddles 2126, such as to inhibit or prevent over-expansion and/or outward bulging of the paddles 2126, which can occur in response to gas pressure within the mask seal 2104, for example. As described above, portions of the mask seal 2104 can be textured for purposes of user comfort. Texturing of a surface of the paddles 2126 that contacts or faces the paddle covers 2182 can allow or facilitate relative movement (e.g., sliding movement) of the paddles 2126 and the paddle covers 2182. However, if it is desired for the paddle covers 2182 to grip the paddles 2126 to inhibit movement therebetween, the surface of the paddles 2126 facing or contacting the paddle covers 2182 can be non-textured or have a smooth surface finish. Any suitable method for texturing the mask seal 2104 can be utilized, such as bead blasting of the mold for the mask seal 2104.

Although the illustrated covers 2182 are integrated with the frame 2178, in other configurations, the covers 2182 could be otherwise supported in a desired position relative to the paddles 2126 by any component of the interface assembly. For example, the covers 2182 could be a separate component(s) coupled to the frame 2178 or other portion of the interface assembly, including the mask shell 2102. Such separate covers 2182 can be glued, clipped, welded or otherwise attached to an underlying support structure. In some configurations, the covers 2182 could be integrated with the mask shell 2102. In some configurations, the covers 2182 could be a portion of the mask seal 2104, such as portion having greater thickness or stiffness relative to the paddles 2126. In the illustrated arrangement, the covers 2182 are unitarily formed with the frame 2178. Similarly, the covers 2182 could be unitarily formed with the mask shell 2102, mask seal 2104 or other portion of the interface assembly.

In some configurations, the covers 2182 are positioned next to or against a laterally outer surface of the paddles 2126, with or without a gap, or a varying gap, therebetween, prior to the paddles 2126 being pressurized. With such an arrangement, the covers 2182 can contact the paddles 2126 to limit, inhibit or prevent an undesirable amount of expansion or outward movement of the paddles 2126, such as due to gas pressure within the mask seal 2104. While some expansion of the paddles 2126 may be desirable to, for instance, control creasing of the paddles 2126 or upper portion of the mask seal 2104 (e.g., the nasal region 2168), too much expansion may be uncomfortable to the user, such as by causing the nasal region to press against the underside of the user's nose, and/or compromise the seal between the face of the user and the paddles 2126 or other portions of the mask seal 2104. Thus, characteristics (e.g., size, shape or location) of the covers 2182 can be selected to provide a desired level of support and/or allow a desired level of expansion of the paddles 2126 or other portions of the mask seal 2104. Preferably, the paddles 2126 or at least upper portions of the paddles 2126 are not coupled to the covers 2182 such that the paddles 2126 can flex or pivot inwardly away from the covers 2182. In some configurations, laterally outer surfaces of the paddles 2126 can move inwardly away from the covers 2182. Such an arrangement can advantageously assist in maintaining contact between the laterally inner surfaces of the paddles 2126 and the user's face when downward pressure is applied to the nasal region 2168.

In some configurations, the covers 2182 cover only a portion of the laterally-outward or forward-facing surfaces of the paddles 2126. With such an arrangement, the covers 2182 can provide a desired balance between user comfort and providing support to the paddles 2126. For example, the covers 2182 can cover only a portion of the paddles 2126 in a fore-aft direction. In the illustrated arrangement, the covers 2182 support a forward portion of the paddles 2126 and leave at least a rearward portion of the paddles 2126 exposed. In the illustrated arrangement, the covers 2182 cover substantially an entire height of the paddles 2126. In some configurations, the covers 2182 could cover a substantial entirety or an entirety of the length of the paddles 2126, while leaving some of the height of the paddles 2126 exposed. In some configurations, the covers 2182 could cover an intermediate portion of the paddles 2126, leaving forward and rearward portions exposed. In some configurations, the covers 2182 cover or overlap at least about one-third or one-half of a laterally-outward or forward-facing surface of the paddles 2126. In some configurations, the covers 2182 cover or overlap at least about two-thirds or three-quarters of a laterally-outward or forward-facing surface of the paddles 2126.

In some configurations, the paddle covers 2182 can be configured to provide localized support to a portion of the paddles 2126. For example, the paddle covers 2182 can be in the form of elongate finger structures. Such finger structures can provide support to a relatively small portion of the paddles 2126. The finger structures can originate at any desired location relative to the paddles 2126, such as a forward end, a rearward end or an intermediate portion of the paddles 2126. In some configurations, the finger structures are curved, such as curving toward a rearward direction or curving toward a forward direction. For example, the finger structures can curve to follow a portion or an entirety of an upper peripheral edge of the paddles 2126. Such finger structures can be located at, or spaced from, the peripheral edge of the paddles 2126. In some configurations, the finger structures can be configured to overlap support structures of the paddles 2126, such as the supports 2163 described further below.

Preferably, a space or valley 2184 is defined between the covers 2182. In the illustrated arrangement, the valley 2184 exposes a portion of the mask seal 2104, such as a forward portion of the nasal region 2168, to allow a desired amount of inflation of the mask seal 2104. In addition, such an arrangement can accommodate the tip of a user's nose or can provide space to accommodate a portion of the mask seal 2104 that is deflected by the user's nose.

Figure 22:
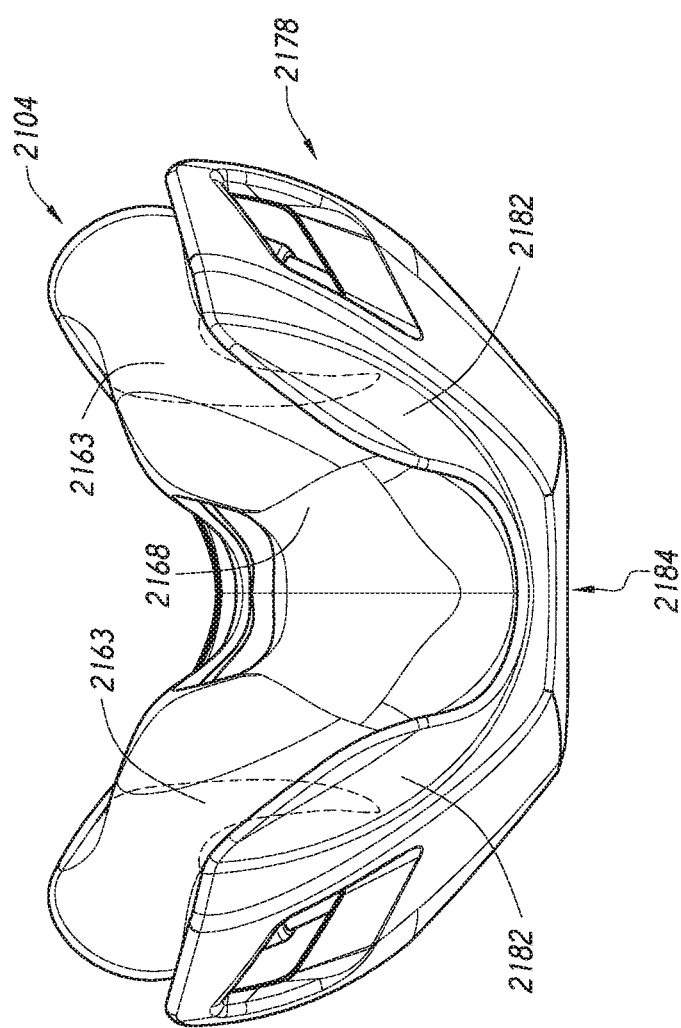
FIG. 22 is a top view of the interface portion of the interface assembly of FIG. 1 illustrating an example placement of support structures of the mask seal.

With reference to FIG. 22, the covers 2182 can cooperate with features of the mask seal 2104 to provide desirable performance characteristics. For example, the supports 2163 for the paddles 2126 can be positioned relative to the covers 2182 such that a load applied to the paddles 2126 by the user's face is transferred to the covers 2182 by the supports 2163. Thus, the supports 2163 can end at or shortly after the portion of the mask seal 2104 that contacts or is positioned adjacent the covers 2182 and may not extend into the upper front portion 2150 or all the way to the mask shell 2102. The supports 2163 can extend in a direction generally from the rearward or user-contacting surface of the mask seal 2104 toward its respective cover 2182. In some configurations, each of the supports 2163 extends generally or substantially in a longitudinal direction of the mask seal 2104. The supports 2163 can extend generally parallel to one another or can be closer at a forward end in comparison to a rearward end. In other words, the supports 2163 can converge in a direction moving from the rearward or user-contacting surface of the mask seal 2104 toward a front portion of the mask seal 2104. However, in other configurations, the supports 2163 can diverge from rear to front.

As described above, the supports 2163 can be in the form of or function in a manner similar to suspension members or springs to provide a resistance force in response to attempted compression or collapse of the paddles 2126 in a fore-aft direction. The thickness, shape, orientation and/or location of the supports 2163 inhibits or prevents collapse because the supports 2163 transmit force into the covers 2182. Because the force is transferred into the covers 2182, collapse of the regions of the mask seal 2104 near or surrounding the supports 2163 (e.g., the nasal region 2168 and/or the upper front portion 2150) is inhibited or prevented. Portions of the mask seal 2104 can deform or stretch, but preferably collapse is inhibited or prevented. Collapse of the seal can involve a loss of shape that causes leaks or other detrimental performance of the mask seal 2104. In some case, collapse involves contact of normally spaced-apart wall portions of the mask seal 2104 (e.g., contact between a relatively rearward wall portion and a relatively forward wall portion). The supports 2163 can also inhibit or prevent collapse of the valley of the mask seal 2104. In other words, the supports 2163 can assist in maintaining the paddles 2126 in a laterally-spaced or separated orientation.

In at least some configurations, the covers 2182 can also provide support for the paddles 2126 in the absence of supports 2163. Moreover, although the covers 2182 (or other similar support structures) are particularly useful for under-nose type nasal masks or combined nasal-oral masks, the covers 2182 or similar structures can be utilized in other types of interfaces, as well. For example, the covers 2182 can be utilized in nasal or combined nasal-oral mask assemblies or interfaces that cover, contact or seal against the bridge of the user's nose and/or include a T piece or other type of forehead support, for example and without limitation. The covers 2182 can be utilized, or modified for use, in any locations of an interface in which support against collapsing and/or support against overexpansion may be desirable. Such locations can be at or near the portion of the seal that contacts or extends alongside the user's nose or can be at other locations. As noted above, the covers 2182 can be utilized with or without corresponding supports 2163.

Possible locations of the supports 2163 relative to the covers 2182 are illustrated in FIG. 22. In some configurations, the supports 2163 extend generally between the covers 2182 and rearward surfaces of the paddles 2126 that contact the user's face. Such surfaces can coincide with sides of the nasal region 2168, for example. Forward ends of the supports 2163 can be aligned in a lateral direction with the covers 2182. In some configurations, forward ends of the supports 2163 could join one another, such as with a semi-circular joining portion, for example, and/or could extend all the way or substantially all the way to the mask shell 2102. Such an arrangement could provide greater shape-holding functionality and feedback. However, it has been determined that the covers 2182 allow the supports 2163 to terminate earlier while still providing a desirable amount of shape-holding and feedback. A shape of the supports 2163 can be selected to be complementary with or otherwise provide desired interaction with the covers 2182. Such an arrangement allows at least portions of the nasal region 2168 (e.g., the nasal tip region), if not the entire nasal region 2168, to be relatively thin to provide comfort to the user and/or provide desirable sealing characteristics.

If desired, a structure or structures similar to the supports 2163 (e.g., spring or suspension structures) could be provided in the nose tip area (or other areas of the nasal region 2168) to help maintain a desired shape of the mask seal 2104. It is contemplated that the provision of covers 2182 can permit such supports to have a smaller thickness than would otherwise be provided in the absence of the covers 2182 thereby increasing compliance to improve user comfort and sealing characteristics.

Figure 23:
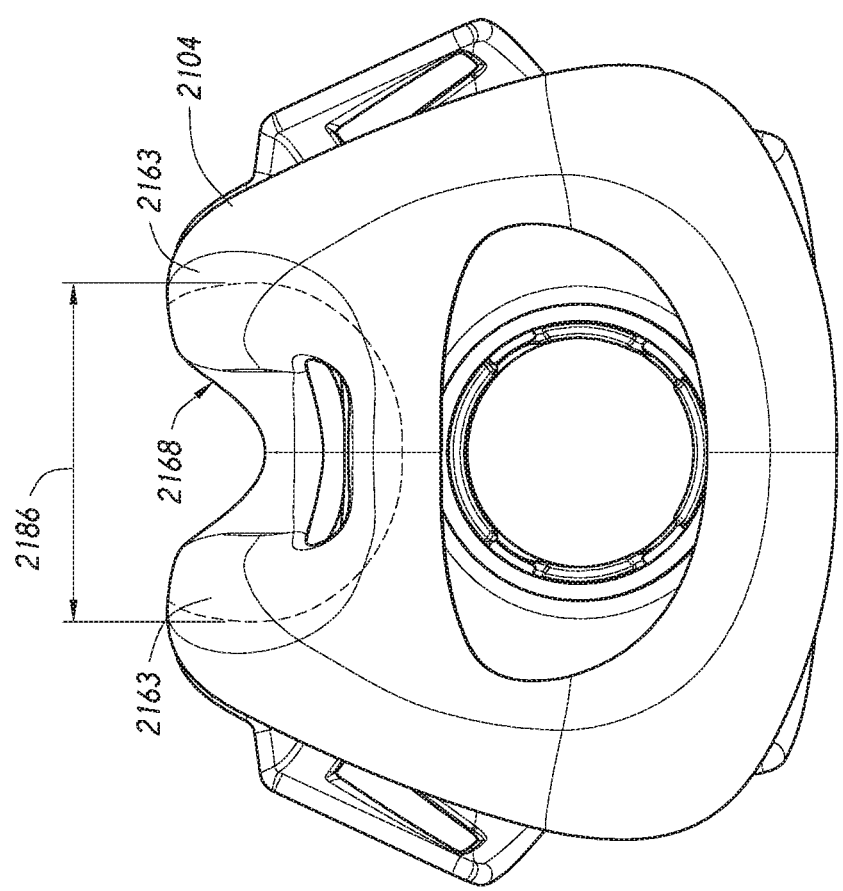
FIG. 23 is a rear view of the interface portion of FIG. 22.
Figure 24:
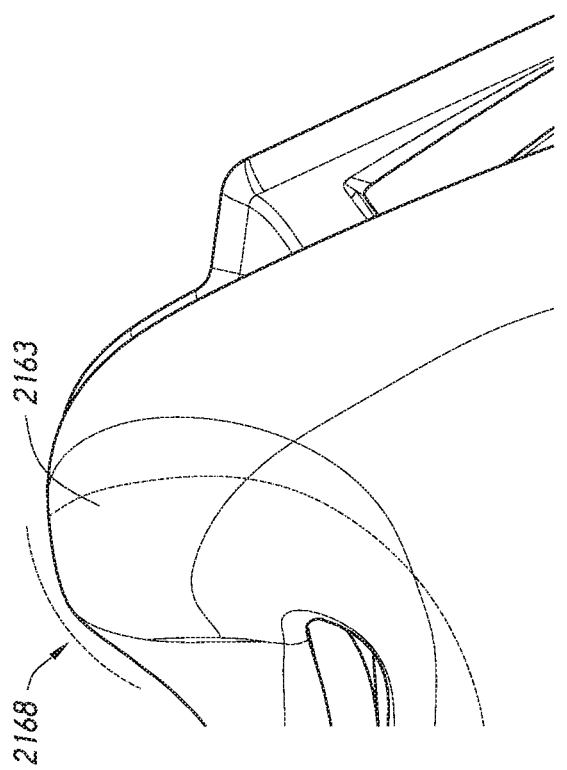
FIG. 24 is a rear view of a portion of the interface portion of FIG. 22.

With reference to FIGS. 23 and 24, rearward or user-contacting surface views of the mask seal 2104 and a portion of the nasal region 2168 are illustrated, respectively. It has been determined that an inner portion of the nasal region 2168 can be a region of the mask seal 2104 that can impact performance and there are certain features or properties that have been discovered to improve seal comfort, leak and overall performance. For example, a width 2186 of the nasal region 2168 or width between the spring structures or supports 2163 can influence seal comfort, leak and overall performance. In some configurations, this width is in the region of about 45 mm to about 50 mm, but could be smaller or larger, such as for different size mask seals 2104.

With reference to FIG. 24, in some configurations, the outer geometry profile of the mask seal 2104 from the spring structure or supports 2163 to the inner portion of the nasal region 2168 is a convex profile. Such an arrangement allows the paddles 2126 to displace away when the user's nose is fitted against the nasal region 2168 and provides a desirable sealing profile around the user's nostrils.

In addition, as described above, a portion or an entirety of the nasal region 2168 has a thickness of between about 0.3 mm and about 0.5 mm or 0.6 mm, in some configurations. In some configurations, at least the inner portion (excluding the nasal opening support 2158) of the nasal region 2168 has a thickness of at least about 0.3 mm to provide a desirable level of compliance while also inhibiting creasing over a range of facial geometries and/or operational pressures. In some configurations, the inner region of the nasal portion 2168 has a constant thickness. However, the thickness could be variable within the inner region of the nasal portion 2168. In some configurations, the thickness of the inner region of the nasal portion 2168 can vary from about 0.3 mm to slightly thicker values. In some configurations, the thickness of a portion or an entirety of the nasal region 2168 could be less than about 0.3 mm, which could provide increased compliance. However, such a thickness can result in creasing with some facial geometries and/or at lower operational pressures.

2. Sizing

As described above, sizing of over-the-nose full face seals that go over the nose bridge can be based on determining an overall height of the seal, which can be selected to accommodate a nasion to menton/sublabial measurement range of the desired population of users. Such a sizing methodology can result in multiple seal sizes (e.g., small, medium, large, extra-large) that differ in overall height. Such seal sizes can also differ in width; however, the differences in height are generally more significant than the differences in width because the nasion to menton/sublabial measurement variation is greater than the lip length variation, which can be used to determine seal width measurements. Because the end or tip of the nose is positioned within the breathing chamber and is not contacted to a significant extent by the sealing surface, a particular over-the-nose full face seal can accommodate a wide variety of nasal widths and nasal lengths (of the underside of the nose—e.g., subnasal to pronasal).

However, because the under-nose full face seals disclosed herein seal against an underside of the nose and along the sides of the nose, nasal width and nasal length variations, among other variations related to the underside of the nose (e.g., upward-facing and downward-facing) have a larger impact on seal fit and sizing in comparison to over-the-nose full face seal. Accordingly, in some configurations, the sizing methodology utilized to create different sizes of under-nose full face seals utilizes information on nasal width and/or nasal length variations, possibly along with other variations related to these characteristics.

Figure 25:
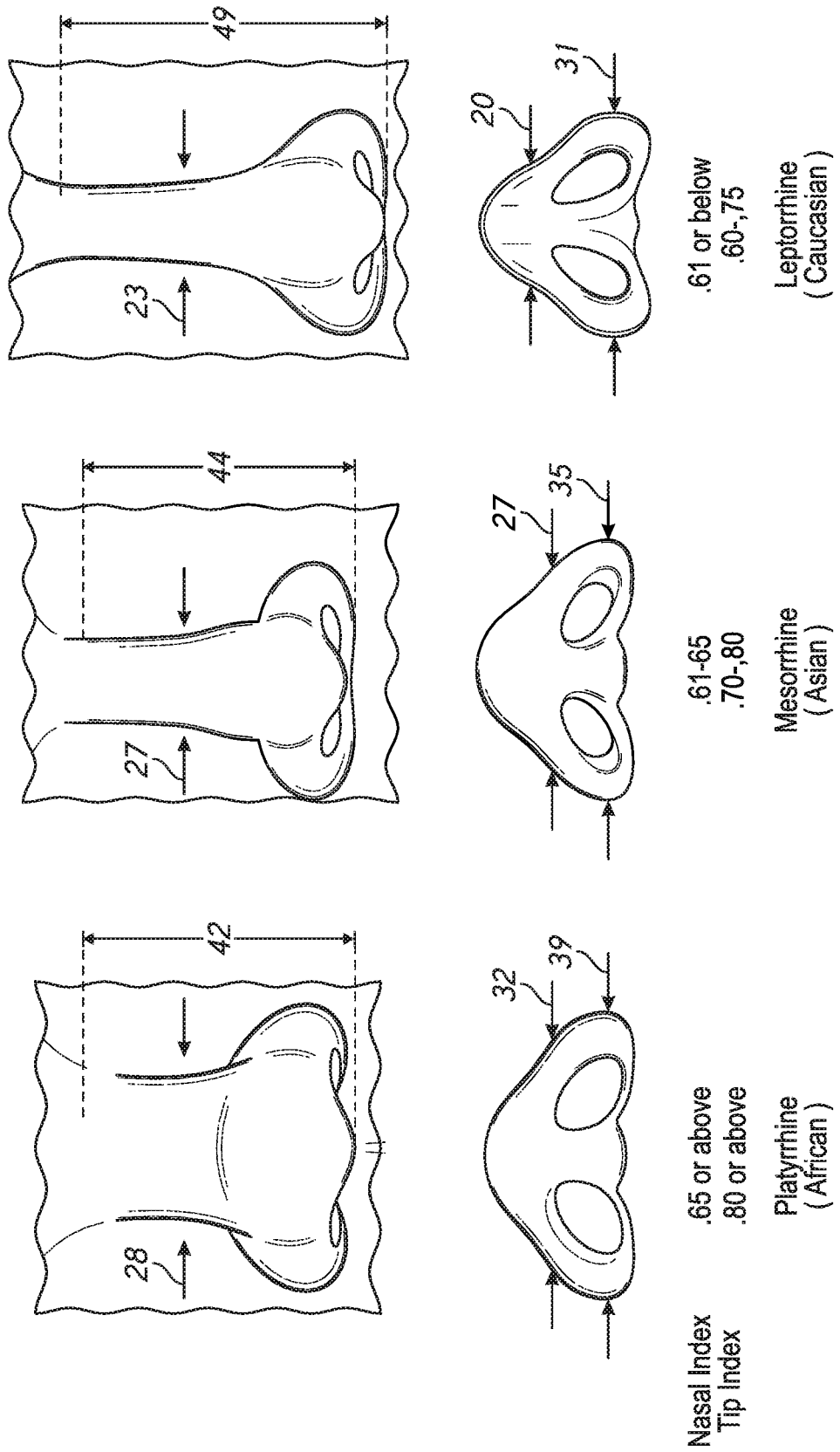
FIG. 25 is an illustration of three different nose types.

It has been determined that nasal shape and/or size generally correlates with ethnicity. That is, general trends or characteristics emerge among the nasal shapes and/or sizes of different ethnicities. By way of example, three ethnicities are illustrated in FIG. 25 and discussed herein: Caucasian, Asian, and African. In general, Caucasians tend to have a taller triangular shape to the underside of the nose, Africans tend to have a shorter triangular shape to the underside of the nose and Asians tend to have a triangular shape having a height in between those of Caucasians and Africans. Nasal Index and Tip Index can be used to compare different nose shapes. The Nasal Index is defined as the ratio of the nasal width between the piriform crests and the length of the nose. The Tip Index is defined as the ratio of the width of the nose at the nostril apex and the width at the widest part of the ala. Caucasian nose shapes generally have a Nasal Index of 0.61 or below and a Tip Index of between 0.60 and 0.75. African nose shapes generally have a Nasal Index of 0.65 or above and a Tip Index of 0.80 or above. Asian nose shapes generally have a Nasal Index of between 0.61 and 0.65 and a Tip Index of between 0.70 and 0.80. These variations have been considered for the purposes of sizing at least some of the under-nose seals disclosed herein.

Anthropometric data has been gathered by the Applicant for both OSA and non-OSA sufferers in the form of 3D facial scanning. Measurements have been taken from the facial scans and the data compiled for use in the designing of OSA interfaces. Although the sample sizes are small in terms of the global population, these measurements have been used to help with statistical analysis and sizing information and have been used in the sizing of at least some of the under-nose seals disclosed herein. For example, the data has been utilized to develop theories or tools for development of the sizing of under-nose seals, including a Nasal Displacement theory or tool and a Nasal Perimeter Length theory or tool. These are describe in turn below.

a. Nasal Displacement

The Nasal Displacement theory or tool determines the overall size nose the under-nose seal or mask can accommodate or is intended to accommodate taking into account width and length and can be used as a design tool to generate a range of mask sizes. It should be mentioned that with the complex nature of the problem of determining accurate nasal displacement values, a number of assumptions have been made for the purposes of simplification and practicality. Therefore, the theory or tool in at least some cases is used as a general guide only. The under-nose seal designs generated from this theory typically will then be verified on actual users to determine the exact parameters within which the seal can work at an acceptable level of sealing, comfort or other relevant factors.

Figure 26:
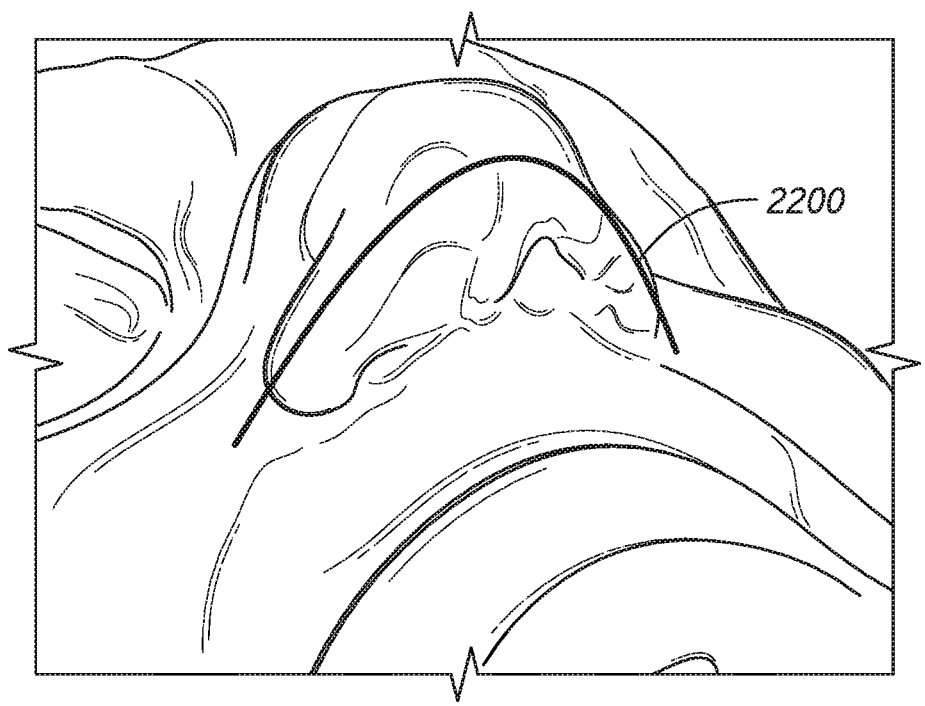
FIG. 26 illustrates a displacement profile of a patient's nose.
Figure 27:
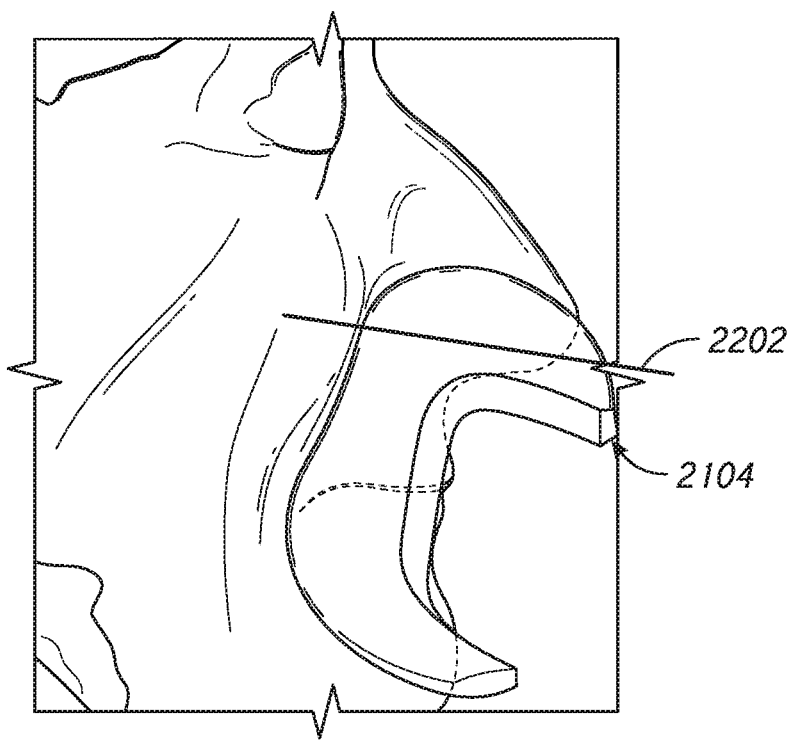
FIG. 27 is a side view of an under-nose seal in place on a patient and illustrating a nasal displacement plane.

The nasal areas of the illustrated under-nose nasal seals or masks have a surface that displaces when the mask is worn cupping the nares of the user and providing a seal around the nose. The displacement profile 2200 of a patient's nose is shown in FIG. 26. The actual position of the displacement profile 2200 can vary as a result of variations in nasal geometry; however, it is presently contemplated that it will generally lie within a plane 2202 running through the lowest section of the nose, which is generally the largest cross sectional area and outer profile. FIG. 27 illustrates an under-nose seal 2104 on the face of the patient of FIG. 26 with the plane 2202 also illustrated. As a result, it can be determined approximately where the plane 2202 will intersect the seal 2104 in the nasal area. In general, the intersection between the plane 2202 and the seal 2014 will be the location of maximum displacement that the seal 2104 will experience to accommodate the user's nose.

Figure 28:
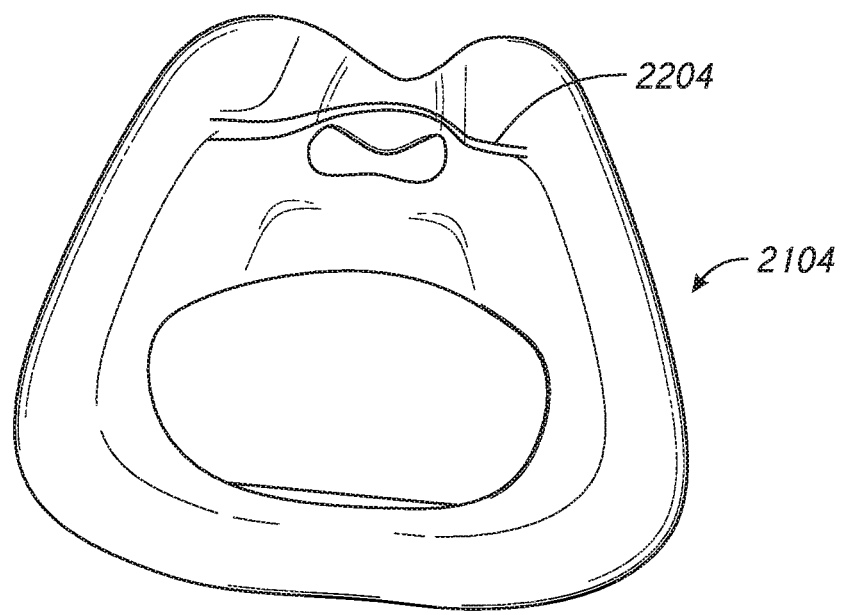
FIG. 28 is a rear view of the under-nose seal of FIG. 27 illustrating the nasal displacement plane projected as curves onto the seal.

FIG. 28 illustrates a projection of the plane 2202 onto the surface of the seal 2104, which results in a projected curve 2204. The length of the curve 2204 can be measured (by, for example, utilizing CAD software) and the result can be or approximate the largest nasal profile the seal 2104 can accommodate in the nasal area. In the illustrated arrangement, two planes 2202 were used to account for variation in nasal shapes. An average of the lengths of the resulting curves 2204 was calculated. For an example of an under-nose seal 2104 as disclosed herein, this average length of the two curves 2204 was calculated to be 83 mm. Thus, preferably, such a seal 2104 is intended to accommodate a nasal displacement profile 2200 that is less than or equal to about 83 mm.

b. Nasal Perimeter Length

Because of its complex shape, the actual nasal perimeter length is a difficult measurement to attain directly from a user's face. The length could be measured in CAD software but would very time consuming for each individual scan. Therefore, in at least some configurations, the Applicant has utilized anthropometric data to determine or approximate this measurement. Again, a number of assumptions have been made for the purposes of simplification and practicality. Therefore, the theory or tool in at least some cases is used as a general guide only.

Figure 29:
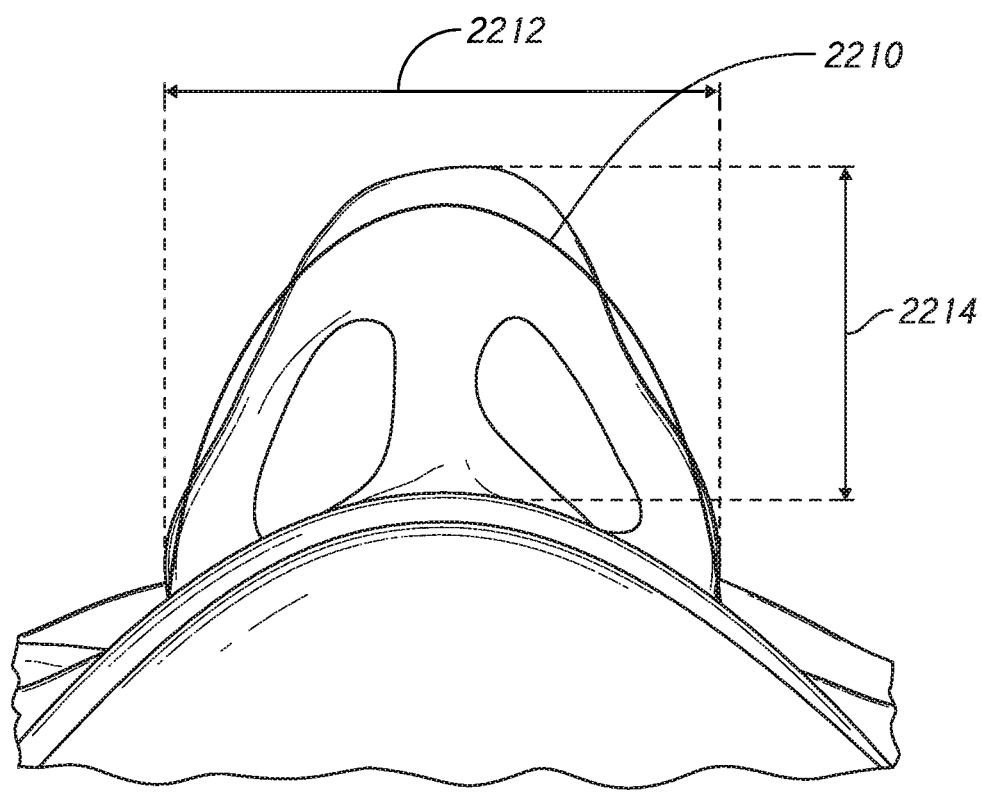
FIG. 29 is a view of the underside of the patient's nose illustrating nasal breadth and nasal length dimension along with a nasal perimeter length estimated curve.
Figures 30, 31:
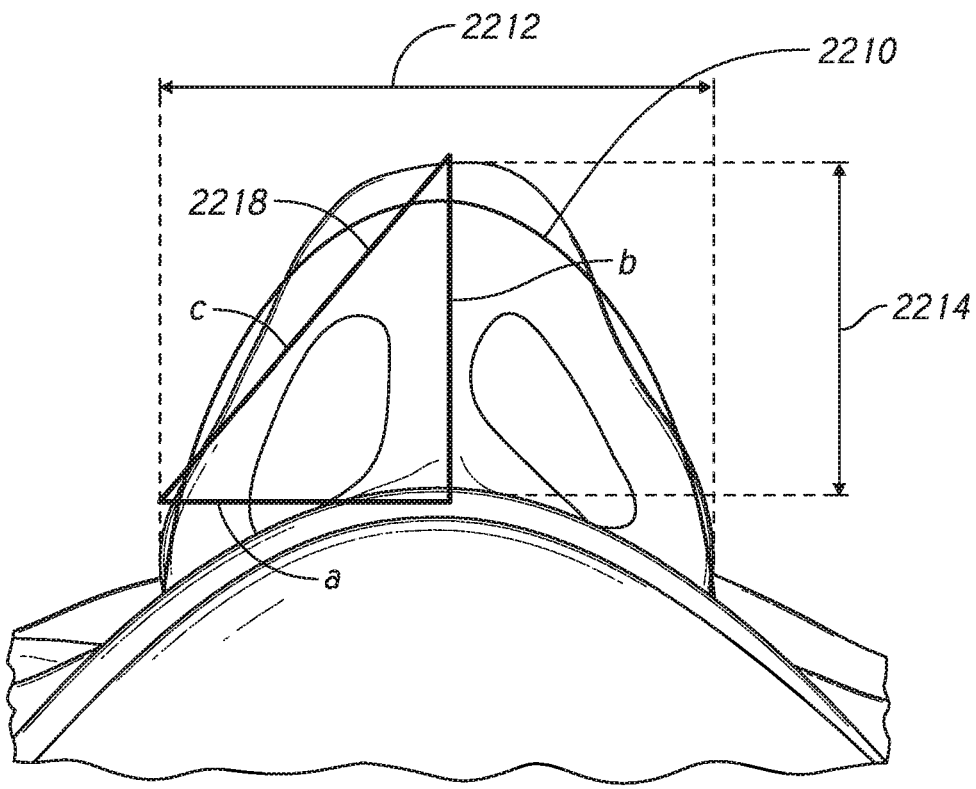
FIG. 30 is a view of the underside of the patient's nose similar to FIG. 29 illustrating a right triangle utilized to estimate the nasal perimeter length.
FIG. 31 is a chart illustrating a method for estimating nasal perimeter length using nasal dimensions in combination with a scaling factor.

FIG. 29 illustrates the 'approximate' nasal perimeter length 2210 on a user's nose. This perimeter length 2210 approximates a parabolic curve. In some configurations, nose breadth 2212 and nose length (subnasal to pronasal) 2214 dimensions are used to calculate this length 2210. With reference to FIG. 30, for simplicity, in some configurations, the length 2210 of the parabolic curve is approximated to a right triangle 2218. If desired, a scaling factor can be applied to better approximate the actual curve length 2210. The scaling factor can be determined by measuring the actual nasal perimeter (for example, in CAD software) for a range of nasal geometries and relating this back to nasal dimensions that are easier to measure or determine, such as nose breadth 2212 and nose length 2214.

In some configurations, the scaling factor utilized for design purposes can be an average of the individual scaling factors for all of the actual samples used. For example, FIG. 31 illustrates a chart having data associated with five different individuals. The first (left) column is a scan identification number. The second column is nose breadth 2212. The third column is nose length 2214. The fourth column is the calculated length of the hypotenuse C of the right triangle 2218 based on the nose breadth 2212 and nose length 2214 dimensions. The fifth column is the hypotenuse C length times the scan-specific scaling factor of the sixth column. The seventh column is the calculated size determined by the hypotenuse C length times the average or overall scaling factor 2220. The last (right or eighth) column of the table is the fifth column (result using the scan-specific scaling factor) divided by the calculated size using the average scaling factor 2220 of the seventh column. Thus, the last column illustrates that all of the calculated nasal perimeter lengths 2210 are within 8-9% of the actual measurements (for example, taken from CAD). For the purpose of this analysis, this is considered a reasonable measurement and methodology for determining the overall nose size of each subject utilizing relatively easy-to-measure or readily-available nasal geometry data. The scaling factor 2220 was then used across an entire database of nasal geometry data to categorise and sort the data for overall nose size. The resulting values were then used to determine whether each subject will fit the design parameters of each seal size. Again, preferably, this theory or tool will be verified once actual seals are produced and tested on a range of nose sizes.

c. Under-Nose Full Face Seal Size Analysis

Figure 32:
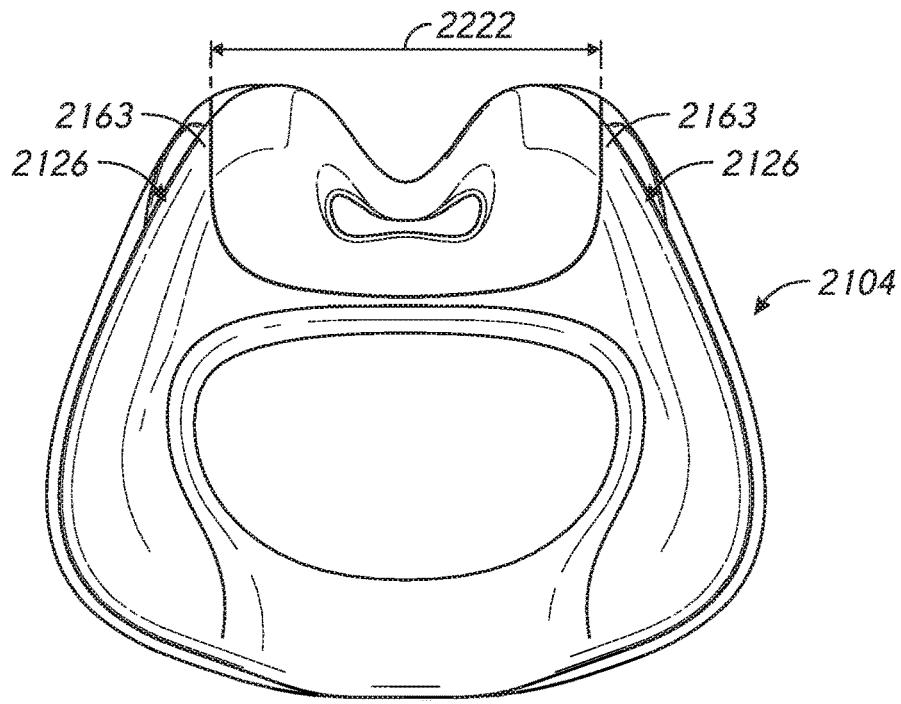
FIG. 32 is a rear view of the under-nose seal of FIG. 28 illustrating a maximum lateral dimension of the nasal region of the seal.

The above analysis and design theory/tool was applied to a particular under-nose full face seal 2104 already under development, which is illustrated in FIGS. 28 and 32. The seal 2104 is the same as or substantially similar to the seals 2104 described above or elsewhere herein. In the illustrated arrangement, the seal 2104 comprises support structures or supports 2163 within the paddles 2126 or portions of the seal 2104 positioned alongside the user's nose. The maximum nose breadth 2212 that the seal 2104 is configured to accommodate is determined by the maximum lateral distance 2222 between inner edges of the supports 2163. For the illustrated seal 2104, the value of the maximum lateral distance 2222 is 46 mm. Using the maximum nasal perimeter length 2204 of 83 mm as discussed in connection to FIG. 28, the portion of an overall population of users the seal 2104 will accommodate was determined using a scatter plot (FIG. 33).

Figure 33:
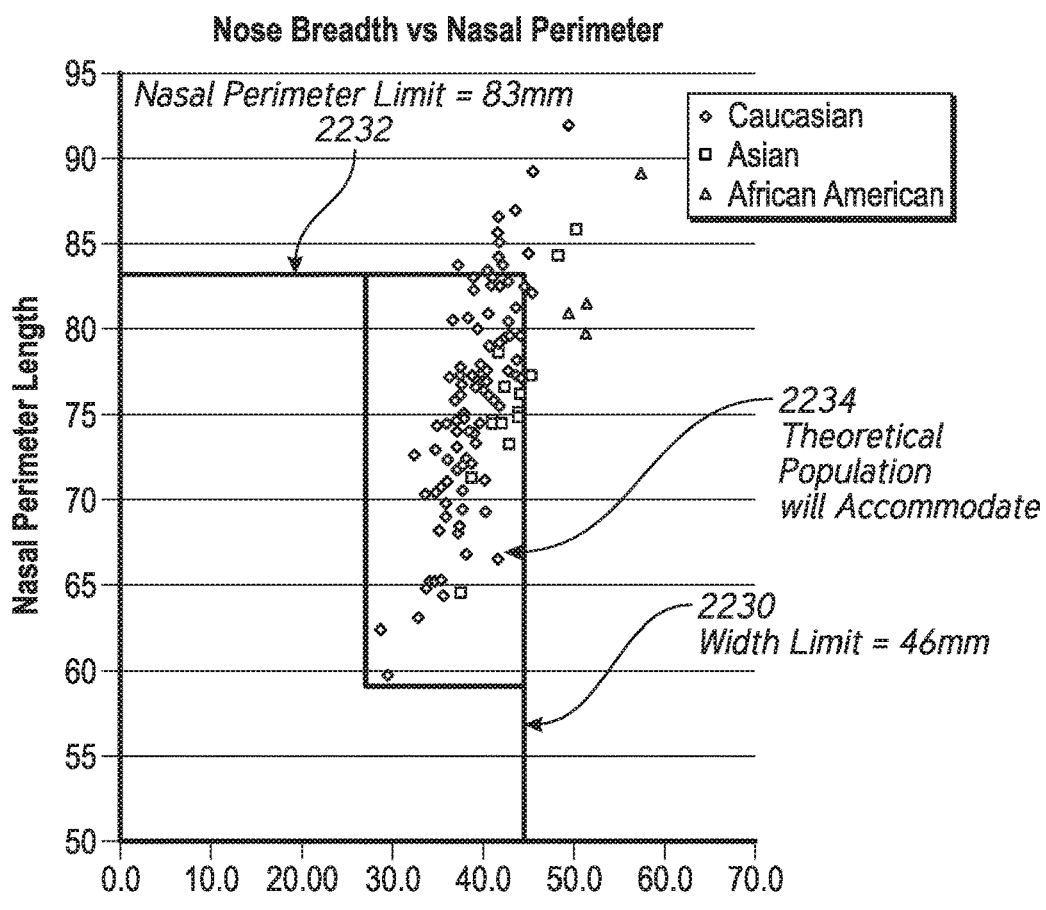
FIG. 33 is a scatter plot of nose breadth versus nasal perimeter length illustrating a theoretical population that will fit the seal of FIGS. 28 and 32.

FIG. 33 illustrates a scatter plot of nose breadth 2212 versus nasal perimeter length 2210 for a user population. An upper limit 2230 is set on the nose breadth 2212 based on the maximum lateral distance 2222 of 46 mm as illustrated in FIG. 32. Similarly, an upper limit 2232 is set on the nasal perimeter length 2210 based on the length of the projected curve 2204 of 83 mm as illustrated in FIG. 28. An area 2234 below the upper limits 2230 and 2232 captures and represents a theoretical portion of the illustrated user population that can be accommodated by the seal 2104.

Figure 34:
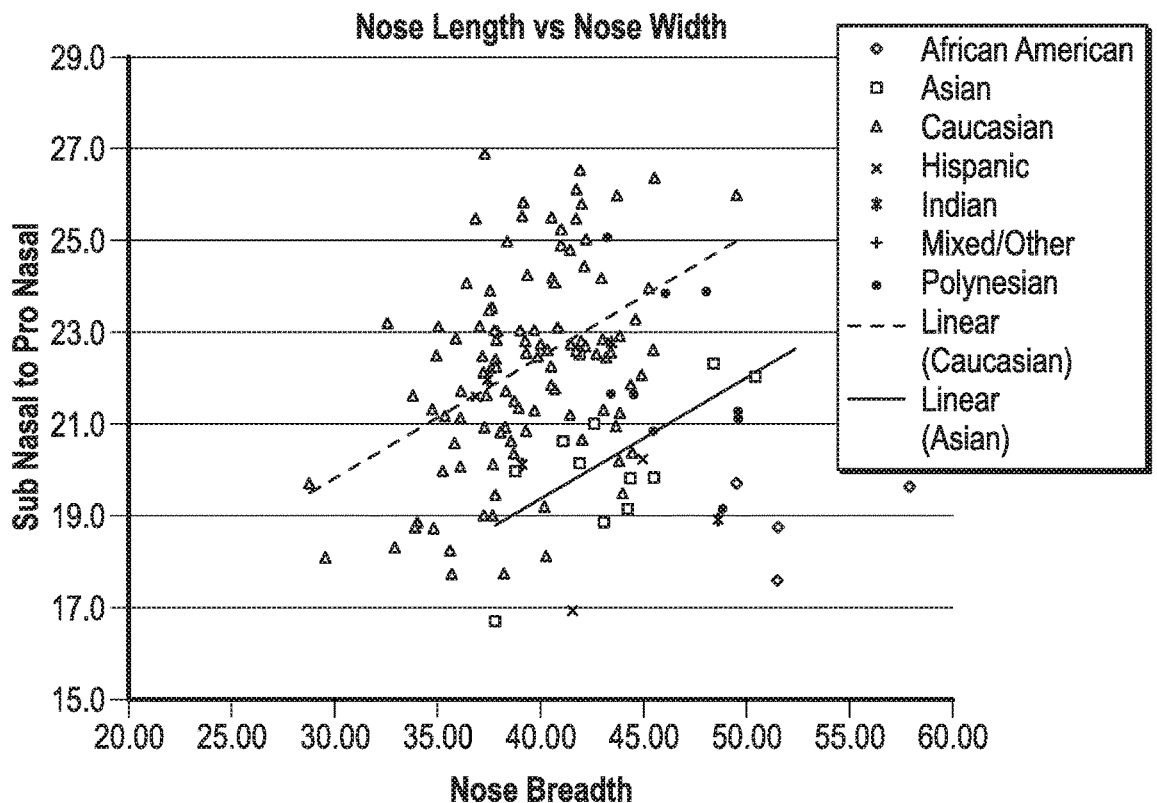
FIG. 34 is the scatter plot of FIG. 33 with linear regressions for certain segments of the data.

In some configurations, both nasal breadth 2212 and nasal length 2214 dimensions are utilized as design inputs into the selection of the overall geometry of the seal 2104 and, in particular, the nasal geometry of the seal 2104. FIG. 34 illustrates a scatter plot of nose breadth 2212 versus nose length 2214 that provides a representation of the variation seen in nasal geometry. The scatter plot data has also been split into different Ethnic groups and shows graphically how nasal geometry also varies between ethnicities.

Figure 35:
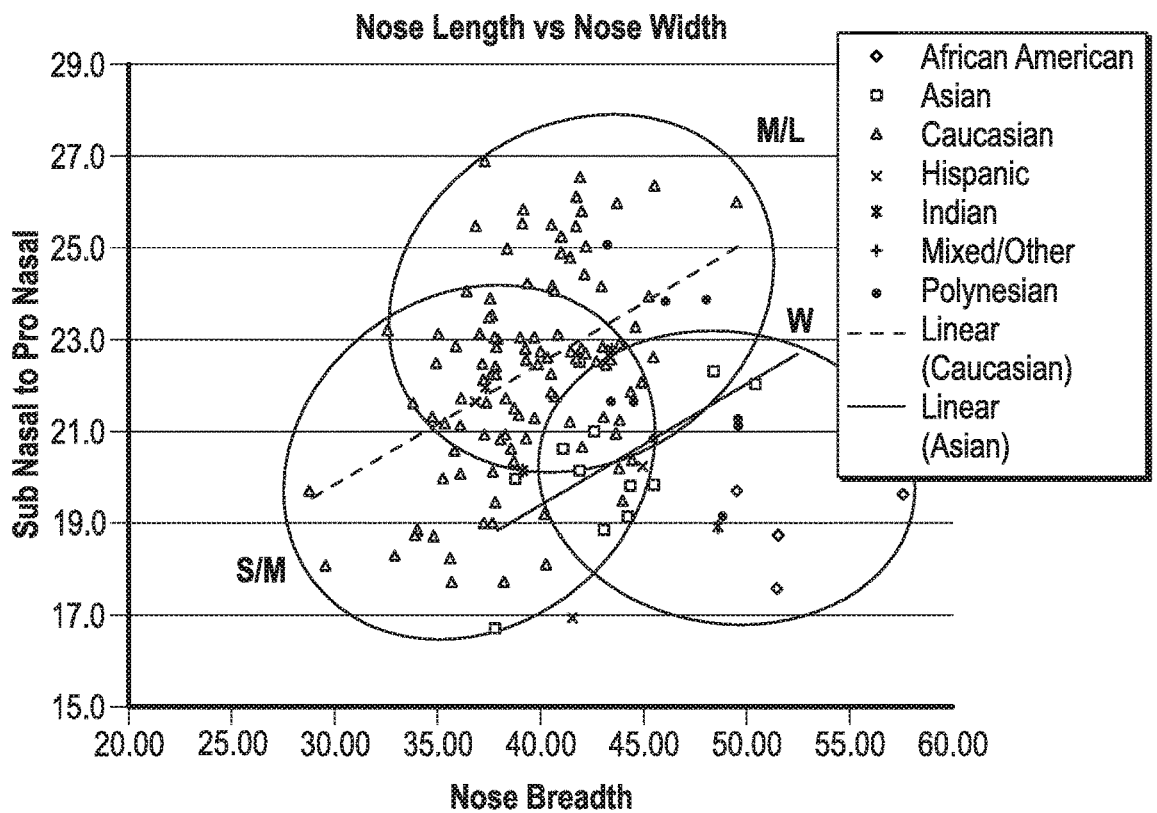
FIG. 35 is the scatter plot of FIGS. 33 and 34 with proposed sizing models represented.

FIG. 35 illustrates the same scatter plot data of FIG. 34, but includes a number of different possible sizing models. The sizing models address both nasal dimensions—nasal breadth or width 2212 and nasal length 2214. Assuming that a maximum number of seal sizes is set to 3, for example, the size ranges could be provided as follows: S/M=small-medium, M/L=medium-large, and W=wide. The coverage of the particular sizes is illustrated by the oval perimeters in FIG. 35. The S/M size covers a portion of the user population having smaller nasal breadths 2212 and nasal lengths 2214. The M/L size covers a portion of the user population having larger nasal breadths 2212 and nasal lengths 2214. As illustrated, in some configurations, there can be some overlap between the S/M size and the M/L size such that a portion of the user population could use either size.

The W size covers a portion of the user population having larger nasal breadths 2212 than either of the S/M and M/L sizes. However, in the illustrated configuration, there is overlap in the coverage of nasal breadths 2212 between the W size and one or both of the S/M and M/L sizes. The W size covers a portion of the user population having nasal lengths 2214 smaller than at least the M/L size. In the illustrated arrangement, the uppermost point of the W size is located at a smaller nasal length 2214 value than the uppermost point of the S/M size. In addition, the lowermost point of the W size is located at a larger nasal length 2214 than the lowermost point of the S/M size; however, in other arrangements or based on other population data, the coverage of the W size could accommodate smaller nasal lengths 2214 than the S/M size or equally small nasal lengths 2214. In addition, as discussed below, additional sizes could also be provided.

Figure 36:
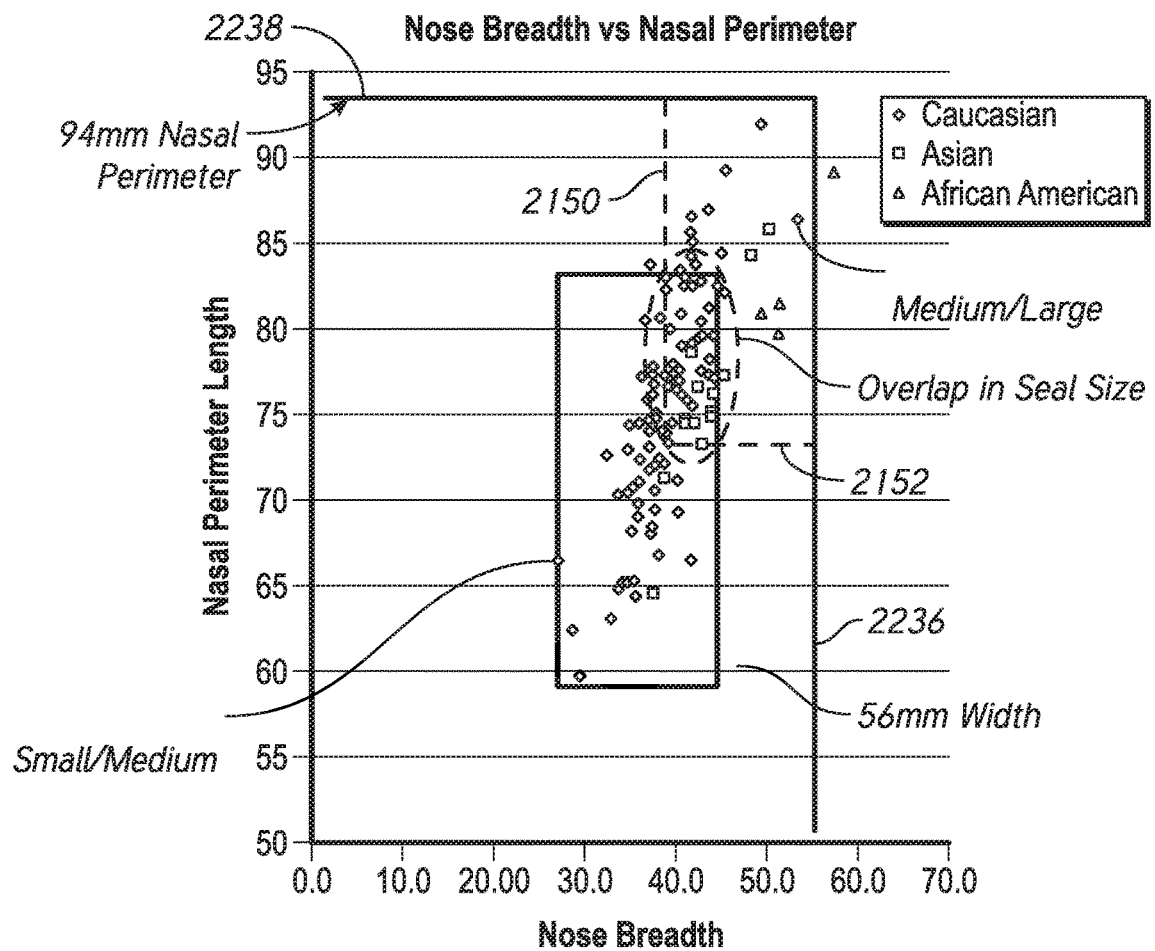
FIG. 36 is a scatter plot of nose breadth versus nasal perimeter length illustrating theoretical populations for two different mask sizes.
Figure 38:
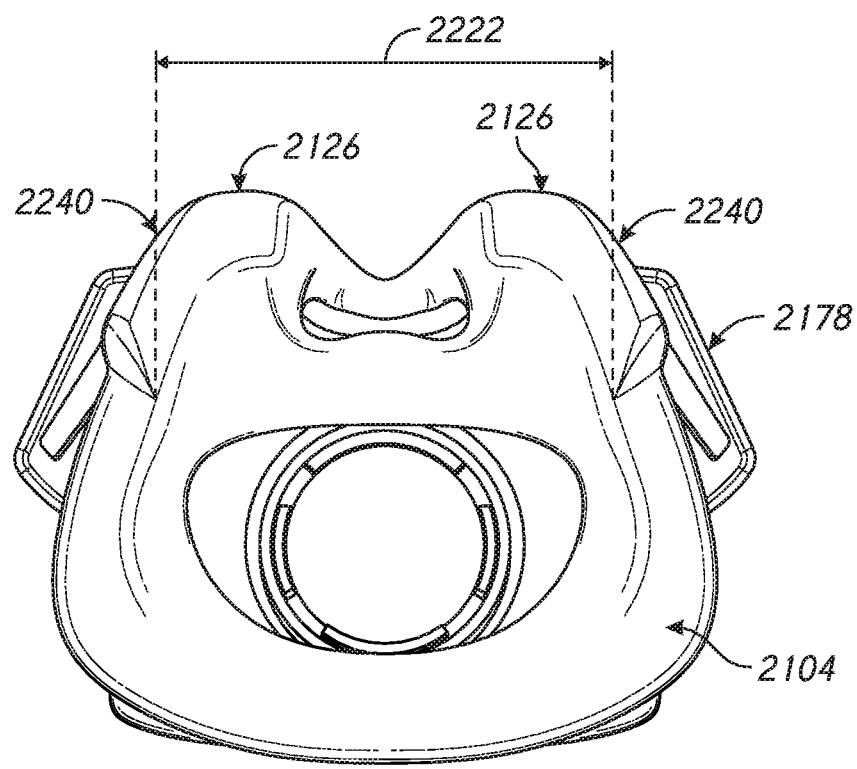
FIG. 38 is a rear view of the mask and frame of FIG. 37.

With reference to the analysis of the small-medium S/M seal 2104 of FIGS. 28 and 32, along with the possible sizing model discussed above, the parameters for the medium-large M/L seal were set. FIG. 36 illustrates possible sizing limits for the M/L size. For example, an upper limit 2236 is set on the nose breadth 2212 based on, for example, a maximum lateral distance 2222 of 56 mm as illustrated in FIG. 38. Similarly, an upper limit 2238 is set on the nasal perimeter length 2210 based on the length of a projected curve of 94 mm (not shown in FIG. 38, but similar to that illustrated in FIG. 28). Lower limits 2150, 2152 can be set on the nose breadth 2212 and nasal perimeter length 2210, respectively, based on the same or other relevant dimensions of the seal 2104.

Figure 37:
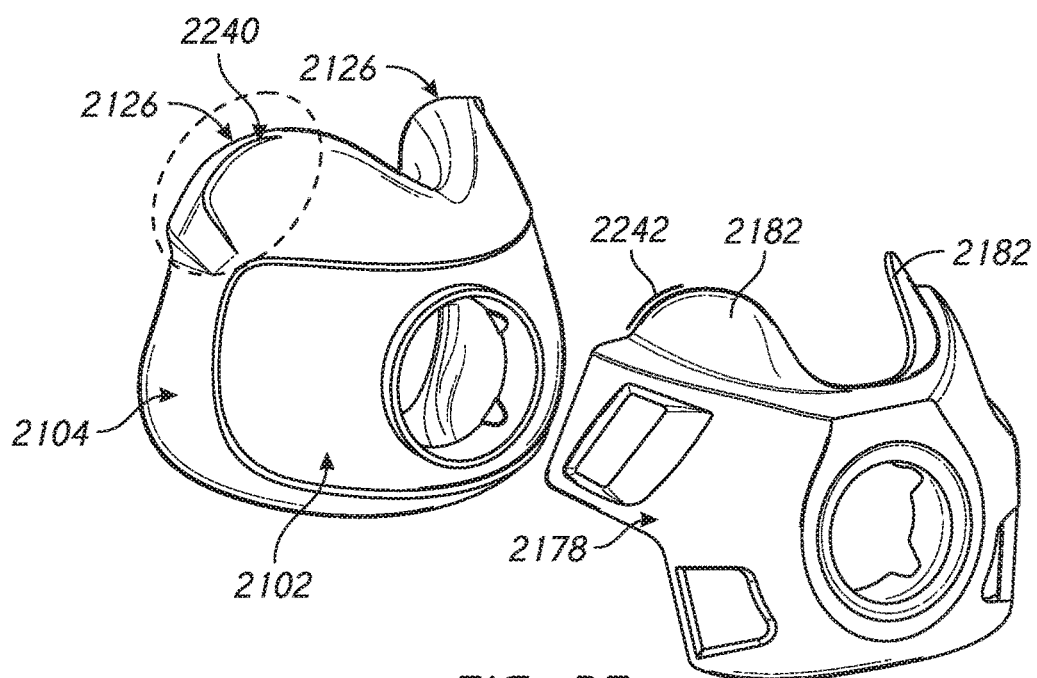
FIG. 37 is an exploded view of a relatively larger mask size and corresponding frame.

In some configurations, the M/L size seal 2104 utilizes the same mask shell (seal housing) 2102 and mask frame 2178 as the S/M size seal 2104 to achieve efficiencies in tooling, inventory, validation and manufacturing cost, for example. In some configurations, to accommodate the extra width of the upper or nasal portion of the M/L seal 2104, the M/L seal 2104 is provided with a protrusion or an outward step 2240 in the outer surface of the upper portion or nasal portion (e.g., in the paddles 2126). In the illustrated arrangement, the outward step 2240 protrudes outwardly toward, to or past a portion 2242 of the frame 2178, as shown in FIG. 37. The portion 2242 of the frame 2178 can be partially or completely defined by a cover 2182 that is configured to provide support to the paddle 2126. Such an arrangement can allow the supports 2163 to be spaced further outwardly from one another than would otherwise be possible without the outward step 2240. Preferably, however, the supports 2163 remain suitably positioned to transfer force to the covers 2182 of the frame 2178. However, in other arrangements, the outward step 2240 can be provided at other locations, can have other shapes, can have other lengths or can have other projecting distances.

Figure 39:
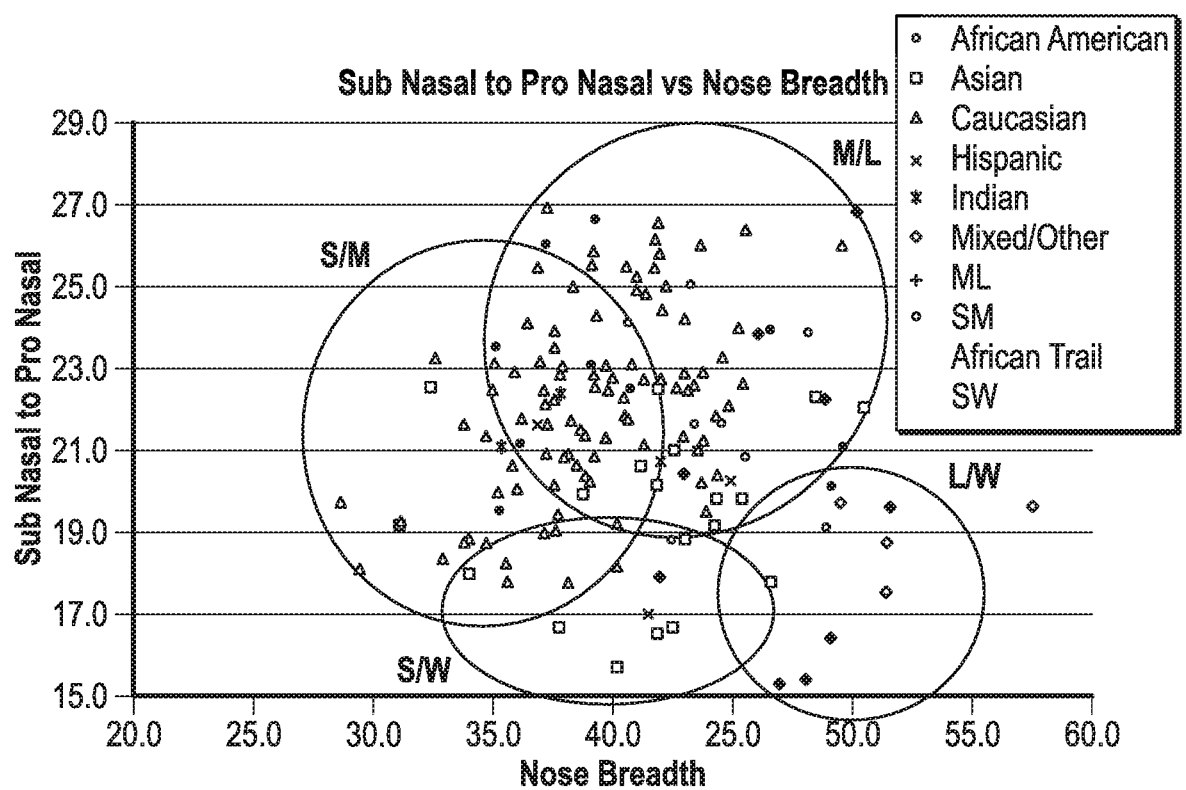
FIG. 39 is a scatter plot of nasal breadth versus nasal length with four proposed sizing models represented.
Figure 40A:
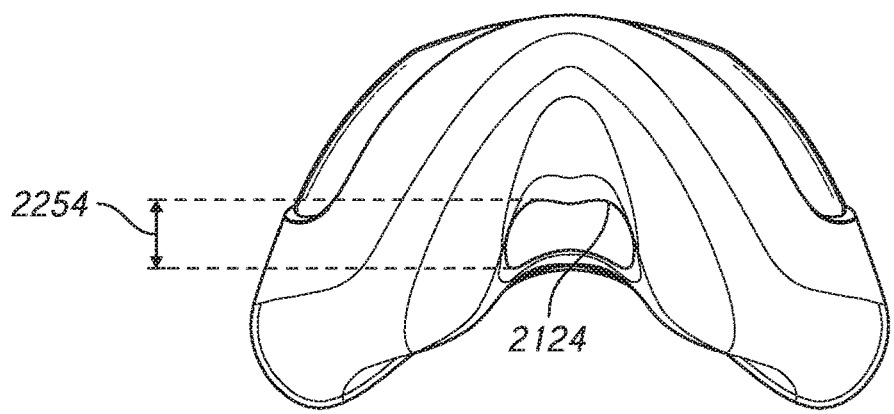
FIG. 40A illustrates a top-down view of a first size of an under-nose seal.
Figure 40B:
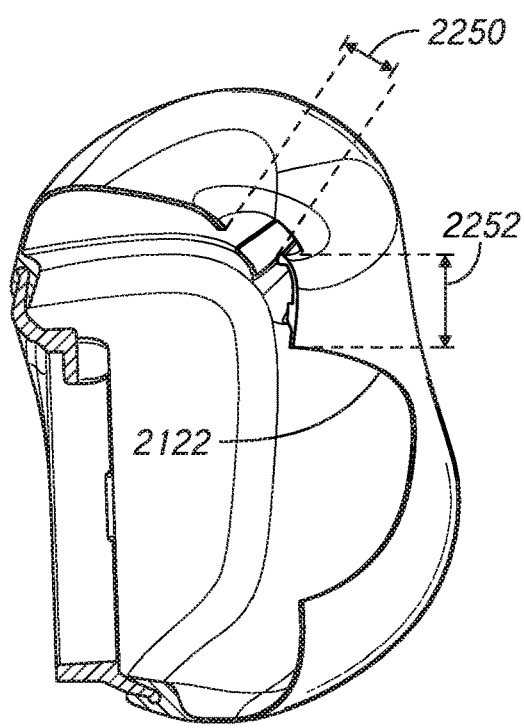
FIG. 40B illustrates a side cross-sectional view of the first size of the under-nose seal in FIG. 40A.
Figure 40C:
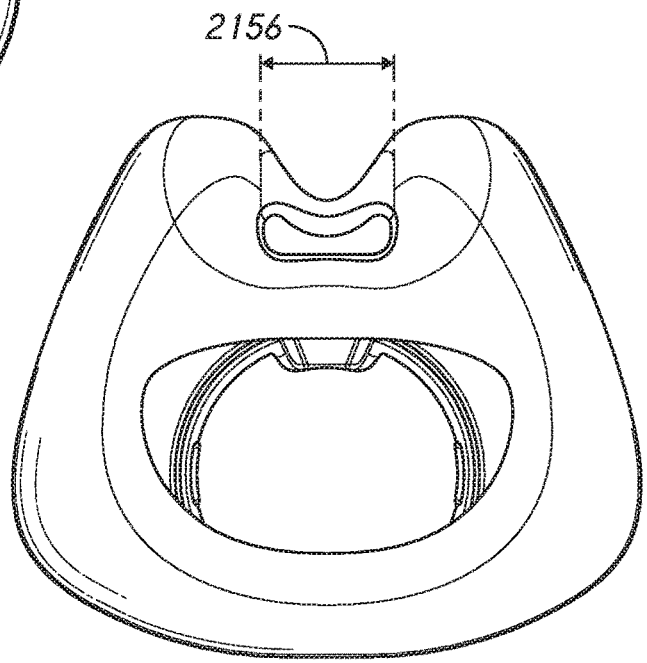
FIG. 40C illustrates a rear view of the first size of the under-nose seal in FIG. 40A.
Figure 41A:
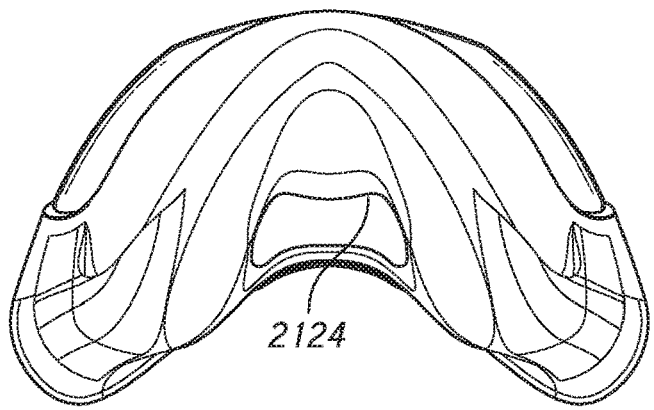
FIG. 41A illustrates a top-down view of a second size of an under-nose seal.
Figure 41B:
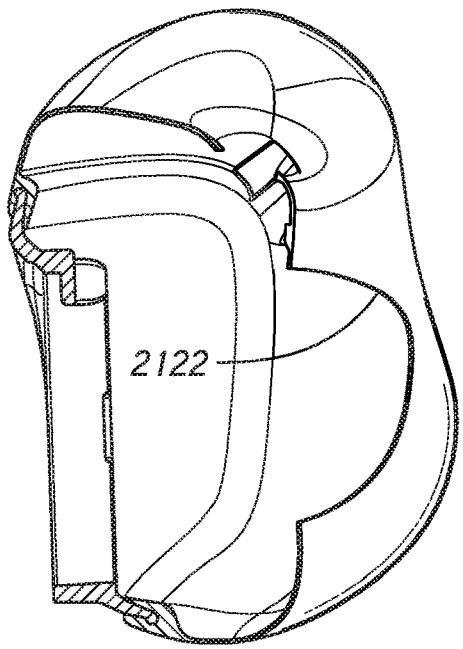
FIG. 41B illustrates a side cross-sectional view of the second size of the under-nose seal in FIG. 41A.
Figure 41C:
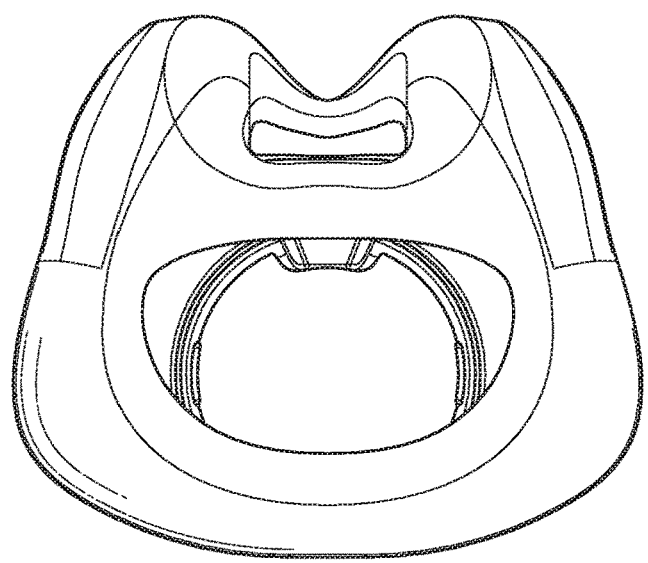
FIG. 41C illustrates a rear view of the second size of the under-nose seal in FIG. 41A.
Figure 42A:
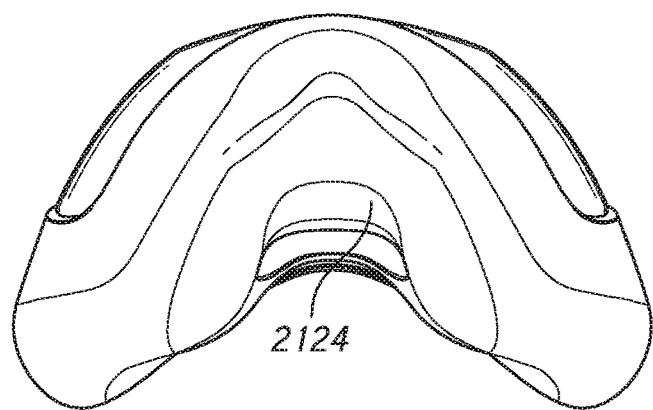
FIG. 42A illustrates a top-down view of a third size of an under-nose seal.
Figure 42B:
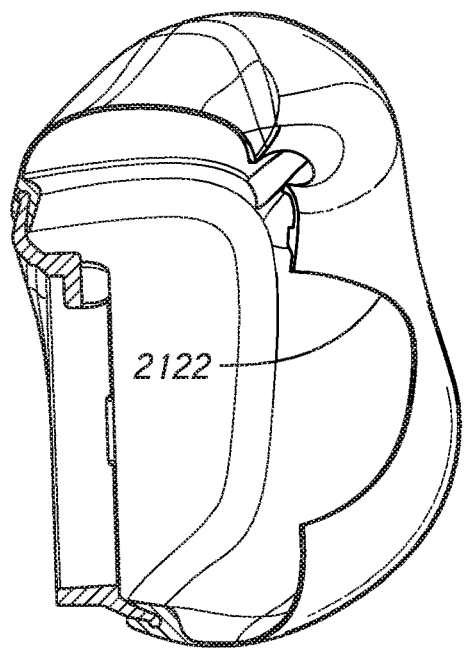
FIG. 42B illustrates a side cross-sectional view of the third size of the under-nose seal in FIG. 42A.
Figure 42C:
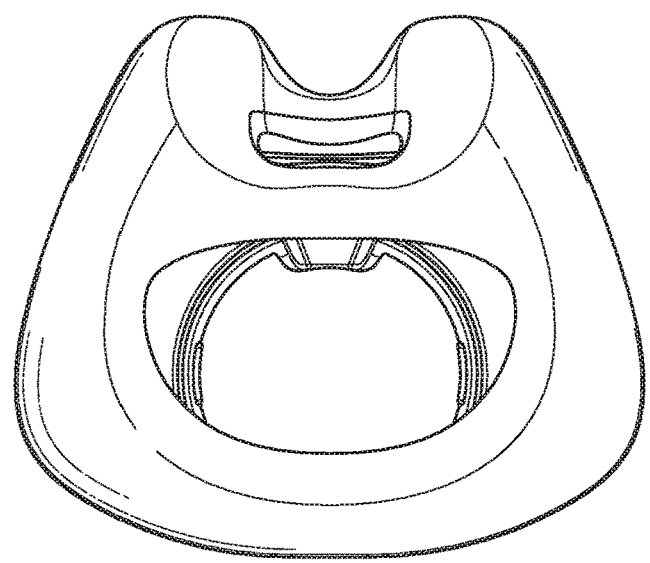
FIG. 42C illustrates a rear view of the third size of the under-nose seal in FIG. 42A.
Figure 43A:
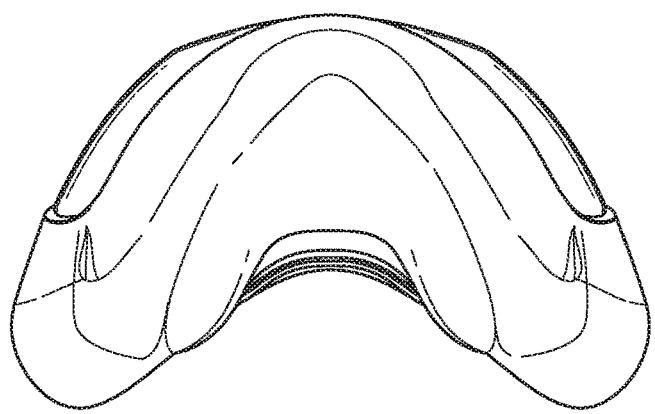
FIG. 43A illustrates a top-down view of a fourth size of an under-nose seal.
Figure 43B:
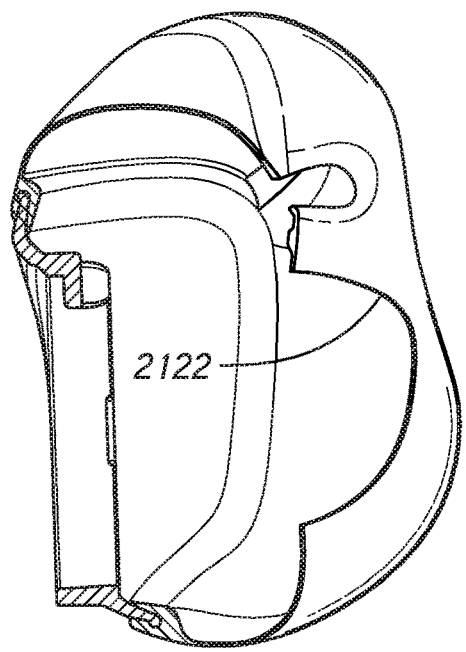
FIG. 43B illustrates a side cross-sectional view of the fourth size of the under-nose seal in FIG. 43A.
Figure 43C:
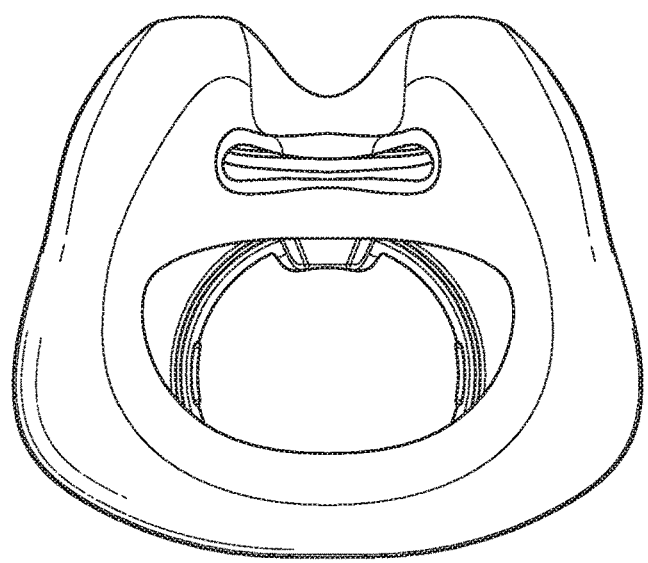
FIG. 43C illustrates a rear view of the fourth size of the under-nose seal in FIG. 43A.

FIG. 39 illustrates a scatter plot nose breadth 2212 versus nose length 2214 similar to that of FIG. 35; however, the scatter plot of FIG. 39 includes four sizes of seal 2104 configured to cover a substantial portion or a substantial entirety of the relevant user population. For example, the size ranges could be provided as follows: S/M=small-medium, M/L=medium-large, short-wide S/W and long-wide L/W=wide. The coverage of the particular sizes is illustrated by the generally circular or oval perimeters in FIG. 39. Similar to the size ranges illustrated in FIG. 35, the S/M size covers a portion of the user population having smaller nasal breadths 2212 and nasal lengths 2214 and the M/L size covers a portion of the user population having larger nasal breadths 2212 and nasal lengths 2214. As illustrated, in some configurations, there can be some overlap between the S/M size and the M/L size such that a portion of the user population could use either size.

The S/W size covers a portion of the user population having larger nasal breadths 2212 than at least a portion of the S/M size. In the illustrated configuration, there is overlap in the coverage of nasal breadths 2212 between the S/W size and one or both of the S/M and M/L sizes. In particular, the coverage of nasal breadths 2212 of the S/W size is subsumed within the coverage of the combination of the S/M and M/L sizes. The S/W size covers a portion of the user population having nasal lengths 2214 smaller than at least the M/L size. In the illustrated arrangement, the uppermost point of the S/W size is located at or near a lowermost point of the M/L size and at a smaller nasal length 2214 value than the uppermost point of the S/M size. In addition, the lowermost point of the S/W size is located at a smaller nasal length 2214 than the lowermost point of the S/M size.

The L/W size covers a portion of the user population having larger nasal breadths 2212 than at least a portion of the S/M size and/or the S/W size. In some configurations, there can be overlap in the coverage of nasal breadths 2212 between the S/W size and the L/W size. The L/W size covers a portion of the user population having nasal lengths 2214 similar to those of the S/W size. In some configurations, the L/W size can cover somewhat larger nasal lengths 2214 than those of the S/W size; however, preferably, the nasal length 2214 coverage of the L/W size is for significantly smaller nasal lengths 2214 than a majority of one or both of the S/M and M/L sizes. In the illustrated arrangement, the uppermost point of the L/W size is located above a lowermost point of each of the S/M size and the M/L size. The relevant dimensions of the seals 2104 (e.g., projected curve 2204, maximum lateral distance 2222, etc.) can be selected to achieve the desired coverages of the different sizes illustrated in FIGS. 35 and 39, among others.

FIGS. 40A-43C illustrate exemplary versions of the S/M, M/L, S/W and L/W size seals 2104. In particular, FIGS. 40A-43C illustrate exemplary dimensions of the nasal opening 2124 and the spacing of the nasal opening 2124 from the oral opening 2122 to illustrate differences between the sizes in addition to those discussed above. The seals 2104 have a maximum linear distance 2250 between forward and rearward edges of the nasal opening 2124 taken along a centreline of the seal 2104. With the seal 2104 oriented substantially vertical in a position as worn by a user with his or her head in an upright position, the maximum linear distance 2250 can be defined by a line that extends upwardly in a rearward to forward direction. The orientation of the line and the upper surface of the nasal portion of the seal 2104 can generally correspond to a typical angle of the underside of the nose for the intended user population.

The seals 2104 also have a linear distance 2252 between an upper edge of the oral opening 2122 and a rearward or lower edge of the nasal opening 2124 taken along a centreline of the seal 2104. The seals 2104 further can have a fore-aft distance 2254 between a forward edge and a rearward edge of the nasal opening 2124 taken along a centreline of the seal 2104. This distance 2254 can be referred to as a length of the nasal opening 2124. However, the length 2254 is not a maximum linear distance between the forward and rearward edges, but the distance as measured in a top view or in a horizontal plane when the seal 2104 is oriented vertically. The seals 2104 can also have a maximum width 2156 of the nasal opening 2124.

The nasal opening maximum linear distance 2250 of the S/M size can be between 5-10 mm, 6-8 mm or can be about 7.36 mm. The nasal opening maximum linear distance 2250 of the M/L size can be between 5-10 mm, 6-8 mm or can be about 7.85 mm. The nasal opening maximum linear distance 2250 of the S/W size can be between 3-7 mm, 4-6 mm or can be about 4.77 mm. The nasal opening maximum linear distance 2250 of the L/W size can be between 2-6 mm, 3-5 mm or can be about 3.7 mm.

The nasal opening-oral opening spacing linear distance 2252 of the S/M size can be between 10-15 mm, 11-13 mm or can be about 12.7 mm. The nasal opening-oral opening spacing linear distance 2252 of the M/L size can be between 10-15 mm, 11-13 mm or can be about 12.2 mm. The nasal opening-oral opening spacing linear distance 2252 of the S/W size can be between 9-14 mm, 10-13 mm or can be about 11.5 mm. The nasal opening-oral opening spacing linear distance 2252 of the L/W size can be smaller than any of the other sizes and, in some cases, can be between 7-12 mm, 8-11 mm or can be about 9.5 mm.

The nasal opening length 2254 of the S/M size can be between 5-10 mm, 6-9 mm or can be about 7.2 mm. The nasal opening length 2254 of the M/L size can be between 5-10 mm, 6-9 mm or can be about 7.1 mm. The nasal opening length 2254 of the S/W size can be between 2-7 mm, 3-6 mm or can be about 3.85 mm. The nasal opening length 2254 of the L/W size can be between 0.5-3 mm, 1-2 mm or can be about 1.6 mm.

The nasal opening width 2156 of the S/M size can be between 15-25 mm, 18-22 mm or can be about 19.7 mm. The nasal opening width 2156 of the M/L size can be between 18-28 mm, 20-26 mm or can be about 23.75 mm. The nasal opening width 2156 of the S/W size can be between 18-28 mm, 20-25 mm or can be about 22.3 mm. The nasal opening width 2156 of the L/W size can be between 25-45 mm, 30-40 mm or can be about 32.9 mm.

Although not explicitly shown for all of the seals 2104, the seals 2104 can also have a height 2158 of the nasal opening 2124 taken along the centreline of the seal 2104 in a vertical plane when the seal is oriented vertically. The height 2158 of the L/W size can be between 6-12 mm, 7-10 mm or can be about 8.63 mm.

The above-described dimensions are exemplary only. Other dimensions are possible in view of the sizing methodology disclosed herein. Moreover, the disclosure includes not only the particular dimensions and ranges, but the proportions and relative dimensions between the sizes. In addition, the oral openings 2122 can be relatively constant across the various sizes.

Figure 44:
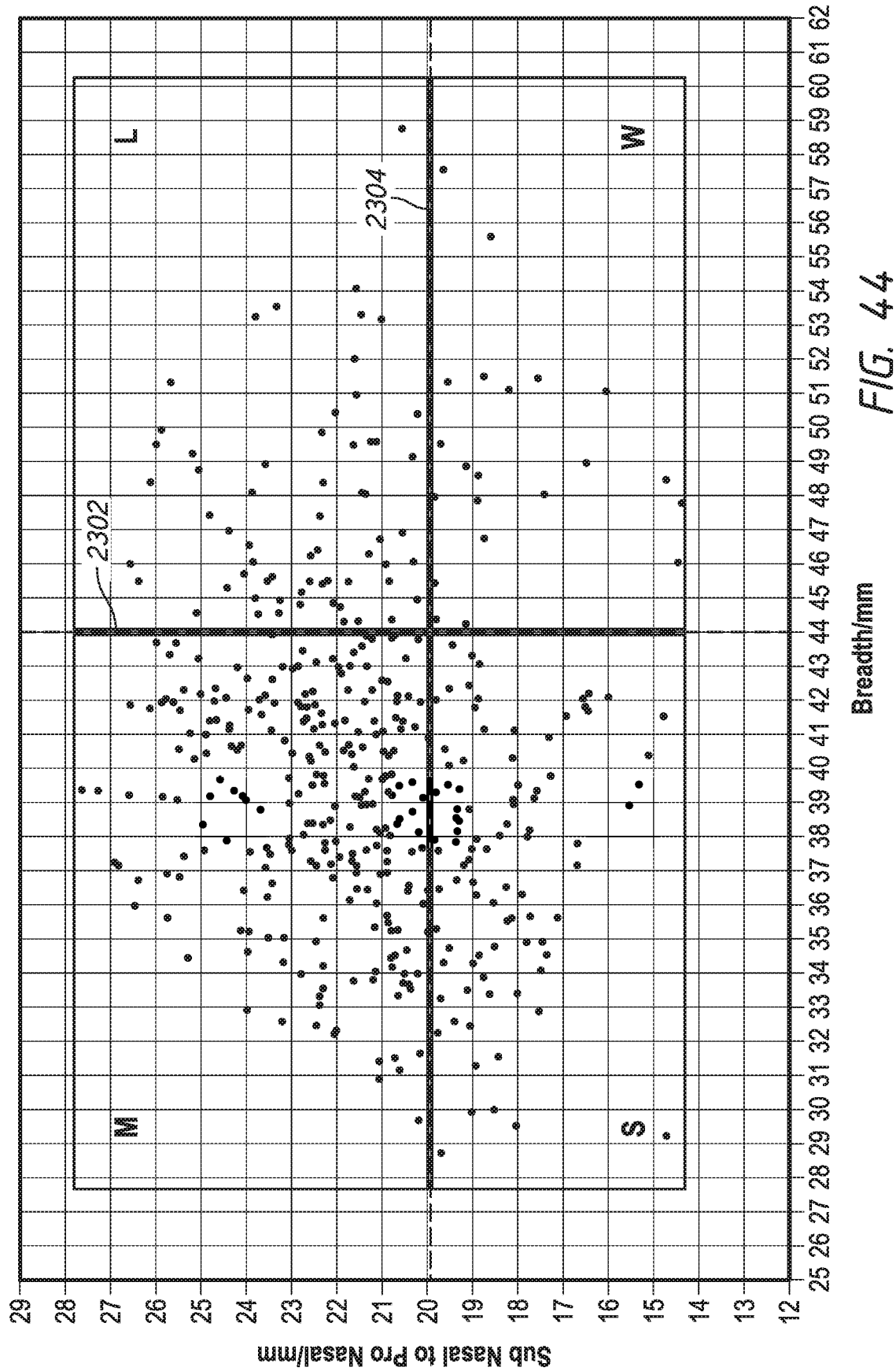
FIG. 44 is a scatter plot of nose breadth versus nasal length illustrating a theoretical ethnically diverse population with proposed sizing models represented that will fit an under-nose seal.

FIG. 44 illustrates a seal sizing coverage arrangement based on a scatter plot of nose breadth 2212 versus nose length 2214. The data illustrated in the scatter plot is a collection of facial measurements that provides a representation of the variation seen in nasal geometry of a sample population. The data includes sizing information of user from different Ethnic groups and shows graphically the wide variance of facial or nasal geometry when considering a population sample that includes different ethnicities. The scatter plot data has been divided into different possible sizing models for a nasal under-nose interface. The sizing models address both nasal dimensions—nasal breadth or width 2212 and nasal length 2214. Assuming that a maximum number of seal sizes is set to 4, for example, the seal size ranges could be provided as follows: M=medium, L=large, short=S and W=wide. The coverage of the particular seal sizes is illustrated by the rectangular perimeters, as shown in FIG. 44.

To provide nasal under-the-nose interface sizing coverage of a substantially majority of the sample population, the scatter plot is divided into quadrants wherein each quadrant is covered by a seal size. That is, each size (i.e., M, L, S and W) generally corresponds to a quadrant. In other words, the boundaries of coverage provided by each size are defined by the quadrants. The scatter plot of the sample population is divided by a nasal length crossover axis 2302 (i.e., also referred to as the short/wide crossover axis) and a nasal width crossover axis 2304 (i.e., also be referred to as the large/wide crossover axis). That is, the quadrants are defined by a nasal length crossover axis 2302 and a nasal width crossover axis 2304. The ranges of nasal widths covered by the M and L sizes, respectively, are defined by the nasal width crossover axis 2304. The ranges of nasal widths covered by the S and W sizes, respectively, are also defined by the nasal width crossover axis 2304. Similarly, the ranges of nasal lengths covered by the S and M sizes, respectively, are defined by the nasal length crossover axis 2302. The ranges of nasal lengths covered by the W and L sizes, respectively, are also defined by the nasal length crossover axis 2302. Accordingly, the M and L sizes cover substantially the entire range of nasal widths of the sample population. Similarly, the S and W sizes also cover substantially the entire range of nasal widths of the sample population. Further, the S and M sizes cover substantially the entire range of nasal lengths of the sample population. Similarly, the W and L sizes cover substantially the entire range of nasal lengths of the sample population.

As shown in FIG. 44, the sample population provides a range of nasal widths that spans from approximately 27.8 to 60.2 mm. The sample population provide a range of nasal lengths that spans from approximately 14.3 to 27.7 mm. The nasal width crossover axis 2304 is positioned at approximately a median of the range of nasal widths. As shown, the nasal width crossover axis 2304 is positioned at approximately 44.0 mm. The nasal length crossover axis 2302 is positioned at a nasal length less than the median of the sample population. As shown, the nasal length crossover axis 2302 is positioned at approximately 20.0 mm or approximately 40% of the range of nasal lengths (i.e., $40^{th}$ percentile of the population sample). The crossover axes 2302, 2304 may be positioned according to the distribution of sizes of the sample population such that a greater number of users are covered by a particular size or sizes. For example, the positioning of each axis 2302, 2304 may be positioned according to the population distribution to adjust the range of coverage such that a greater or smaller number of users are covered by a particular size.

As illustrated in FIG. 44, the M size is configured to fit users having the smallest nasal widths to users having nasal widths substantially near the median. That is, as shown, the M size fits users having nasal widths of approximately 27.8 to 44.0 mm. The L size is configured to fit users having nasal widths substantially near the median to users having the largest nasal widths. That is, as shown, the L size fits users having nasal widths of approximately 44.0 to 60.2 mm. Accordingly, the combination of M and L sizes cover substantially the entire range of nasal widths.

Similarly, the S size is configured to fit users having the smallest nasal widths to users having nasal widths substantially near the median. That is, as shown, the S size fits users having nasal widths of approximately 27.8 to 44.0 mm. The W size is configured to fit users having nasal widths substantially near the median to users having the largest nasal widths. That is, as shown, the W size fits users having nasal widths of approximately 44.0 to 60.2 mm. Accordingly, the combination of S and W sizes cover substantially the entire range of nasal widths. Further, as shown, the range of nasal widths covered by the S size is substantially equal to or aligned with the range of nasal width covered by the M size. Similarly, the range of nasal width covered by the L size is substantially equal to or aligned with the range of nasal widths covered by the W size.

The S size is configured to fit users having the smallest nasal length to users having nasal lengths near the short/wide crossover axis 2304 (i.e., $40^{th}$ percentile). That is, as shown, the S size fits users having nasal lengths of approximately 14.3 to 20.0 mm. The M size is configured to fit users having nasal lengths near the short/wide crossover axis 2304 to users having the largest nasal lengths. That is, as shown, the M size fits users having nasal lengths of approximately 20.0 to 27.7 mm. Accordingly, the S and M sizes cover substantially the entire range of nasal lengths.

Similarly, the W size is configured to fit users having the smallest nasal length to users having nasal lengths near the short/wide crossover axis 2304 (i.e., $40^{th}$ percentile). That is, as shown, the W size fits users having nasal lengths of approximately 14.3 to 20.0 mm. The L size is configured to fit users having nasal lengths near the short/wide crossover axis 2304 to users having the largest nasal lengths. That is, as shown, the L size fits users having nasal lengths of approximately 20.0 to 27.7 mm. Accordingly, the W and L sizes cover substantially the entire range of nasal widths. Further, as shown, the range of nasal length covered by the S size is substantially equal to or aligned with the range of nasal length covered by the W size. Similarly, the range of nasal length covered by the M size is substantially equal to or aligned with the range of nasal widths covered by the L size.

Accordingly, the nasal opening maximum linear distance 2250 of the M size can be between 5-10 mm, 6-8 mm or can be about 7.36 mm. The nasal opening maximum linear distance 2250 of the L size can be between 5-10 mm, 6-8 mm or can be about 7.85 mm. The nasal opening maximum linear distance 2250 of the S size can be between 3-7 mm, 4-6 mm or can be about 4.77 mm. The nasal opening maximum linear distance 2250 of the W size can be between 2-6 mm, 3-5 mm or can be about 3.7 mm.

The nasal opening length 2254 of the M size can be between 5-10 mm, 6-9 mm or can be about 7.2 mm. The nasal opening length 2254 of the L size can be between 5-10 mm, 6-9 mm or can be about 7.1 mm. The nasal opening length 2254 of the S size can be between 2-7 mm, 3-6 mm or can be about 3.85 mm. The nasal opening length 2254 of the W size can be between 0.5-3 mm, 1-2 mm or can be about 1.6 mm.

The nasal opening width 2156 of the M size can be between 15-25 mm, 18-22 mm or can be about 19.7 mm. The nasal opening width 2156 of the L size can be between 18-28 mm, 20-26 mm or can be about 23.75 mm. The nasal opening width 2156 of the S size can be between 18-28 mm, 20-25 mm or can be about 22.3 mm. The nasal opening width 2156 of the W size can be between 25-45 mm, 30-40 mm or can be about 32.9 mm.

As a result of the seal sizing coverage arrangement provided by dividing the scatter plot into quadrants, users of a variety of ethnicities may comfortably fit one of the M, L, S and W sizes. Particularly, users of ethnicities having nasal measurements at the outermost extents of the ranges may be comfortably fit by one of the M, L, S and W sizes. As shown, the size S may cover users and ethnicities having shorter nasal lengths and shorter nasal widths. Similarly, the size W may cover users and ethnicities having shorter nasal lengths and longer nasal widths. The size M may cover users and ethnicities having longer nasal lengths and shorter nasal widths. The size L may cover users and ethnicities having longer nasal lengths and longer nasal widths. It should be understood to one of ordinary skill in the art that the nasal length crossover axis 2302 and nasal width crossover axis 2304 may be positioned according to the distribution of sizes of the sample population such that a greater number of users are covered by a particular size or sizes.

Figure 45:
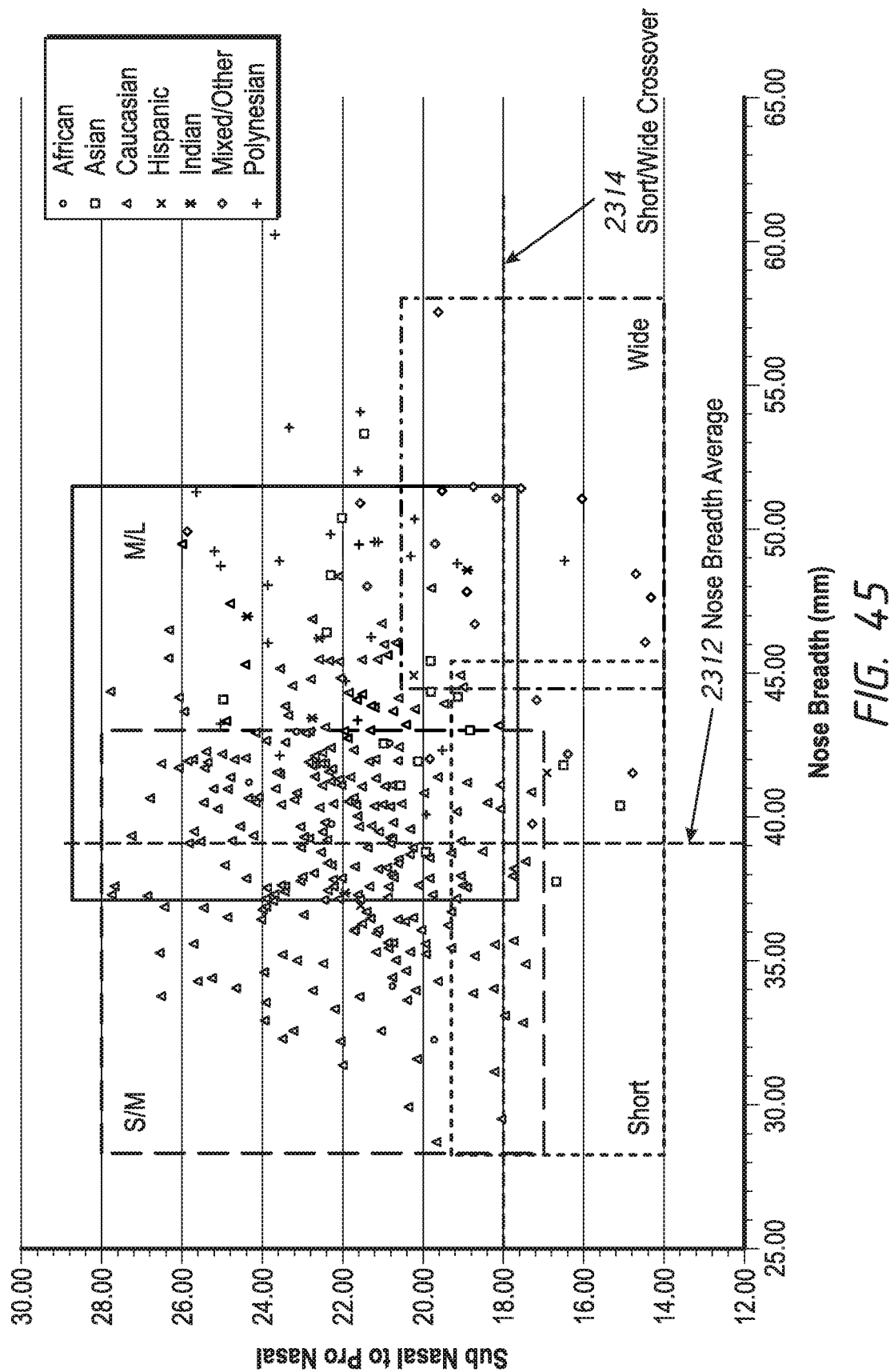
FIG. 45 is a scatter plot of nose breadth versus nasal length illustrating a theoretical ethnically diverse population with proposed sizing models represented that will fit an over-nose seal.
Figure 46:
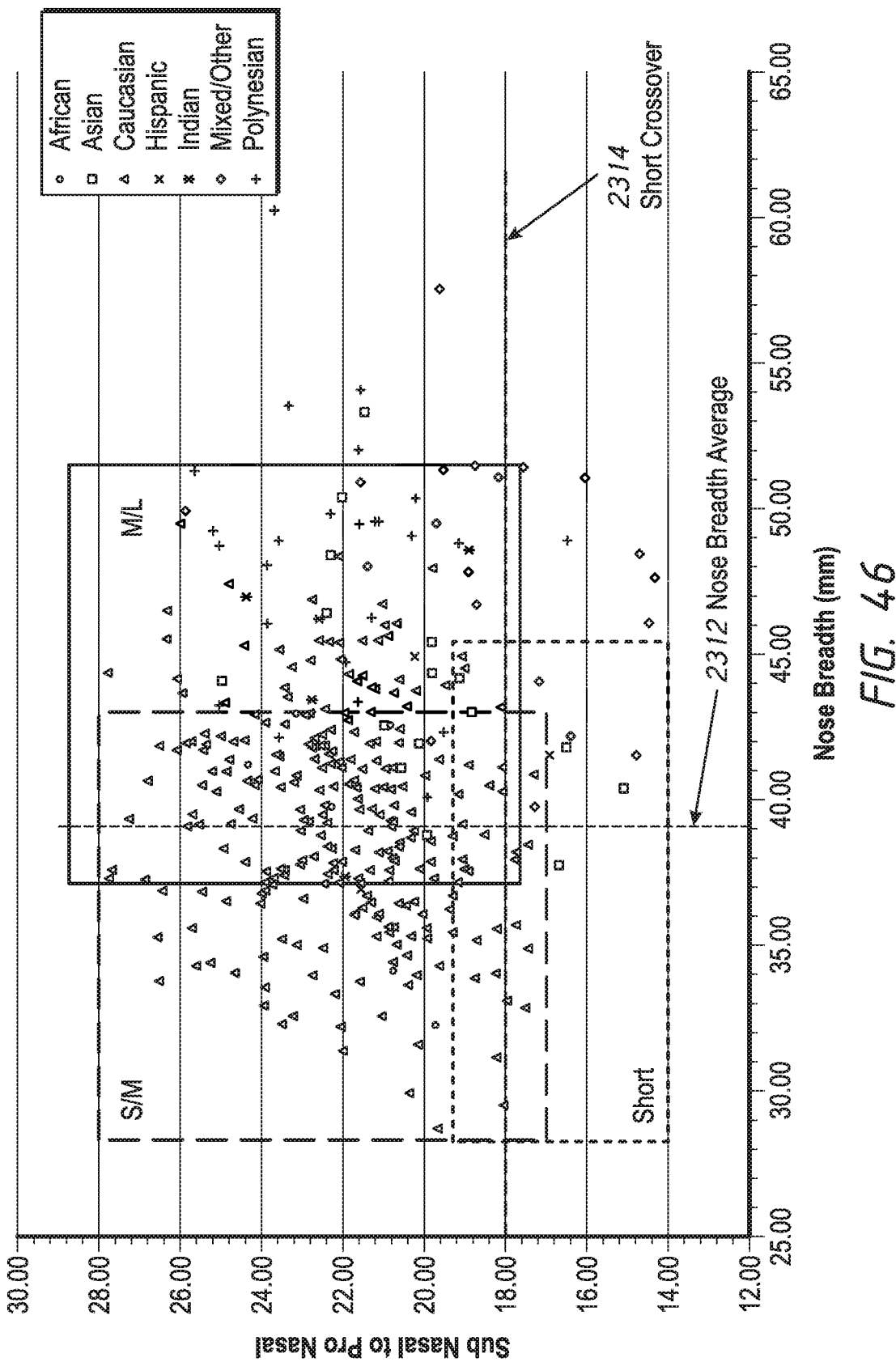
FIG. 46 is a scatter plot of nose breadth versus nasal length illustrating a theoretical ethnically diverse population with alternative proposed sizing models represented that will fit an over-nose seal.
Figure 47:
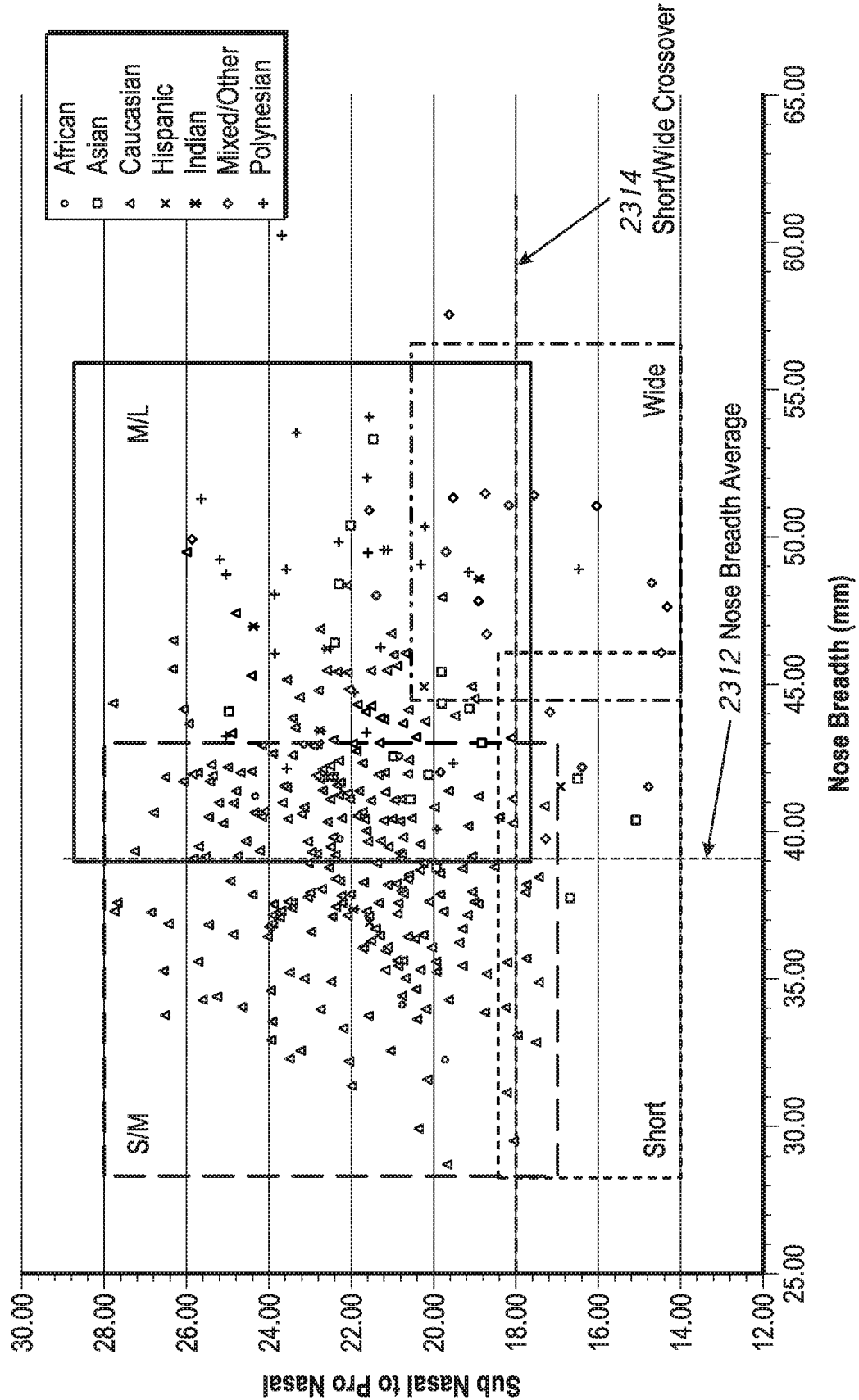
FIG. 47 is a scatter plot of nose breadth versus nasal length illustrating a theoretical ethnically diverse population with alternative proposed sizing models represented that will fit an over-nose seal.

FIGS. 45-47 also illustrate different sizing coverage arrangements for a population sample that includes different ethnicities. The population sample is represented by a scatter plot of nose breadth 2212 versus nose length 2214. The sizing coverage arrangements in FIG. 45 divide the scatter plot data into different possible sizing models for an over-nose interface. The sizing models address both nasal dimensions—nasal breadth or width 2212 and nasal length 2214. Assuming that a maximum number of seal sizes is set to 4, for example, the seal size ranges could be provided as follows: S/M=small-medium, M/L=medium-large, Short and Wide. The coverage of the particular seal sizes is illustrated by the rectangular perimeters.

Similar to FIG. 44, the sizing coverage arrangement of FIG. 45 divides the sample population into quadrants. However, in contrast to FIG. 44, the boundaries of coverage provided by each size are not defined by the quadrants. That is, FIG. 45 shows the sample population divided into quadrants by axes (illustrated in dashed lines) but the axes do not define the extents or range of nasal lengths/widths covered by each size. Instead, the extents or range of nasal lengths/widths covered by each size are determined based on the population intended to be accommodated by a given size. Further, the boundaries of coverage provided by at least one size may overlap the boundaries of coverage of another size. Accordingly, it is possible for users that are between sizes to comfortable fit multiple seal sizes. Further, the sizes may be configured such that users having a common size may have the option of wearing more than one size.

As shown in FIG. 45, the sample population provide a range of nasal widths that spans from approximately 28.8 mm to 57.7 mm. The sample population provide a range of nasal lengths that spans from approximately 14.3 mm to 27.8 mm. FIG. 45 shows a Nose Breadth Average Axis 2312 is positioned at the nose breadth average (approximately 39.1 mm) and a Short/Wide Crossover Axis 2314 positioned at approximately 30% of the range of nasal lengths (approximately 18.0 mm).

The S/M size is configured to fit users having substantially the smallest nasal widths to users having nasal widths greater than the average nasal width. That is, as shown, the S/M size fits users having nasal widths of approximately 28.8 to 43.0 mm. The M/L size is configured to fit users having nasal widths less than the average nasal width to users having nasal widths greater than the average nasal width. That is, as shown, the M/L size fits users having nasal widths of approximately 37.2 to 51.5 mm. Accordingly, S/M and M/L sizes provide overlapping coverage of a range of nasal widths between approximately 37.2 to 43.0 mm. That is, the S/M and M/L sizes provide overlapping coverage for users having a common nasal width size. As shown, the overlapping coverage includes sizes near the Nose Breadth Average Axis 2312. Therefore, as shown, a large number of the sample population (i.e., who have average, median or common nasal width) may be properly fitted with both the S/M and M/L sizes. Also, as shown in FIG. 45, the combination of the S/M and M/L sizes do not cover the entire range of nasal widths.

Further, a difference between the average and/or median values of the range of nose lengths covered by the S/M and M/L sizes is less than the difference between the average values of the range of nasal width covered by the S/M and M/L sizes. That is, when comparing the S/M and M/L sizes, the average and/or median nasal width of the M/L size is increased or offset by a greater amount than the increase of average and/or median nose lengths. In other words, a difference between the average and/or median nasal width between the S/M and M/L sizes is greater than a difference between the average and/or median nose length between the S/M and M/L sizes. This is in contrast to a general scaling up of both the nasal width and the nose lengths by the same factor or multiplier. Accordingly, the ranges of nasal width and nose lengths between the S/M and M/L sizes are each offset by different amounts and/or percentages. It should be understood by one of ordinary skill in the art that, in other configurations, the average and/or median nasal width of the M/L size may be increased or offset by a smaller amount than the amount of increase of the average and/or median nose lengths.

The Short size is configured to fit users having substantially the smallest nasal widths to users having nasal widths greater than the average nasal width. That is, as shown, the Short size fits users having nasal widths of approximately 28.8 to 45.5 mm. The Wide size is configured to fit users having nasal widths less than the average nasal to users having nasal widths greater than the average nasal width. That is, as shown, the Wide size fits users having nasal widths of approximately 44.5 to 58.0 mm. Accordingly, the Short and Wide sizes provide overlapping coverage of a range of nasal widths between approximately 44.5 to 45.5 mm. That is, the Short and Wide sizes provide overlapping coverage for users having nasal widths greater than the average nasal width. Further, the combination of the Short and Wide sizes covers substantially the entire range of nasal widths. In contrast to the nasal width range provided by the S/M and M/L sizes, the Short and Wide sizes cover a broader or wider range of nasal widths.

The Short size is configured to fit users having the smallest nasal lengths to users having nasal lengths greater than the Short/Wide Crossover Axis 2314 (i.e., at approximately 30% of the range of nasal lengths). That is, as shown, the Short size fits users having nasal lengths between approximately 14.0 to 19.2 mm. The S/M size is configured to fit users having nasal lengths less than the Short/Wide Crossover Axis 2314 to users having the largest nasal lengths. That is, as shown, the S/M size fits users having nasal lengths of approximately 17.0 to 28.0 mm. Accordingly, Short and S/M sizes provide overlapping coverage of a range of nasal lengths between approximately 17.0 to 19.2 mm. Further, the combination of the Short and S/M sizes cover substantially the entire range of nasal lengths.

The Wide size is configured to fit a range of users having the smallest nasal lengths to users having nasal lengths greater than the Short/Wide Crossover Axis 2314 (i.e., at approximately 30% of the range of nasal lengths). That is, as shown, the Wide size fits users having nasal lengths between approximately 14.0 to 20.4 mm. The M/L size is configured to fit users having nasal lengths less than the Short/Wide Crossover Axis 2314 to users having the largest nasal lengths. That is, as shown, the M/L size fits users having nasal lengths of approximately 17.6 to 28.8 mm. Accordingly, Wide and M/L sizes provide overlapping coverage of a range of nasal lengths between approximately 17.6 to 20.4 mm. Further, the combination of the Wide and M/L sizes cover substantially the entire range of nasal lengths. Even further, the S/M and M/L sizes provide overlapping coverage of a range of nasal length between approximately 17.6 to 28.0 mm. That is, the S/M and M/L sizes provide overlapping coverage for users having a common nasal length size. Therefore, as shown, a large number of the sample population (i.e., who have average, median or common nasal length) may be properly fitted with both the S/M and M/L sizes.

Based on the sizing coverage illustrated in FIG. 45, the nasal opening maximum linear distance 2250 of the S/M size can be between 5-10 mm, 6-8 mm or can be about 7.38 mm. The nasal opening maximum linear distance 2250 of the M/L size can be between 5-10 mm, 6-8 mm or can be about 7.75 mm. The nasal opening maximum linear distance 2250 of the Short size can be between 3-7 mm, 4-6 mm or can be about 4.70 mm. The nasal opening maximum linear distance 2250 of the Wide size can be between 2-6 mm, 3-5 mm or can be about 3.60 mm.

Based on the sizing coverage illustrated in FIG. 45, the nasal opening-oral opening spacing linear distance 2252 of the S/M size can be between 10-15 mm, 11-13 mm or can be about 12.67 mm. The nasal opening-oral opening spacing linear distance 2252 of the M/L size can be between 10-15 mm, 11-13 mm or can be about 12.2 mm. The nasal opening-oral opening spacing linear distance 2252 of the Short size can be between 9-14 mm, 10-13 mm or can be about 11.46 mm. The nasal opening-oral opening spacing linear distance 2252 of the Wide size can be smaller than any of the other sizes and, in some cases, can be between 7-12 mm, 8-11 mm or can be about 8.67 mm.

Based on the sizing coverage illustrated in FIG. 45, the nasal opening length 2254 of the S/M size can be between 5-10 mm, 6-9 mm or can be about 6.86 mm. The nasal opening length 2254 of the M/L size can be between 5-10 mm, 6-9 mm or can be about 7.07 mm. The nasal opening length 2254 of the Short size can be between 2-7 mm, 3-6 mm or can be about 3.86 mm. The nasal opening length 2254 of the Wide size can be between 0.5-3 mm, 1-2 mm or can be about 1.58 mm.

Based on the sizing coverage illustrated in FIG. 45, the nasal opening width 2156 of the S/M size can be between 15-25 mm, 18-22 mm or can be about 19.7 mm. The nasal opening width 2156 of the M/L size can be between 18-28 mm, 20-26 mm or can be about 23.72 mm. The nasal opening width 2156 of the Short size can be between 18-28 mm, 20-25 mm or can be about 22.28 mm. The nasal opening width 2156 of the Wide size can be between 25-45 mm, 30-40 mm or can be about 32.30 mm.

In FIG. 46, the illustrated sizing coverage is similar to the sizing coverage illustrated in FIG. 45 except that a maximum number of seal sizes is set to 3. For example, the seal size ranges could be provided as follows: S/M=small-medium, M/L=medium-large and Short. That is, a fourth size (i.e., the Wide size in FIG. 45) is not provided by the sizing coverage illustrated in FIG. 46. The nasal lengths and widths covered by the S/M, M/L and Short sizes are substantially similar to those described in reference to FIG. 45. Accordingly, the geometry and configuration of the nasal opening for the S/M, M/L and Short seal sizes is also substantially similar to those described in reference to FIG. 45.

FIG. 47 illustrates a seal sizing coverage arrangement similar to FIG. 45. That is, the maximum number of seal sizes is set to 4, for example, the seal size ranges could be provided as follows: S/M=small-medium, M/L=medium-large, Short and Wide. The sizing arrangement in FIG. 47 differs from FIG. 45 in that the range of nasal width coverage of the S/M, M/L and Short sizes are broadened. Further, the range of nasal width coverage of the Wide size is narrowed compared to FIG. 45. Still further, the range of nasal length coverage of the Short size is also narrowed compared to FIG. 45.

More specifically, the S/M size is configured to fit users having substantially the smallest nasal widths to users with nasal widths greater than the average nasal width. That is, as shown, the S/M size fits users having nasal widths of approximately 28.8 to 46.0 mm (compared to approximately 28.8 to 43.0 mm in FIG. 45). The M/L size is configured to fit users having nasal widths substantially equal to the average nasal breadth to users with nasal widths greater than the average nasal width. That is, as shown, the M/L size fits users having nasal widths of approximately 39.0 to 56.0 mm (compared to approximately 37.2 to 51.5 mm in FIG. 45). Accordingly, S/M and M/L provide overlapping coverage of a range of nasal widths between approximately 39.0 to 46.0 mm (compared to approximately 37.2 to 43.0 mm in FIG. 45). Further, the combination of the S/M and M/L sizes substantially cover the entire range of nasal widths.

The Short size is configured to fit users having substantially the smallest nasal widths to users with nasal widths greater than the average nasal width. That is, as shown, the Short size fits users having nasal widths of approximately 28.8 to 46.0 mm. The Short size may fit a range of nasal widths similar to the S/M size. The Wide size is configured to fit users having nasal widths less than the average nasal width to users with nasal widths greater than the average nasal width. That is, as shown, the Wide size fits users having nasal widths of approximately 44.5 to 56.5 mm (compared to approximately 44.5 to 58.0 mm in FIG. 45). Accordingly, Short and Wide sizes provide overlapping coverage of a range of nasal widths between approximately 44.5 to 46.0 mm (compared to approximately 44.5 to 45.5 mm in FIG. 45). Further, the combination of Short and Wide sizes cover substantially the entire range of nasal widths similar to the S/M and M/L sizes.

The Short size is configured to fit users having the smallest nasal lengths to users with nasal lengths greater than the Short/Wide Crossover Axis 2314 (i.e., at approximately 30% of the range of nasal lengths). That is, as shown, the Short size fits users having nasal lengths between approximately 14.0 to 18.4 mm (compared to approximately 14.0 to 19.2 mm in FIG. 45). The S/M size is configured to fit users having nasal lengths less than the Short/Wide Crossover Axis 2314 to users having the largest nasal lengths. That is, as shown, the S/M size fits users having nasal lengths of approximately 17.0 to 28.0 mm (compared to approximately 17.0 to 28.0 mm in FIG. 45). Accordingly, Short and S/M sizes provide overlapping coverage of a range of nasal lengths between approximately 17.0 to 18.4 mm (compared to approximately 17.0 to 19.2 mm in FIG. 45). Further, the combination of the Short and S/M sizes cover substantially the entire range of nasal lengths.

The Wide size is configured to fit users having the smallest nasal lengths to users having nasal lengths greater than the Short/Wide Crossover Axis 2314 (i.e., at approximately 30% of the range of nasal lengths). That is, as shown, the Wide size fits users having nasal lengths between approximately 14.0 to 20.4 mm (compared to approximately 14.0 to 20.4 mm in FIG. 45). The M/L size is configured to fit users having nasal lengths less than the Short/Wide Crossover Axis 2314 to users having the largest nasal lengths. That is, as shown, the M/L size fits users having nasal lengths of approximately 17.6 to 28.8 mm (compared to approximately 17.6 to 28.8 mm in FIG. 45). Accordingly, Wide and M/L sizes provide overlapping coverage of a range of nasal lengths between approximately 17.6 to 20.4 mm (compared to approximately 17.6 to 20.4 mm in FIG. 45). Further, the combination of the Wide and M/L sizes cover substantially the entire range of nasal lengths.

Figure 48:
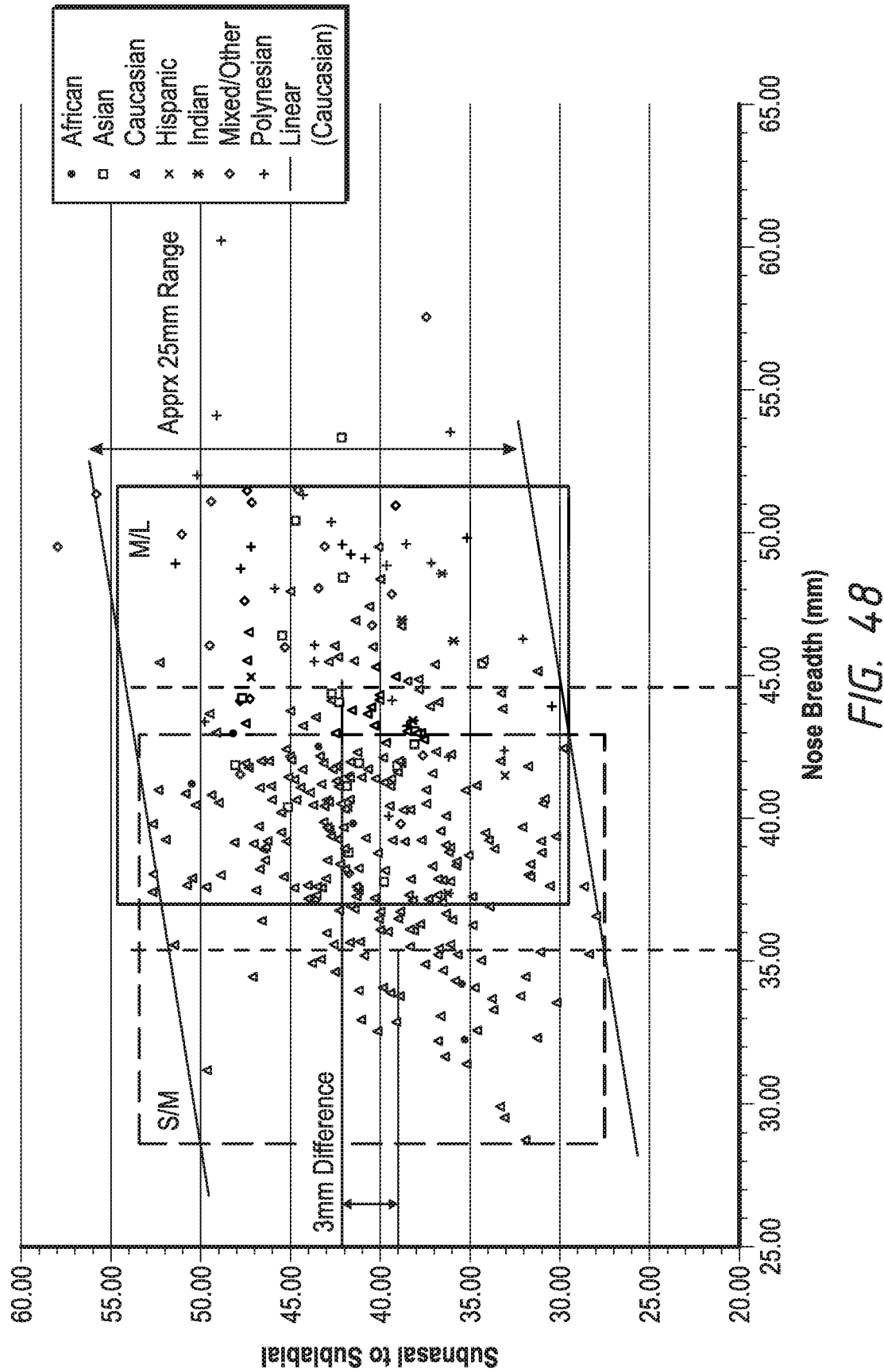
FIG. 48 is a scatter plot of nose breadth versus Subnasal to Sublabial length illustrating a theoretical ethnically diverse population with proposed sizing models represented that will fit an over-nose seal.

FIG. 48 illustrates a seal sizing coverage arrangement based on a scatter plot of nose breadth versus subnasal to sublabial distance that provides a representation of the variation seen in facial geometry. The scatter plot data includes the sizing information of user from different Ethnic groups and shows graphically the wide variance of nasal geometry when considering a population sample that includes different ethnicities. The scatter plot data has been split into different possible sizing models for a nasal under-nose interface. The sizing models address both nasal dimensions—nasal breadth or width and subnasal to sublabial distance. Assuming that a maximum number of seal sizes is set to 2, for example, the seal size ranges could be provided as follows: S/M=small-medium and M/L=medium-large. The coverage of the particular seal sizes is illustrated by the rectangular perimeters, as shown in FIG. 48.

As shown in FIG. 48, the S/M size is configured to fit users having nasal widths between substantially the smallest nasal widths to users having substantially the median nasal width. That is, as shown, the S/M size fits users having nasal widths of approximately 28.5 to 44.0 mm. The M/L size is configured to fit users having substantially the median nasal width to users with substantially the largest nasal widths. That is, as shown, the M/L size fits users having nasal widths of approximately 37.0 to 51.7 mm. Accordingly, the combination of S/M and M/L sizes cover substantially the entire range of nasal widths.

The S/M size is configured to fit users having substantially the smallest measured subnasal to sublabial distance to substantially the largest subnasal to sublabial distance. That is, as shown, the S/M size fits users having subnasal to sublabial distance of approximately 27.5 to 53.4 mm. The M/L size is configured to fit users having the smallest measured subnasal to sublabial distance to substantially the largest subnasal to sublabial distance. That is, as shown, the M/L size fits users having subnasal to sublabial distance of approximately 29.4 to 54.6 mm. Accordingly, the combination of S/M and M/L sizes cover substantially the entire range of subnasal to sublabial distance.

As shown in FIG. 48, as a result of sizing according to an ethnically diverse user population, the S/M and M/L sizes each provide coverage for a similar range of subnasal to sublabial distances but differ in terms of their respective coverage of nasal widths. That is, the ethnically diverse scatter plot indicates that the range of subnasal to sublabial distance is substantially consistent throughout the range to nasal breadth. A linear regression of the scatter plot indicates that the range of subnasal to sublabial distance varies approximately 25 mm throughout the range of nasal widths while the average subnasal to sublabial distance varies only 3 mm between a nasal width range of approximately 35.3 to 44.6 mm. Accordingly, the S/M and M/L sizes provide a similar range of subnasal to sublabial coverage while varying in terms of nasal width coverage. Further, a difference between the average values of the range of subnasal to sublabial distance covered by the S/M and M/L sizes (3 mm) is less than the difference between the average values of the range of nasal width covered by the S/M and M/L sizes (9 mm). That is, when comparing the S/M and M/L sizes, the nasal width of the M/L size is increased or offset by a greater amount than the subnasal to sublabial distance. In other words, a difference between the average and/or median nasal width between the S/M and M/L sizes is greater than a difference between the average and/or median subnasal to sublabial distance between the S/M and M/L sizes. This is in contrast to a general scaling up of both the nasal width and subnasal to sublabial distance by the same factor or multiplier. Accordingly, the ranges of nasal width and subnasal to sublabial distance between the S/M and M/L sizes are each offset by different amounts. It should be understood by one of ordinary skill in the art that, in other configurations, the average and/or median nasal width of the M/L size may be increased or offset by a smaller amount than the amount of increase of the average and/or median subnasal to sublabial distance.

Accordingly, the S/M and M/L sizes provide a similar range of subnasal to sublabial distance coverage while varying to a greater degree in terms of nasal width coverage. That is, the difference (i.e., in terms of amount and/or percentage) between the ranges of subnasal to sublabial distance coverage provided by the S/M and M/L sizes is less than the difference (i.e., in terms of amount and/or percentage) between the ranges of nasal width coverage provided by the S/M and M/L sizes. Put another way, the users that properly fit the S/M size generally have similar subnasal to sublabial distances as the users that properly fit the M/L size. However, the users that properly fit the S/M size have smaller nose widths than the users that properly fit the M/L size.

Figure 49:
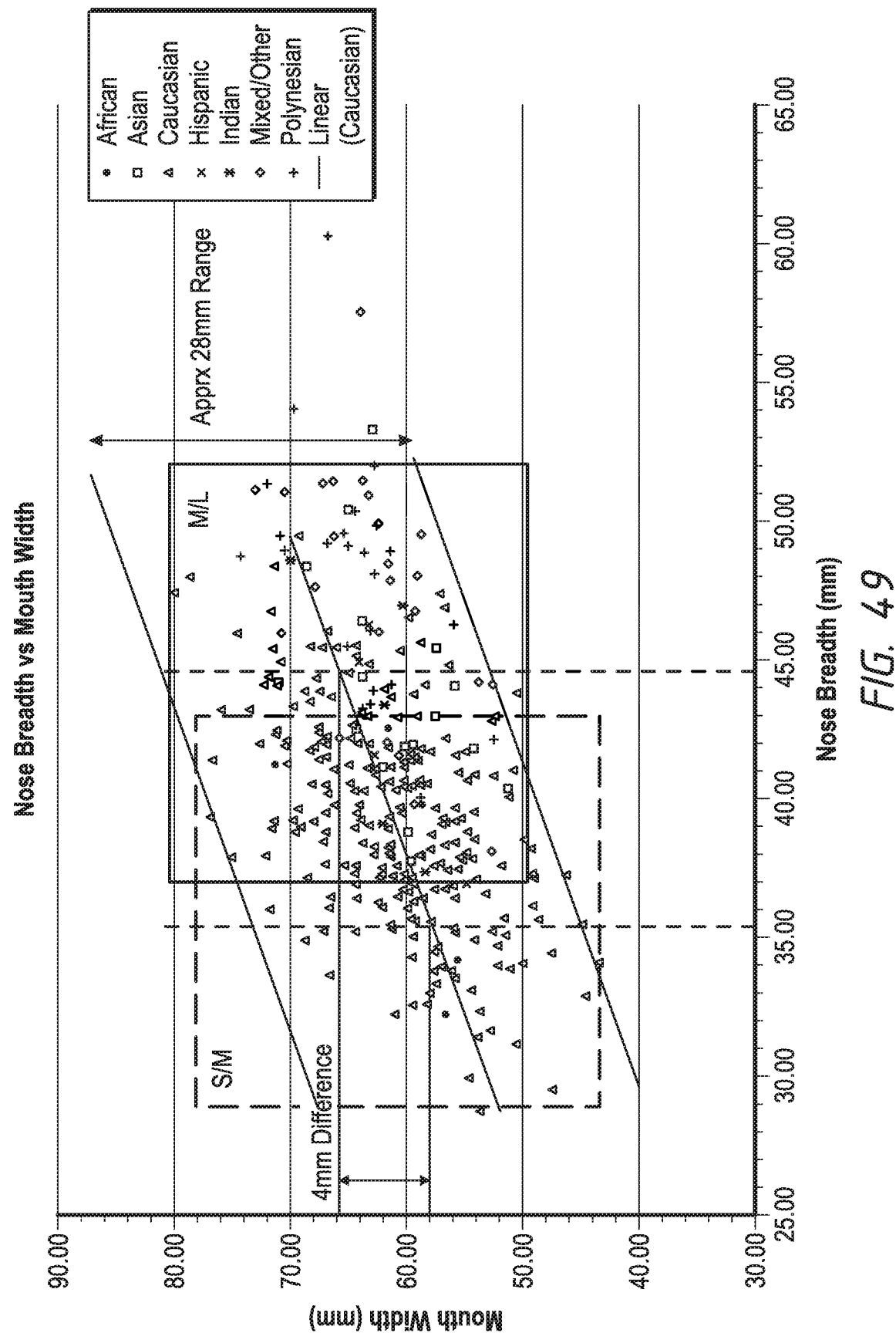
FIG. 49 is a scatter plot of nose breadth versus mouth width illustrating a theoretical ethnically diverse population with proposed sizing models represented that will fit an over-nose seal.

FIG. 49 illustrates a seal sizing coverage arrangement based on a scatter plot of nose breadth versus mouth width that provides a representation of the variation seen in facial geometry. The scatter plot data includes the sizing information of user from different Ethnic groups and shows graphically the wide variance of nasal geometry when considering a population sample that includes different ethnicities. The scatter plot data has been split into different possible sizing models for a nasal under-nose interface. The sizing models address both nasal dimensions—nasal breadth or width and mouth width. Assuming that a maximum number of seal sizes is set to 2, for example, the seal size ranges could be provided as follows: S/M=small-medium and M/L=medium-large. The coverage of the particular seal sizes is illustrated by the rectangular perimeters, as shown in FIG. 49.

As shown in FIG. 49, the S/M size is configured to fit users having substantially the smallest nasal widths to users having substantially the median nasal width. That is, as shown, the S/M size fits users having nasal widths of approximately 29.0 to 43.0 mm. The M/L size is configured to fit users having substantially the median nasal width to users with substantially the largest nasal widths. That is, as shown, the M/L size fits users having nasal widths of approximately 37.0 to 52.0 mm. Accordingly, the combination of S/M and M/L sizes cover substantially the entire range of nasal widths.

The S/M size is configured to fit users having substantially the smallest mouth widths to users having the largest mouth widths. That is, as shown, the S/M size fits users having mouth widths of approximately 41.8 to 79.0 mm. The M/L size is configured to fit users having substantially the smallest mouth widths to users having the largest mouth widths. That is, as shown, the M/L size fits users having mouth widths of approximately 49.8 to 80.2 mm. Accordingly, the combination of S/M and M/L sizes cover substantially the entire range of mouth widths.

As shown in FIG. 49, as a result of sizing according to an ethnically diverse user population, the S/M and M/L sizes each provide coverage for a similar range of mouth widths but differ in terms of their respective coverage of nasal widths. That is, the ethnically diverse scatter plot indicates that the range of mouth widths is substantially consistent throughout the range to nasal breadth. A linear regression of the scatter plot indicates that the range of mouth widths vary approximately 28 mm throughout the range of nasal widths while the average mouth width varies only 4 mm between a nasal width range of approximately 35.3 to 44.6 mm. Accordingly, the S/M and M/L sizes provide a similar range of mouth width coverage while varying to a greater degree in terms of nasal width coverage. That is, the difference (i.e., in terms of amount and/or percentage) between the ranges of mouth width coverage provided by the S/M and M/L sizes is less than the difference (i.e., in terms of amount and/or percentage) between the ranges of nasal width coverage provided by the S/M and M/L sizes. Put another way, the users that properly fit the S/M size generally have similar mouth widths as the users that properly fit the M/L size. However, the users that properly fit the S/M size have smaller nose widths than the users that properly fit the M/L size. Further, a difference between the average and/or median values of the range of mouth widths covered by the S/M and M/L sizes (4 mm) is less than the difference between the average values of the range of nasal width covered by the S/M and M/L sizes (9 mm). That is, when comparing the S/M and M/L sizes, the average and/or median nasal width of the M/L size is increased or offset by a greater amount than the increase of average and/or median mouth width. In other words, a difference between the average and/or median nasal width between the S/M and M/L sizes is greater than a difference between the average and/or median nasal length between the S/M and M/L sizes. This is in contrast to a general scaling up of both the nasal width and the mouth width by the same factor or multiplier. Accordingly, the ranges of nasal width and mouth width between the S/M and M/L sizes are each offset by different amounts and/or percentages. It should be understood by one of ordinary skill in the art that, in other configurations, the average and/or median nasal width of the M/L size may be increased or offset by a smaller amount than the amount of increase of the average and/or median mouth width.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to". Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The term "plurality" refers to two or more of an item. Recitations of quantities, dimensions, sizes, formulations, parameters, shapes and other characteristics should be construed as if the term "about" or "approximately" precedes the quantity, dimension, size, formulation, parameter, shape or other characteristic. The terms "about" or "approximately" mean that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. Recitations of quantities, dimensions, sizes, formulations, parameters, shapes and other characteristics should also be construed as if the term "substantially" precedes the quantity, dimension, size, formulation, parameter, shape or other characteristic. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "1 to 3," "2 to 4" and "3 to 5," etc. This same principle applies to ranges reciting only one numerical value (e.g., "greater than 1") and should apply regardless of the breadth of the range or the characteristics being described.

A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. A seal for an interface for use in providing positive pressure respiratory therapy, the seal comprising:
   a seal body configured to be fully positioned lower than a bridge of a nose of a face of a user and to provide an exposed bridge of the nose of the user, the seal body comprising:
   a nasal region comprising a nasal opening, the nasal region configured to seal against at least a lower portion of the nose of the user,
   a first paddle on a first side of the nasal region and a second paddle on a second side of the nasal region, the first paddle configured to contact and extend upward alongside one side of the nose of the user and the second paddle configured to contact and extend upward alongside the other side of the nose of the user, the first and second paddles each including a support structure comprising an elongate triangular thickened region that extends in a fore-aft direction along a ridge of each of the respective first and second paddles, the support structures being configured to be positioned alongside a user's nose, and
   an oral opening;
   wherein
   a nasal opening-oral opening spacing linear distance between the nasal opening and the oral opening is between 10-15 mm.

2. The seal of claim 1, wherein the seal comprises outwardly projecting portions on each side of the nasal region.

3. The seal of claim 1, wherein each support structure is a suspension member configured to assist in maintaining a desired shape of the paddles.

4. The seal of claim 1, wherein the nasal opening-oral opening spacing linear distance is between 11 and 13 mm.

5. The seal of claim 1, wherein the nasal opening-oral opening spacing linear distance is about 12.7 mm.

6. The seal of claim 1, wherein the nasal opening-oral opening spacing linear distance is about 12.2 mm.

7. The seal of claim 1, wherein the nasal opening-oral opening spacing linear distance is measured between an upper edge of the oral opening and a rearward or lower edge of the nasal opening taken along a centerline of the seal.

8. An interface comprising the seal of claim 1, and a frame removably coupled to the seal.

9. The interface of claim 8, further comprising a pair of covers supported relative to the mask assembly such that each of the covers is positioned adjacent a portion of a respective one of the first and second paddles, wherein the covers limit expansion of at least the portion of the first and second paddles.

10. An interface system, comprising a frame that interchangeably supports at least two mask assemblies, at least one of the at least two mask assemblies comprising a seal according to claim 1.

11. An interface system for providing positive pressure respiratory therapy to users, the system comprising:
a mask frame; and
at least a first seal and a second seal that are interchangeably mountable to the mask frame, the first seal having a first size and the second seal having a second size different than the first size, each of the seals having a seal body configured to be fully positioned lower than a bridge of a nose of a face of a user and to provide an exposed bridge of the nose of the user, each seal comprising a nasal region comprising a nasal opening, each seal comprising a first paddle on a first side of the nasal region and a second paddle on a second side of the nasal region, the first paddle configured to contact and extend upward alongside one side of the nose of the user and the second paddle configured to contact and extend upward alongside the other side of the nose of the user, each of the first paddle and the second paddle including a support structure that extends along a ridge of each of the respective first and second paddles, the support structures being configured to be positioned alongside a user's nose, and each seal comprising an oral opening;
wherein the nasal opening of each of the first and second seals is spaced from the oral opening by a nasal opening-oral opening spacing linear distance of between 10 and 15 mm,
wherein the first size comprises a first lateral distance of the nasal region of the first seal measured between inner edges of the support structure of the first seal,
wherein the second size comprises a second lateral distance of the nasal region of the second seal measured between inner edges of the support structure of the second seal,
wherein the second lateral distance is greater than the first lateral distance.

12. The interface system of claim 11, further comprising:
a third seal that is interchangeably mountable to the mask frame, the third seal having a third size that is different than the first and second sizes, the third seal comprising a third lateral distance,
wherein a nasal opening of the third seal is spaced from an oral opening of the third seal by a nasal opening-oral opening spacing linear distance of between 9 and 14 mm,
wherein the third lateral distance is greater than the first lateral distance.

13. The interface system of claim 11, wherein the first lateral distance is 46 mm.

14. The interface system of claim 11, wherein the second lateral distance is 56 mm.

15. An interface system for providing positive pressure respiratory therapy to users, the system comprising:
a plurality of seals, each of the seals having a seal body configured to be fully positioned lower than a bridge of a nose a nose of a face of a user and to provide an exposed bridge of the nose of the user, each seal comprising a nasal region comprising a nasal opening, each nasal opening comprising a width, each seal comprising a first paddle on a first side of the nasal region and a second paddle on a second side of the nasal region, the first paddle configured to contact one side of the nose of the user and the second paddle configured to contact the other side of the nose of the user, and each seal comprising an oral opening, each of the plurality of seals having different sizes, each of the different sizes comprises a different width of the nasal opening,
the plurality of seals comprising a first seal wherein a nasal opening-oral opening spacing linear distance between the nasal opening and the oral opening is between 10 and 15 mm.

16. The interface system of claim 15, wherein the plurality of seals comprises a second seal and a nasal opening-oral opening spacing linear distance of the second seal is in the range of 9 to 14 mm.

17. The interface system of claim 16, wherein the first seal comprises a first width of the nasal region of the first seal and the second seal comprises a second width of the nasal region of the second seal.

18. The interface system of claim 17, wherein the first width is greater than the second width.

19. The interface system of claim 15, the plurality of seals being interchangeably mountable to a mask frame.

* * * * *

UNITED STATES PATENT AND TRADEMARK OFFICE
CERTIFICATE OF CORRECTION

PATENT NO. : 10,994,090 B2  
APPLICATION NO. : 15/757112  
DATED : May 4, 2021  
INVENTOR(S) : Roheet Patel Page 1 of 1

It is certified that error appears in the above-identified patent and that said Letters Patent is hereby corrected as shown below:

On the Title Page

Column 2, Item (74), Line 1, under Attorney, Agent, or Firm, delete "Olson" and insert --Olson,--.

In the Claims

In Column 42, Claim 15, Line 26, "a nose a nose" and insert --a nose--.

Signed and Sealed this  
Twentieth Day of July, 2021

Drew Hirshfeld  
*Performing the Functions and Duties of the*  
*Under Secretary of Commerce for Intellectual Property and*  
*Director of the United States Patent and Trademark Office*